(12) United States Patent
Sauka-Spengler et al.

(10) Patent No.: US 8,907,073 B2
(45) Date of Patent: Dec. 9, 2014

(54) NUCLEIC ACIDS ENCODING FOXD3 PROMOTER AND METHODS TO ISOLATE FOXD3 EXPRESSING CELLS

(71) Applicant: California Institute of Technology, Pasadena, CA (US)

(72) Inventors: Tatjana Sauka-Spengler, Oxford (GB); Sonja Jane McKeown, Lower Templestowe (AU); Paola A. Betancur, Belmont, CA (US); Marianne Bronner Hansen, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 23 days.

(21) Appl. No.: 13/857,899

(22) Filed: Apr. 5, 2013

(65) Prior Publication Data
US 2013/0273596 A1 Oct. 17, 2013

Related U.S. Application Data

(62) Division of application No. 12/645,431, filed on Dec. 22, 2009, now Pat. No. 8,524,875.

(60) Provisional application No. 61/203,334, filed on Dec. 22, 2008.

(51) Int. Cl.
| | | |
|---|---|---|
| *C12Q 1/68* | (2006.01) | |
| *C12P 21/00* | (2006.01) | |
| *C12N 15/00* | (2006.01) | |
| *G01N 33/53* | (2006.01) | |
| *C07H 21/00* | (2006.01) | |
| *C12Q 1/04* | (2006.01) | |
| *C07K 14/47* | (2006.01) | |
| *C12N 15/11* | (2006.01) | |
| *C12N 15/85* | (2006.01) | |

(52) U.S. Cl.
CPC .............. *C12Q 1/04* (2013.01); *C07K 14/4702* (2013.01); *C12N 15/111* (2013.01); *C12N 15/85* (2013.01); *C12Q 1/6881* (2013.01); *C12Q 1/6897* (2013.01); *C12N 2330/51* (2013.01); *C12N 2830/008* (2013.01); *C12N 2830/15* (2013.01); *C12N 2830/30* (2013.01); *C12N 2830/42* (2013.01); *C12N 2830/85* (2013.01)
USPC ........... 536/24.1; 435/6.1; 435/7.1; 435/70.1; 435/320.1

(58) Field of Classification Search
CPC .............. C12N 2310/14; C12N 15/85; C12N 2830/008; C12N 2830/85; C12N 15/64; C12N 2799/021; C12Q 1/68; C12Q 2600/178
See application file for complete search history.

(56) References Cited

U.S. PATENT DOCUMENTS

| | | |
|---|---|---|
| 2007/0044164 A1 | 2/2007 | Dickins et al. |
| 2008/0118913 A1 | 5/2008 | Scott et al. |
| 2008/0311091 A1 | 12/2008 | Perlmann et al. |

OTHER PUBLICATIONS

Yu, et al., "*RNA interference by expression of short-interfering RNAs and hairpin RNAs in mammalian cells*", PNAS, vol. 99, No. 9, Apr. 30, 2002, pp. 6047-6052.
Xia, et al., "*An enhanced U6 promoter for synthesis of short hairpin RNA*", Nucleic Acids Research, vol. 31, No. 17, 2003, pp. 1-5.
GenBank Accession No. XM_00109089.1, "*Predicted: Macaca mulatta similar to DNA directed RNA polymerase II polypeptide F (LOC699566), mRNA*", Jun. 14, 2006 (2 sheets).
Kaul, et al., "*Homo sapiens chromosome 1 clone RP11-335E6, complete sequence*", GenBank Accession No. AC096543.2, Feb. 14, 2002 (43 sheets).
Smith, "*Zebrafish DNA sequence from clone CH211-22O10 in linkage group 6, complete sequence*", GenBank Accession No. BX470171.6, Oct. 30, 2004 (10 sheets).
Lloyd, "*Mouse DNA sequence from clone RP23-14113 on chromosome 4 Contains two ubiquitin carboxyl-terminal esterase L3 (ubiquitin thiolesterase) (Uchl3) pseudogenes, a glyceraldehyde-3-phosphate dehydrogenase (Gapd) pseudogene, a BCL2/adenovirus E1B 19kDa-interacting protein 3-like (Bnip3l) pseudogene, a novel gene and a CpG island, complete sequence*", GenBank Accession No. AL772237.12, May 3, 2008 (44 sheets).
International Search Report and Written Opinion dated Jan. 11, 2011 for corresponding PCT Application No. PCT/US2009/069343, citing the references listed above (15 sheets).
Abbasi, et al., "*Human GLI3 Intragenic Conserved Non-Coding Sequences Are Tissue-Specific Enhancers*", PLoS ONE, Issue 4, Apr. 2007 (12 sheets).
Antonellis, et al., "*Deletion of long-range sequences at Sox10 compromises developmental expression in a mouse model of Waardenburg-Shah (WS4) syndrome*", Human Molecular Genetics, vol. 15, No. 2, 2006, pp. 259-271.
Antonellis, et al., "*Identification of Neural Crest and Glial Enhancers at the Mouse Sox10 Locus through Transgenesis in Zebrafish*", PLoS Genetics, vol. 4, Issue 9, Sep. 2008, pp. 1-14.
Arman, et al., "*Transcriptional Regulation of Human CD5: Important Role of Ets Transcription Factors in CD5 Expression in T Cells*", The Journal of Immunology, vol. 172, 2004, pp. 7519-7529 (also includes cover page).
Carney, et al., "*A direct role for Sox10 in specification of neural crest-derived sensory neurons*", Development, vol. 133 (23), Sep. 21, 2006, pp. 4619-4630.

(Continued)

Primary Examiner — Thaian N Ton
Assistant Examiner — Titilayo Moloye
(74) Attorney, Agent, or Firm — Christie, Parker & Hale, LLP

(57) ABSTRACT

DNA enhancer sequences are provided for use in constructs to identify early stage embryonic cells. The enhancer sequences can be used in parallel with short-hairpin RNA in a vector construct for endogenously regulated gene knockdowns. The disclosed enhancer sequences can be used to isolate a selected population of early stage embryonic cells.

9 Claims, 48 Drawing Sheets
(39 of 48 Drawing Sheet(s) Filed in Color)

(56) References Cited

OTHER PUBLICATIONS

Chang, et al., "*Pathfinding by cranial nerve VII (facial) motorneurons in the chick hindbrain*", Development, vol. 114, 1992, pp. 815-823.

Cheng, et al., "*Chick Sox10, a transcription factor expressed in both early neural crest cells and central nervous system*", Developmental Brain Research, vol. 121, 2000, pp. 233-241.

Cheung, et al., "*Neural crest development is regulated by the transcription factor Sox9*", Development 130 (23), Aug. 18, 2003, pp. 5681-5693.

Dahl, et al., "*A rapid micro chromatin immunoprecipitation assay (µChIP)*", Nature Protocols, vol. 3, No. 6, May 29, 2008, pp. 1032-1045.

Deal, et al., "*Distant Regulatory Elements in a Sox10-βGEO BAC Transgene Are Required for Expression of Sox10 in the Enteric Nervous System and Other Neural Crest-Derived Tissues*", Developmental Dynamics, vol. 235, 2006, pp. 1413-1432.

Dutton, et al., "*An evolutionarily conserved intronic region controls the spatiotemporal expression of the transcription factor Sox10*", BMC Developmental Biology, vol. 8, No. 105, Oct. 26, 2008 (20 sheets).

Finzsch, et al., "*Sox9 and Sox10 influence survival and migration of oligodendrocyte precursors in the spinal cord by regulating PDGF receptor α expression*" Development, vol. 135 (4), 2008, pp. 637-646.

Gunther, et al, "*Sequence-specific DNA binding of the proto-oncoprotein ets-1 defines a transcriptional activator sequence within the long terminal repeat of the Moloney murine sarcoma virus*", Genes & Development, vol. 4, 1990, pp. 667-679 (also includes appendix sheet).

Hong, et al., "*Sox proteins and neural crest development*", Seminars in Cell & Developmental Biology, vol. 16, 2005, pp. 694-703.

Jia, et al., "*A strategy for constructing and verging short hairpin RNA expression vectors*", Journal of RNAi and Gene Silencing, vol. 3, No. 1, May 2007, pp. 248-253.

Karafiat, et al., "*Transcription factor c-Myb is involved in the regulation of the epithelial-mesenchymal transition in the avian neural crest*", Cellular and Molecular Life Sciences, vol. 62, 2005, pp. 2516-2525.

Kelsh, "*Sorting out Sox10 functions in neural crest development*", BioEssays, vol. 28.8, 2006, pp. 788-798.

Martinsen, et al., "*Neural Crest Specification Regulated by the Helix-Loop-Helix Repressor Id2*", Science, vol. 281, Aug. 14, 1998, pp. 988-991 (also includes cover page).

Meulemans, et al., "*Gene-Regulatory Interactions in Neural Crest Evolution and Development*", Developmental Cell, vol. 7, Sep. 2004, pp. 291-299.

Nikitina, et al., "*Dissecting early regulatory relationships in the lamprey neural crest gene network*", PNAS, vol. 105, No. 51, Dec. 23, 2008, pp. 20083-20088.

Sauka-Spengler, et al., "*Development and evolution of the migratory neural crest: a gene regulatory perspective*", Current Opinion in Genetics & Development, vol. 16, 2006, pp. 360-366.

Sauka-Spengler, et al., "*A gene regulatory network orchestrates neural crest formation*", Nature Reviews Molecular Cell Biology, vol. 9, Jul. 2008, pp. 557-568.

Tahtakran, et al., "*Ets-1 expression is associated with cranial neural crest migration and vasculogenesis in the chick embryo*", Gene Expression Patterns, vol. 3, 2003, pp. 455-458.

Stolt, et al., "*Transcription factors Sox8 and Sox10 perform non-equivalent roles during oligodendrocyte development despite functional redundancy*", Development, vol. 131 (10), 2004, pp. 2349-2358.

Taylor, et al., "*SoxE Factors Function Equivalently during Neural Crest and Inner Ear Development and Their Activity is Regulated by SUMOylation*", Developmental Cell, vol. 9, Nov. 2005, pp. 593-603.

Théveneau, et al., "*Ets-1 Confers Cranial Features on Neural Crest Delamination*", PLoS ONE, Issue 11, Nov. 2007 (16 sheets).

Uchikawa, et al., "*Functional Analysis of Chicken Sox2 Enhancers Highlights an Array of Diverse Regulatory Elements that Are Conserved in Mammals*", Developmental Cell, vol. 4, Apr. 2003, pp. 509-519.

Werner, et al., "*Multiple conserved regulatory elements with overlapping functions determine Sox10 expression in mouse embryogenesis*", Nucleic Acids Research, vol. 35, No. 19, 2007, pp. 6526-6538.

Zaiman, et al., "*CBF, Myb, and Ets Binding Sites Are Important for Activity of the Core I Element of the Murine Retrovirus SL3-3 in T Lymphocytes*", Journal of Virology, vol. 72, No. 4, Apr. 1998, pp. 3129-3137.

Hromas, et al., "*Genesis, a Winged Helix transcriptional repressor, has embyonic expression limited to the neural crest, and stimulates proliferation in vitro in a neural development model*", Cell Tissue Res., vol. 297, No. 3, Sep. 1999, pp. 371-382.

Kos, et al., "*The winged-helix transcription factor FoxD3 is important for establishing the neural crest lineage and repressing melanogenesis in avian embryos*", Development, vol. 128 (8), Apr. 2001, pp. 1467-1479.

Labosky, et al., "*The winged helix transcription factor Hfh2 is expressed in neural crest and spinal cord during mouse development*", Mechanisms of Development, vol. 76, No. 1-2, Aug. 1998, pp. 185-190.

Lister, et al al., "*Zebrafish Foxd3 is required for development of a subset of neural crest derivatives*", Developmental Biology, vol. 290, No. 1, Feb. 1, 2006, pp. 92-104.

Pohl, et al., "*Overexpression of the transcriptional repressor FoxD3 prevents neural crest formation in Xenopus embryos*", Mechanisms of Development, vol. 103, No. 1-2, May 2001, pp. 93-106.

Sasai, "*Roles of Sox factors in neural determination: conserved signaling in evolution?*", International Journal of Developmental Biology, vol. 45, No. 1, 2001, pp. 321-326.

Yamagata, et al., "*The winged-helix transcription factor CWH-3 is expressed in developing neural crest cells*", Neuroscience Letters, vol. 249, No. 1, Jun. 12, 1998, pp. 33-36.

Haldin, et al., "*SoxE factors as multifunctional neural crest regulatory factors*", International Journal of Biochemistry & Cell Biology, vol. 42, No. 3, Mar. 2010, pp. 441-444.

Chapman, et al., "Improved method for chick whole-embryo culture using a filter paper carrier", Developmental Dynamics, vol. 220, No. 3, Mar. 2001, pp. 284-289.

Das, et al., "A robust system for RNA interference in the chicken using a modified microRNA operon", Developmental Biology, vol. 294, No. 2, Jun. 15, 2006, pp. 554-563.

Mende, et al., "*Specific and effective knock-down in early chick embryos using morpholinos but not pRFPRNAi vectors*", Mechanisms of Development, vol. 125, No. 11-12, Nov.-Dec. 2008, pp. 947-962.

Jiang, et al., "*Isolation and characterization of neural crest stem cells derivedfrom in vitro-differentiated human embryonic stem cells*", Stem Cells and Development, vol. 18, No. 7, Sep. 2009, pp. 1059-1070.

Megason, et al., "*A mitogen gradient of dorsal midline Wnts organizes growth in the CNS*", Development, vol. 129, No. 9, May 2002, pp. 2087-2098.

Acloque, et al., "*In situ hybridization analysis of chick embryos in whole-mount and tissue sections*", Methods in Cell Biology, vol. 87, 2008, pp. 169-185.

Buchholz, et al., "*Methods in Signal Transduction*", Analysis of Growth Factor Signaling in Embryos, Aug. 15, 2006, pp. 257-271.

Wilkinson, "*In situ Hybridization: A Practical Approach*", Feb. 1992, pp. 75-83.

Sauka-Spengler, et al., "*Gain-and loss-of-function approaches in the chick embryo*", Methods in Cell Biology, vol. 87, 2008, pp. 237-256.

Yamamoto et al., "Lentivirus vectors expressing short hairpin RNAs against the U3-overlapping region of HIV nef inhibit HIV replication and infectivity in primary macrophages", Blood, vol. 108; No. 10, Prepublished online Jul. 20, 2006, pp. 3305-3312.

Genbank Accession No. 147863, Apr. 15, 2004, pp. 1-48.

FIGURE 2

| Frag. | 5' Primer | 3' Primer | Genomic Position | Predicted Size |
|---|---|---|---|---|
| Sox10_5 | SEQ ID NO:175 GTGTAGAGCCCGGTGGTG | SEQ ID NO: 176 AAGCAACTCACCGCCATC | Chr. 1 52975810-52978750 | 2941 |
| Sox10_6 | SEQ ID NO: 177 TGCAGAAAGCATGGCAGA | SEQ ID NO: 178 CACCAGGTGCCAACACAA | Chr. 1 52979561-52982340 | 2780 |
| Sox10_7 | SEQ ID NO: 179 CCAGCTCCCTCAGCCTTT | SEQ ID NO: 180 ATGCCACATCCCTGAAAA | Chr. 1 52985449-52990190 | 4742 |
| Sox10L8 | SEQ ID NO: 181 GATGCCTGGATGGTGCTC | SEQ ID NO: 182 TTCAGTGCTTTGCCACCA | Chr. 1 52990575-52993590 | 3016 |
| Sox10_9 | SEQ ID NO: 183 GTGCTGGTGAGCCGAACT | SEQ ID NO: 184 GAGGGCAAGCACCTCAGA | Chr. 1 52992960-52994741 | 1782 |
| Sox10_10 | SEQ ID NO: 185 GCCGTGTGTCTTCCCATC | SEQ ID NO: 186 ATCCCCACCACGGAGTCT | Chr. 1 52995526-52999473 | 3948 |
| Sox10E | SEQ ID NO: 187 GGGGATACTGGCCTGCTT | SEQ ID NO: 188 AAGGCCCACAGCAGAGTG | Chr. 1 53010305-53014595 | 4291 |

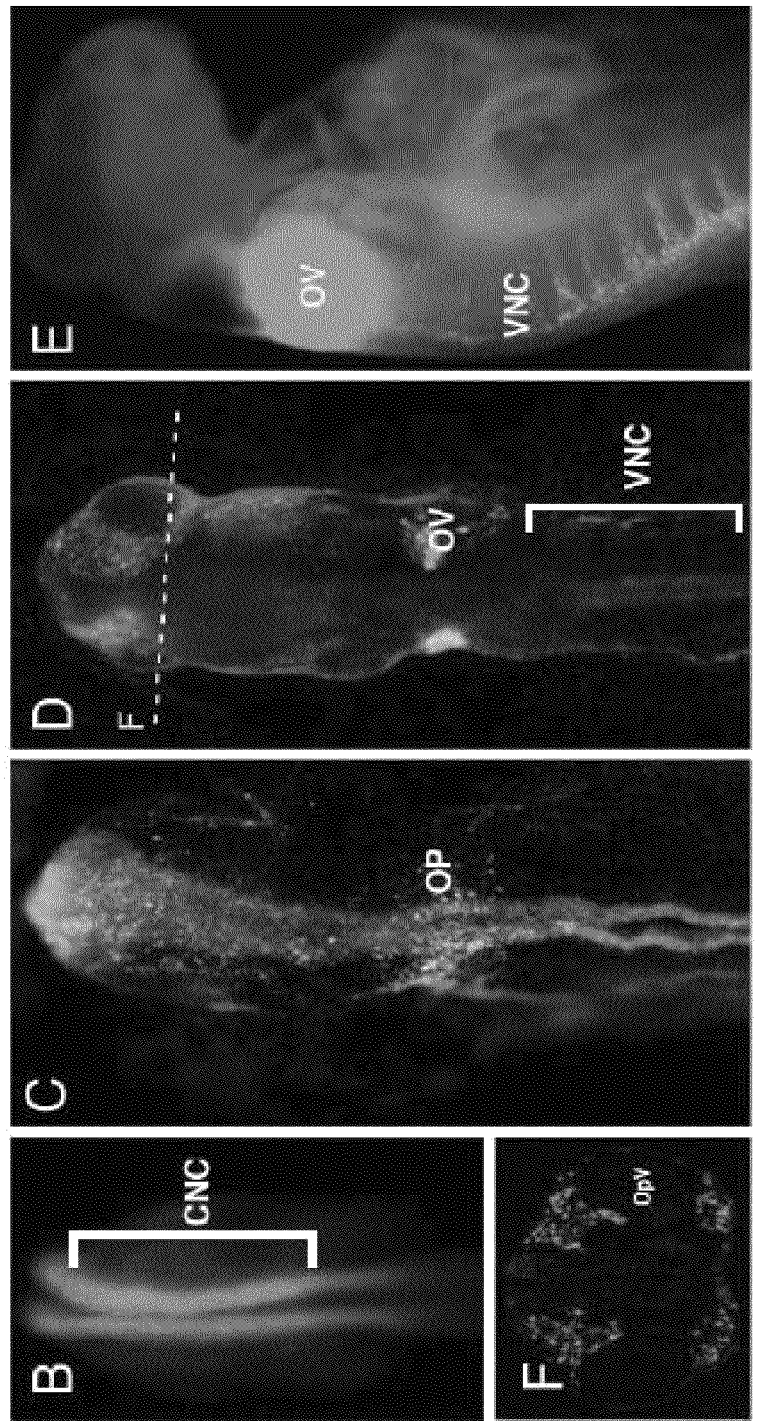

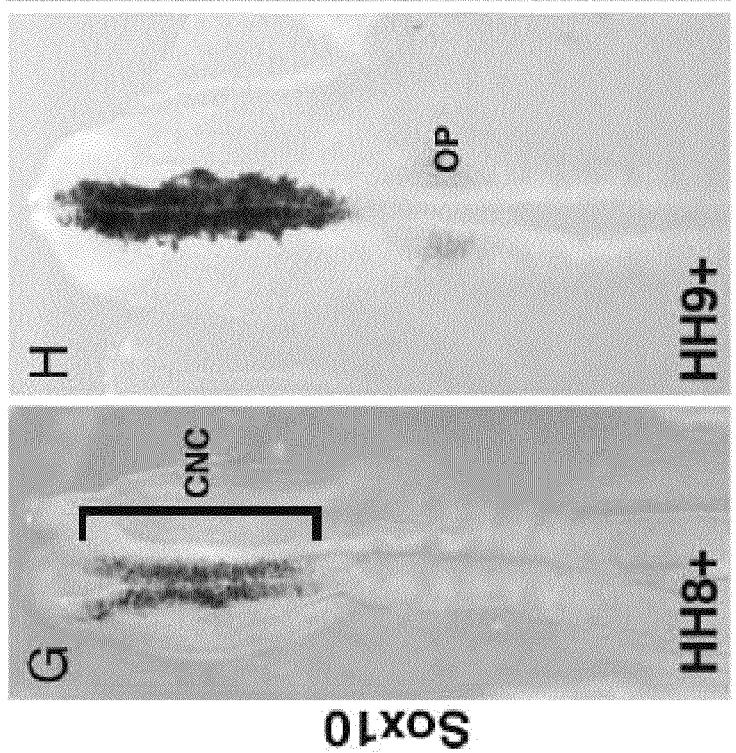
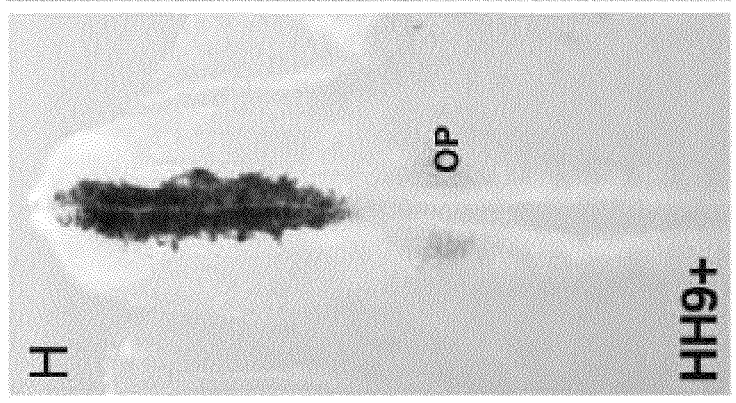
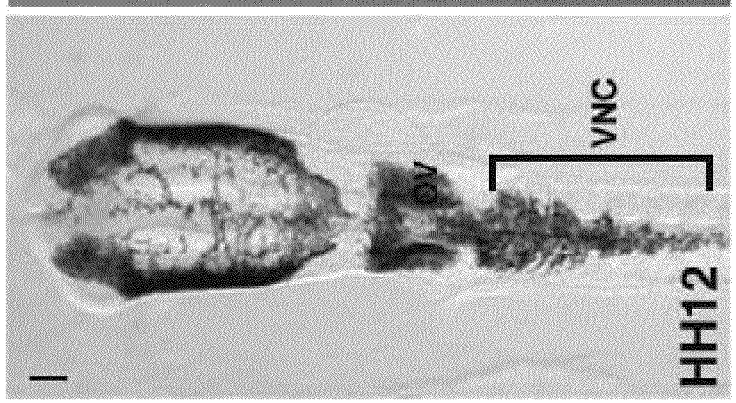
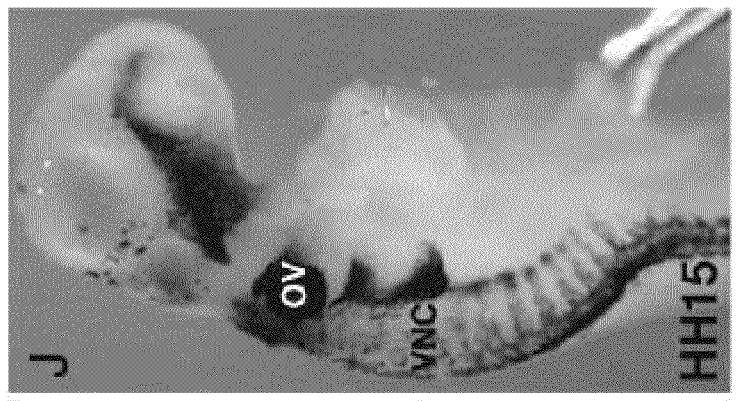

FIG. 4A   FIG. 4B   FIG. 4C
Sox10E1-EGFP   Sox10E2-EGFP
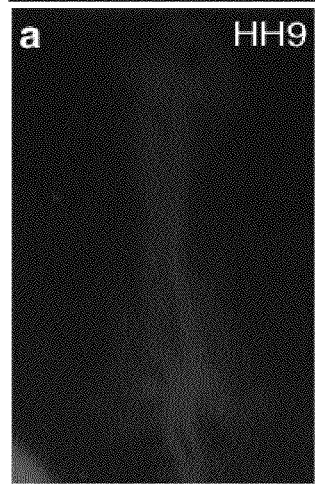
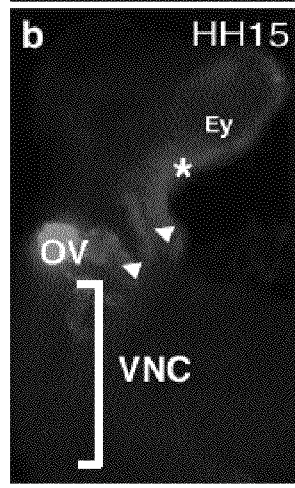
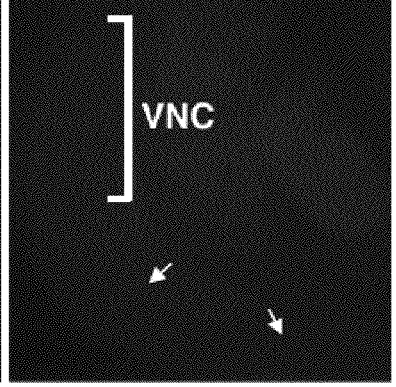
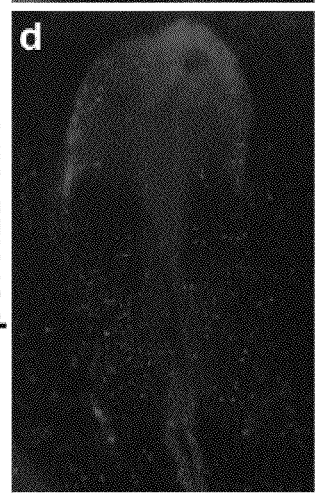
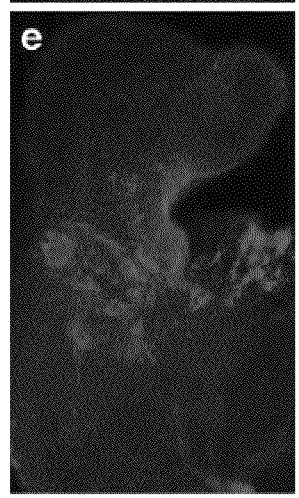
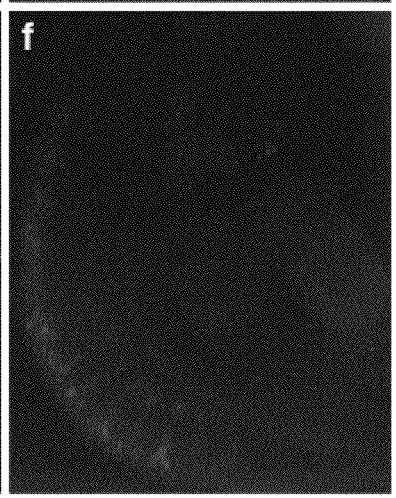
FIG. 4D   FIG. 4E   FIG. 4F

```
                                         PAX (M1)              Myb (M2)              Pax (M3)
SEQ ID NO: 3    A  Chicken   ggca------------agagtggcaattta----acctacaactgctgagcttg-----taggactgtga
   SEQ ID NO: 189  Human     gg----gggcaggggtaggcaggtgctcggtccttgctccagctgctga-cttgcccagcagggctctgc
   SEQ ID NO: 190  Mouse     ------------------------------------------------------------------------
   SEQ ID NO: 191  Rat       ggcactggcctgggacagagtggtgatagg-----gctgcagttgctgc-cttgcccaacagggctctgc
SEQ ID NO: 192    Opossum    ------------------------------------------------------------------------
                  X. tropicalis----------------------------------------------------------------------

Chicken    ctggcga
                  Human      ctgggga
                  Mouse      -------
                  Rat        ctgggga
                  Opossum    -------
                  X.tropicalis -------

Elk (M4)     Pax (M5)    NFKB1(M6)/Pax (M7)
                  Chicken    ctgtgcttccggctggggcagtgccactgaaagggatcccatcacatgataagc-------agcaggag
                  Human      ccacgcttcctgctggggcactgctcctgaaagggatccgagcccacgataagaggctcgaagcaggtc
                  Mouse      ccacgcttcctgctaaagcaccgctcctgaaagggatccgagtcctcgataaga-gctctaggcaggtc
                  Rat        ccacgcttcctgctaaagcaccgctcctgaaagggatcgagtcctcgataaga-gctcaaggcaggtc
                  Opossum    ctatgcttcctggagggactctgctcctgaaagggatcccgatgggtgataaggggcttggggcaggtc
                  X.tropicalis---------------------------------------------------------------------

SoxE (M8)
                  Chicken    caggga-aacaataggtgatttgatgagagctgctctacgatactcct-------gagaagaccc-acag
                  Human      cttagga-aacaatgggtggcttgatgagacctgctctgtgatactcctgagaagggagaagcccctgcag
                  Mouse      cctagg-aacaatggctggcttgatgaaacctgctctgtgatactcctgagaagggagaagcccctgcag
                  Rat        cctagg-aacaatggctggcttgatgaaacctgctctgtgatactcctgagaagggagaagcccctgcag
                  Opossum    ctcagga-aacaatgggtggtttgatgagacctgctctgtgatactcct-------gagaagcccccgaag
                  X.tropicalis---------------------------------------------------------------------

Ets (M9)NFKB1/Ets (M10)       SoxE (M11) Myb (M12)
                  Chicken    ccagctctggccagagaggaaattggggctccacagcaacctgctca--gggcacaaaggcccaactg
                  Human      ccagtccccactggaaaggaaattggggctccagtggcaaccagctccctgggcacaaagacttgtctg
                  Mouse      ccagtccccactggaaaggaaattggggctccggtagcaaccagctccctgggcacaaagactcatctg
                  Rat        ccagtccccactggaaaggaaattggggctccggtggcaaccagctccctgggcacaaagactcatctg
                  Opossum    tcagtccccatcgg--aggaaattgaaggctccatggtaaccagctccccgggcacaaaggccggtctg
                  X.tropicalis---------------------------------------------------------------------

SoxD (M13)
                  Chicken    tcta-ggggggaagcaat
                  Human      tctgcttggaaggcagc
                  Mouse      tctgctgagaaggcagc
                  Rat        tctgctgagaaggcagc
                  Opossum    tctgctggggaggcagc
                  X.tropicalis ---------------
```

FIG. 7A

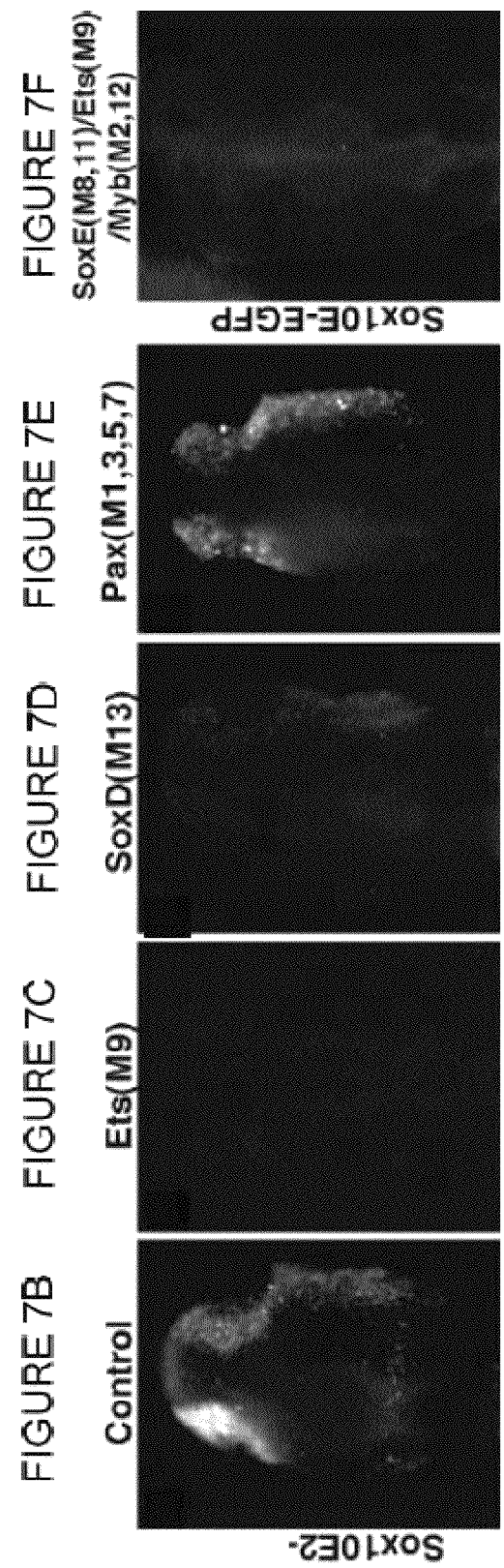

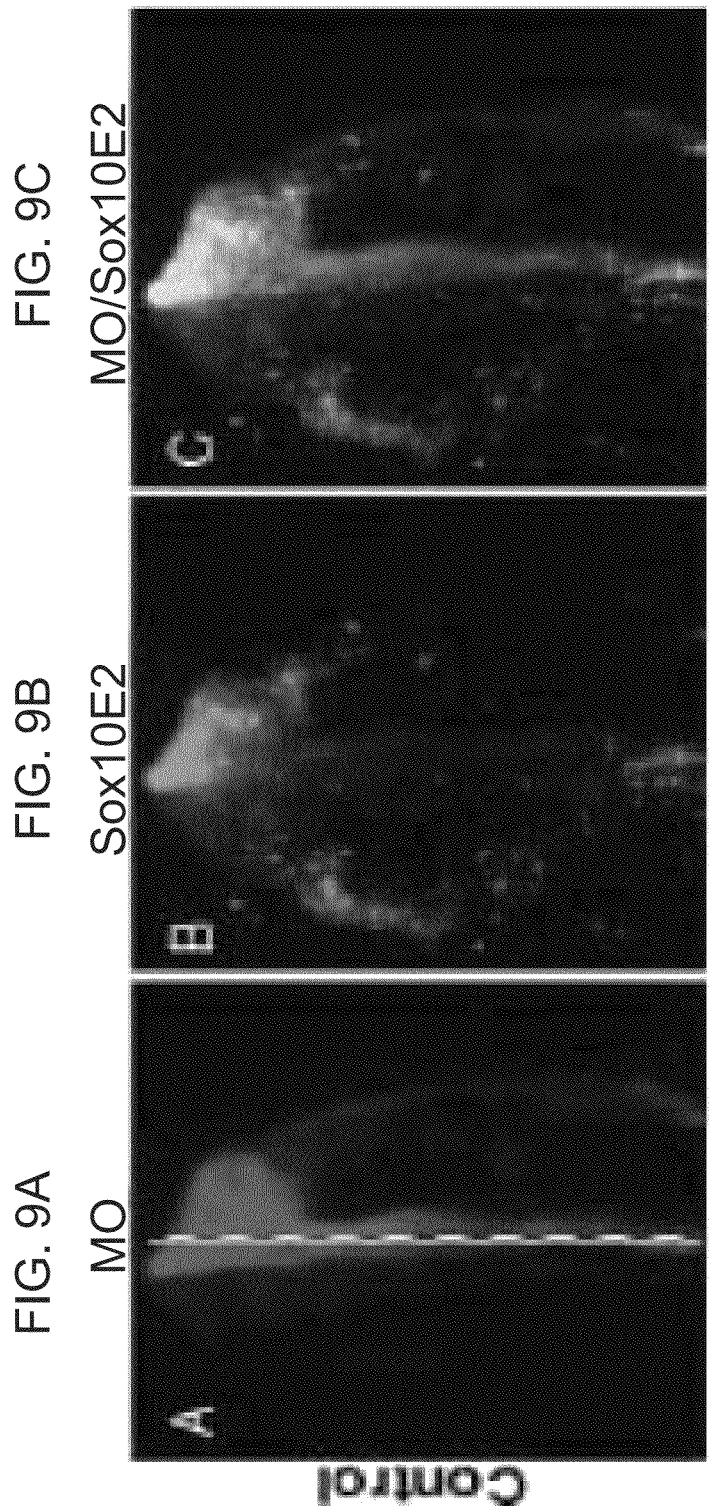

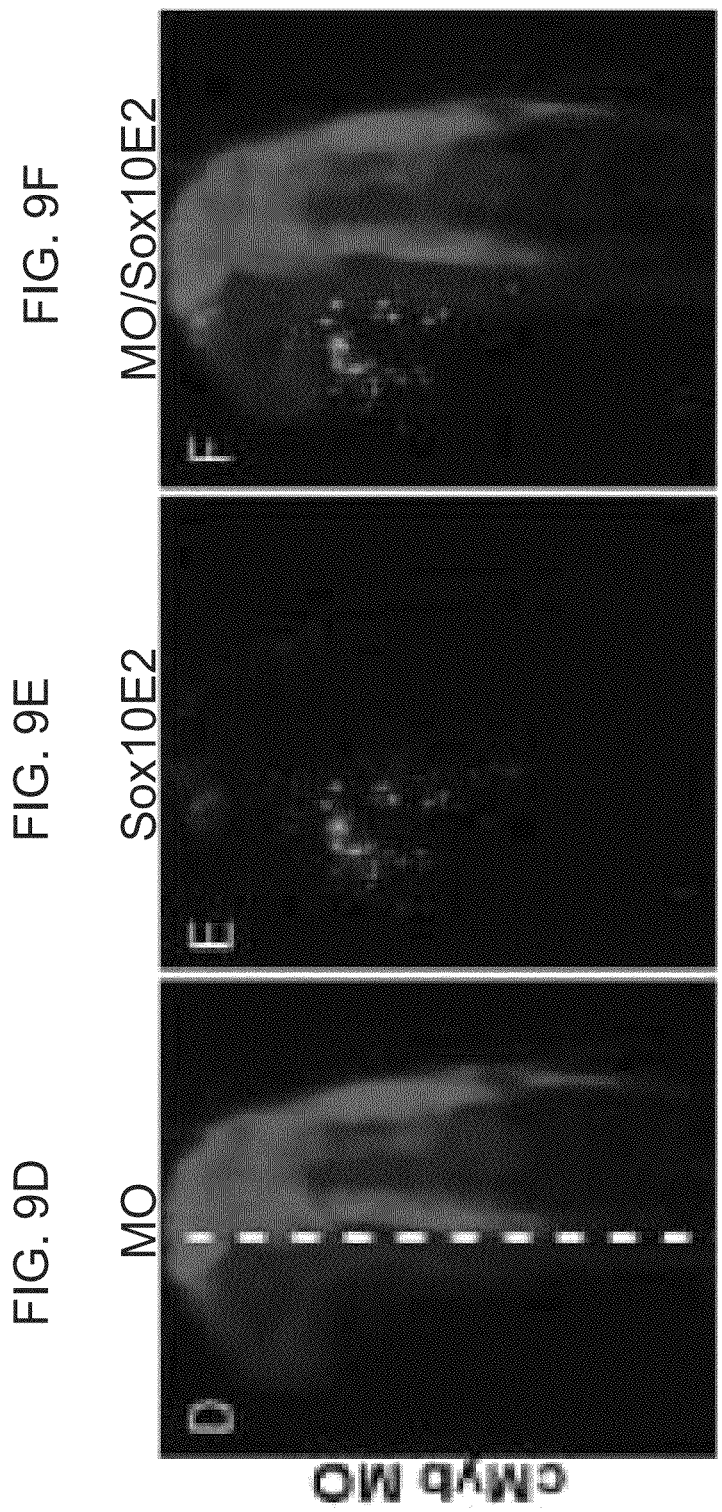

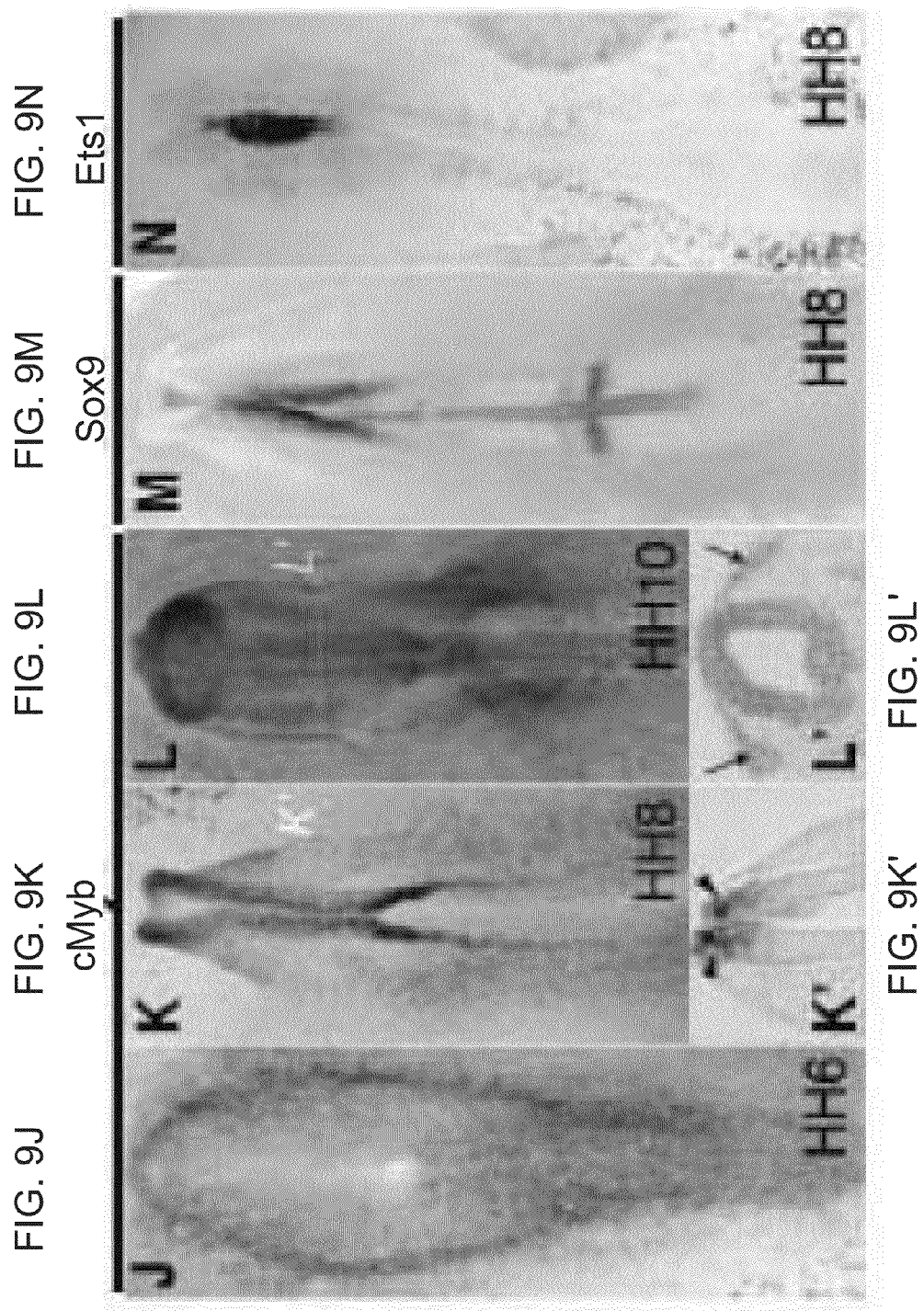

FIG. 10A MO

FIG. 10B Sox10E2

FIG. 10C MO / Sox10E2

Control MO

Sox9 MO

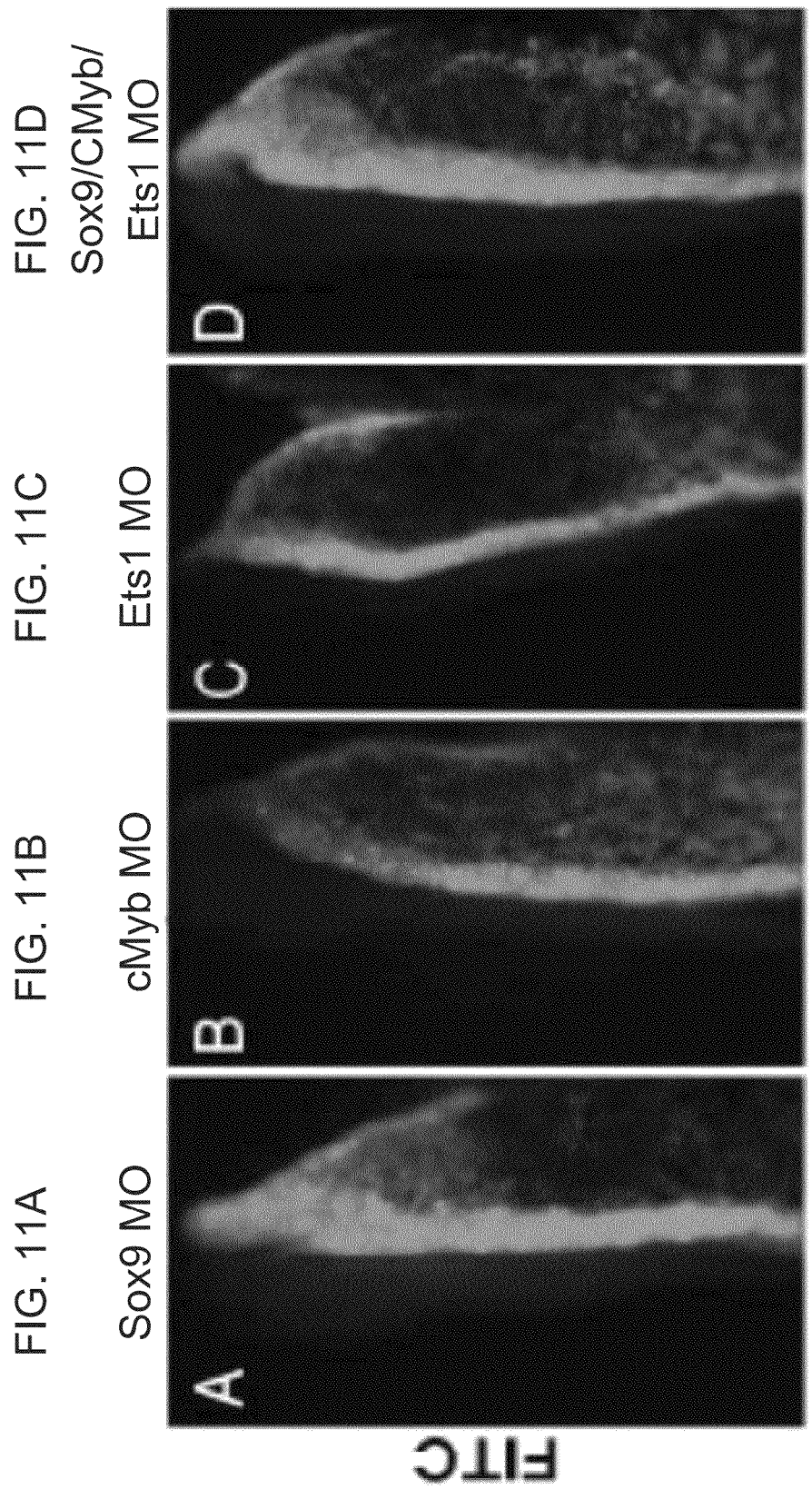

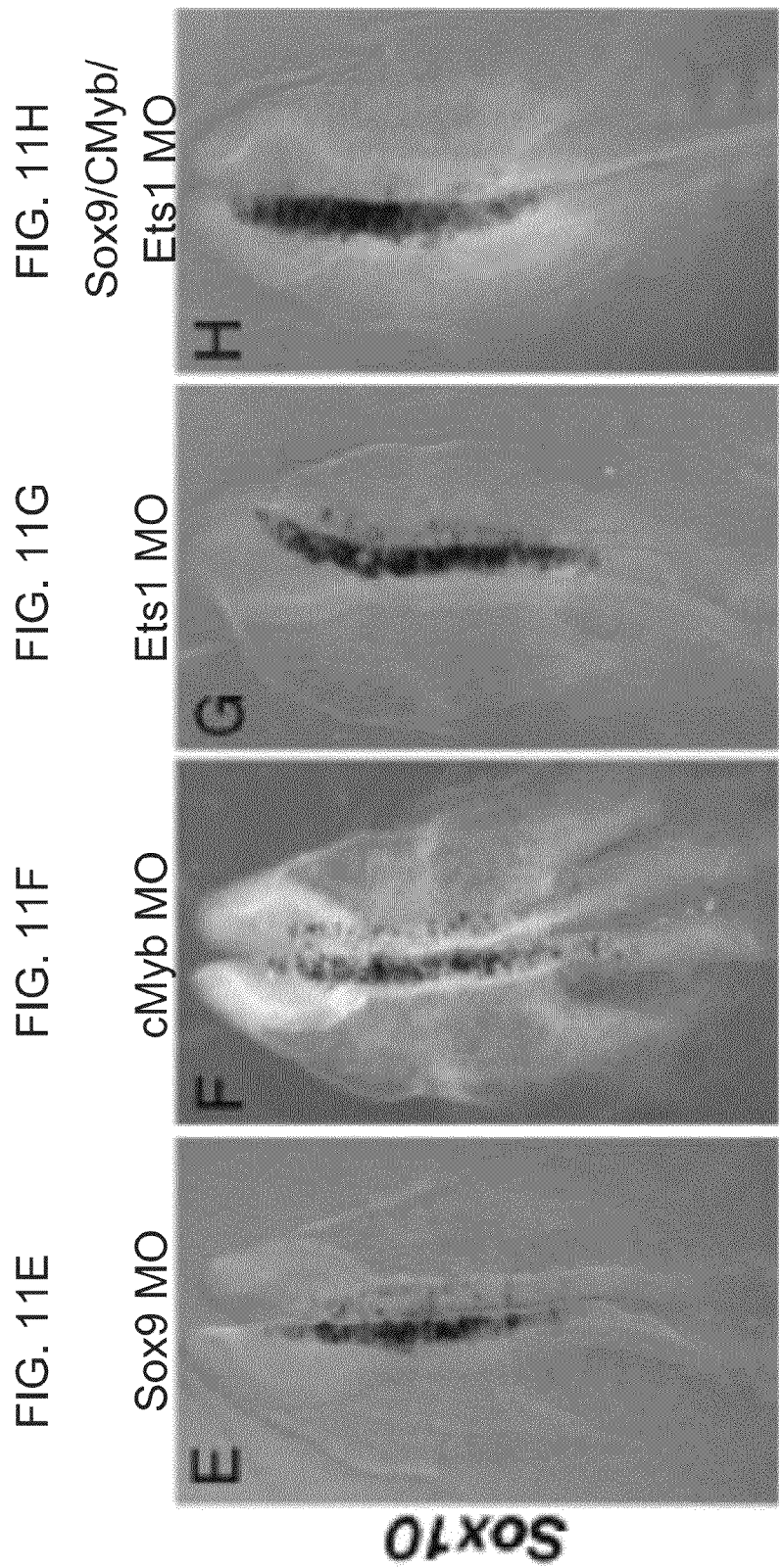

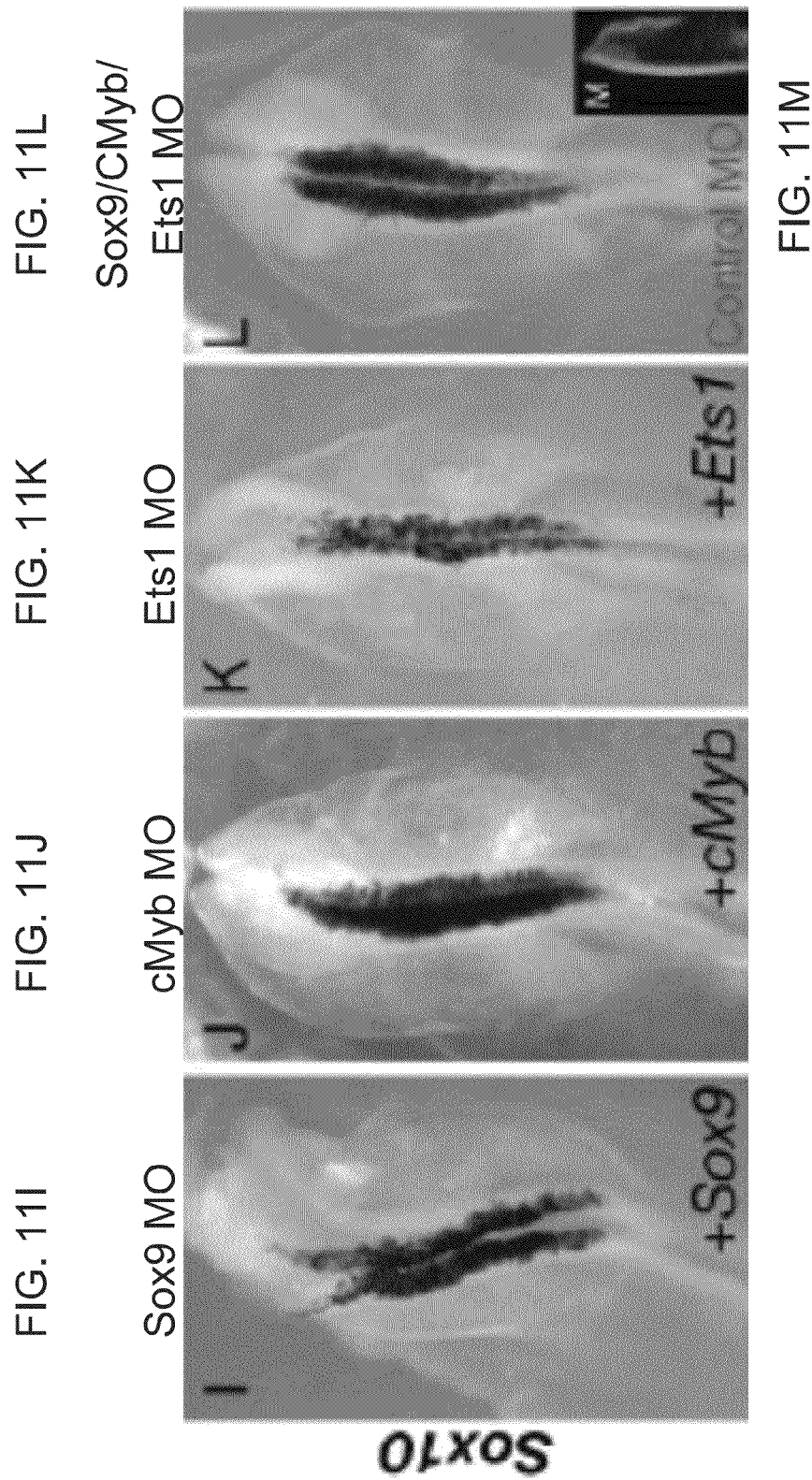

FIG. 12A Ets1 MO+c-Myb MO+Sox9 MO
FIG. 12B Control MO

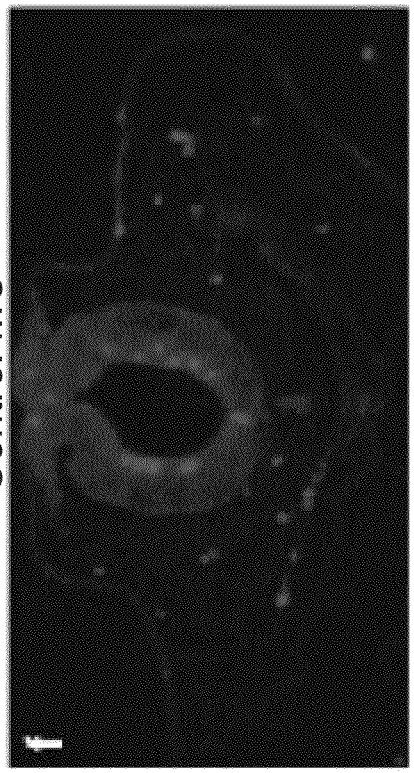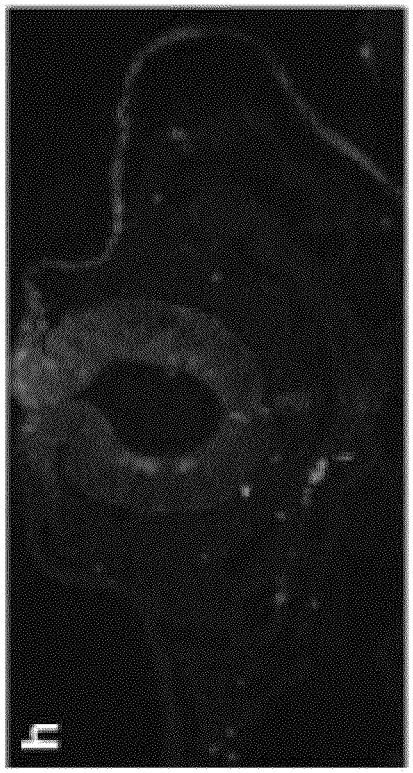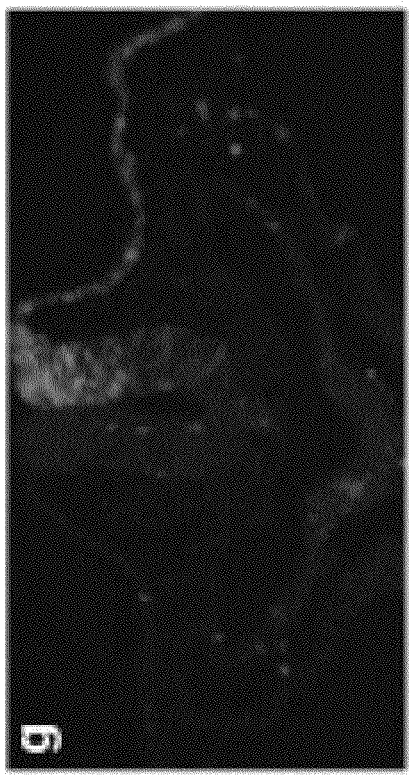
FIG. 12E Ets1 MO+c-Myb MO+Sox9 MO
FIG. 12F Control MO
FIG. 12G
FIG. 12H

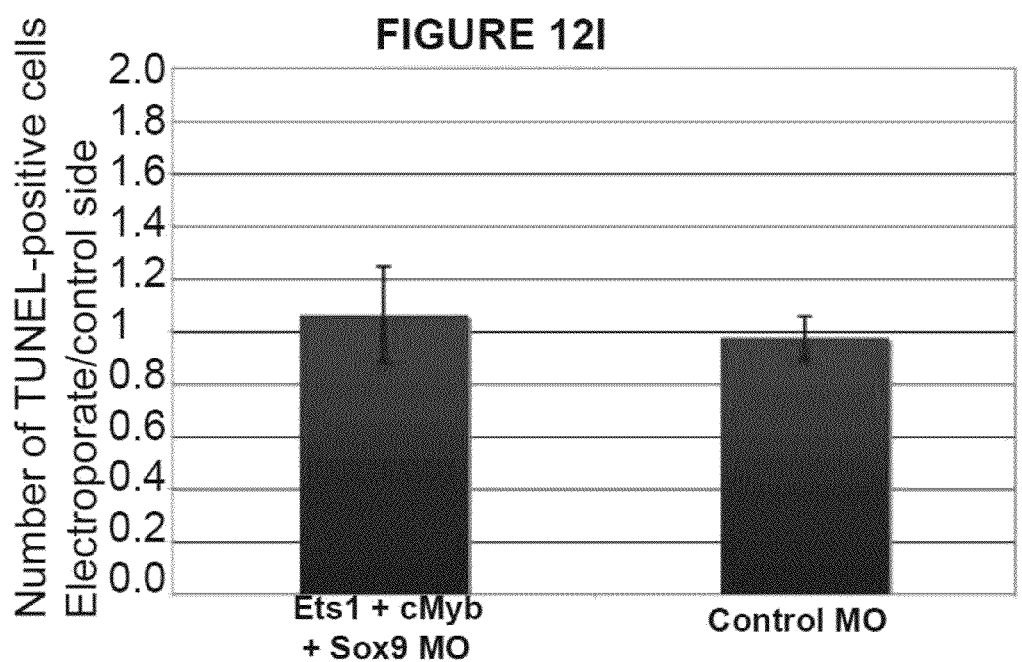
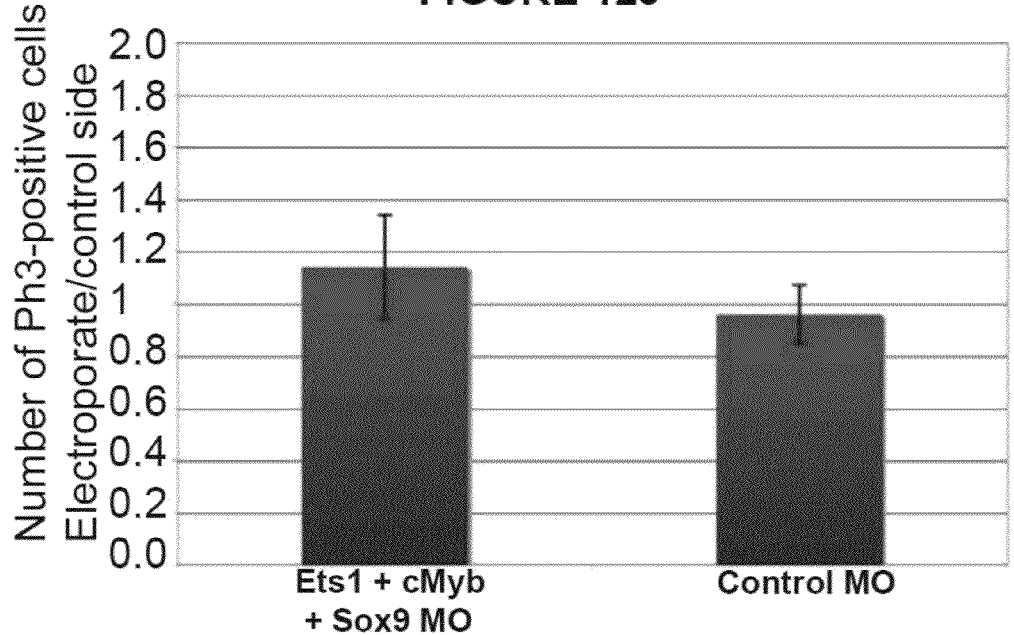

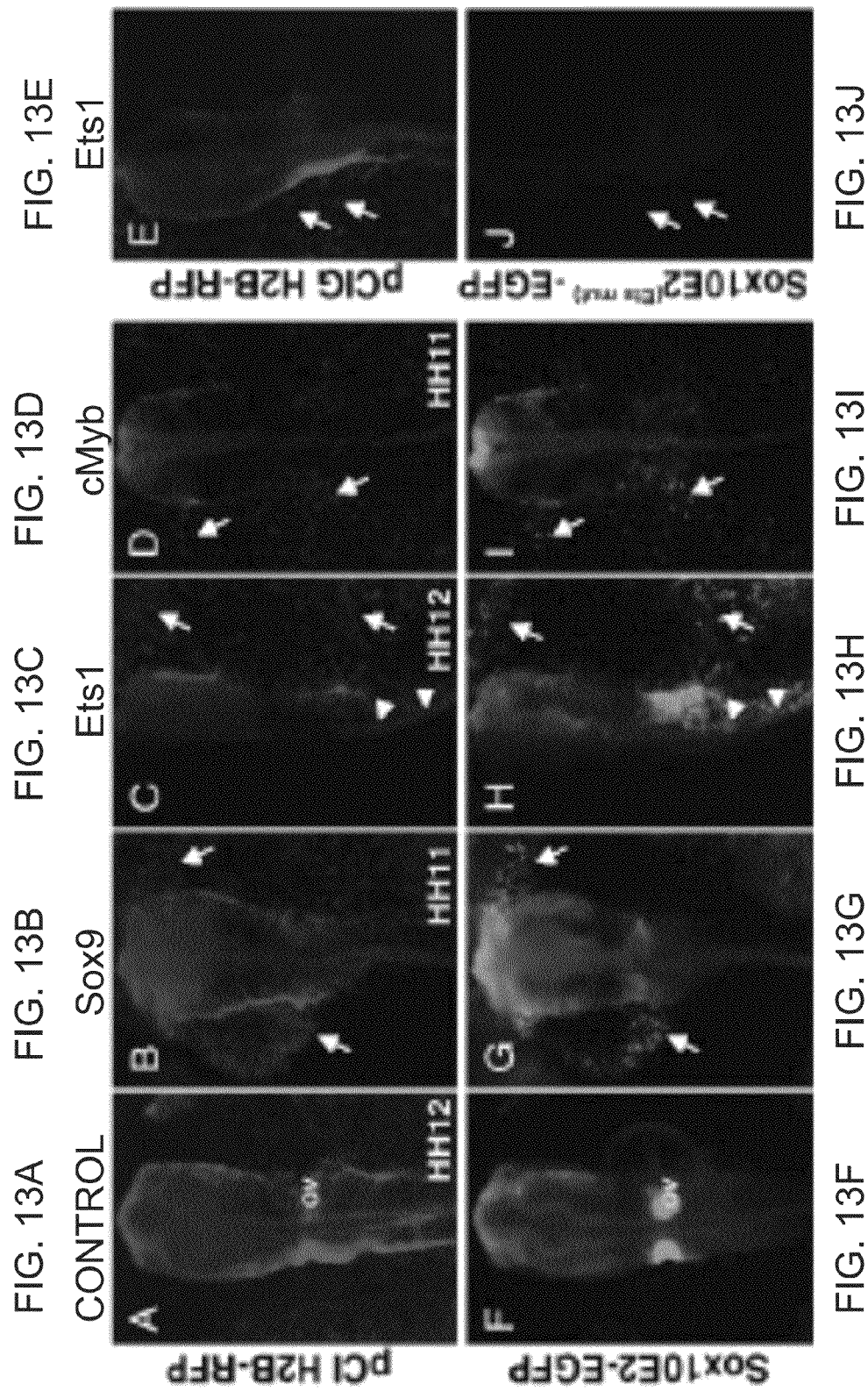

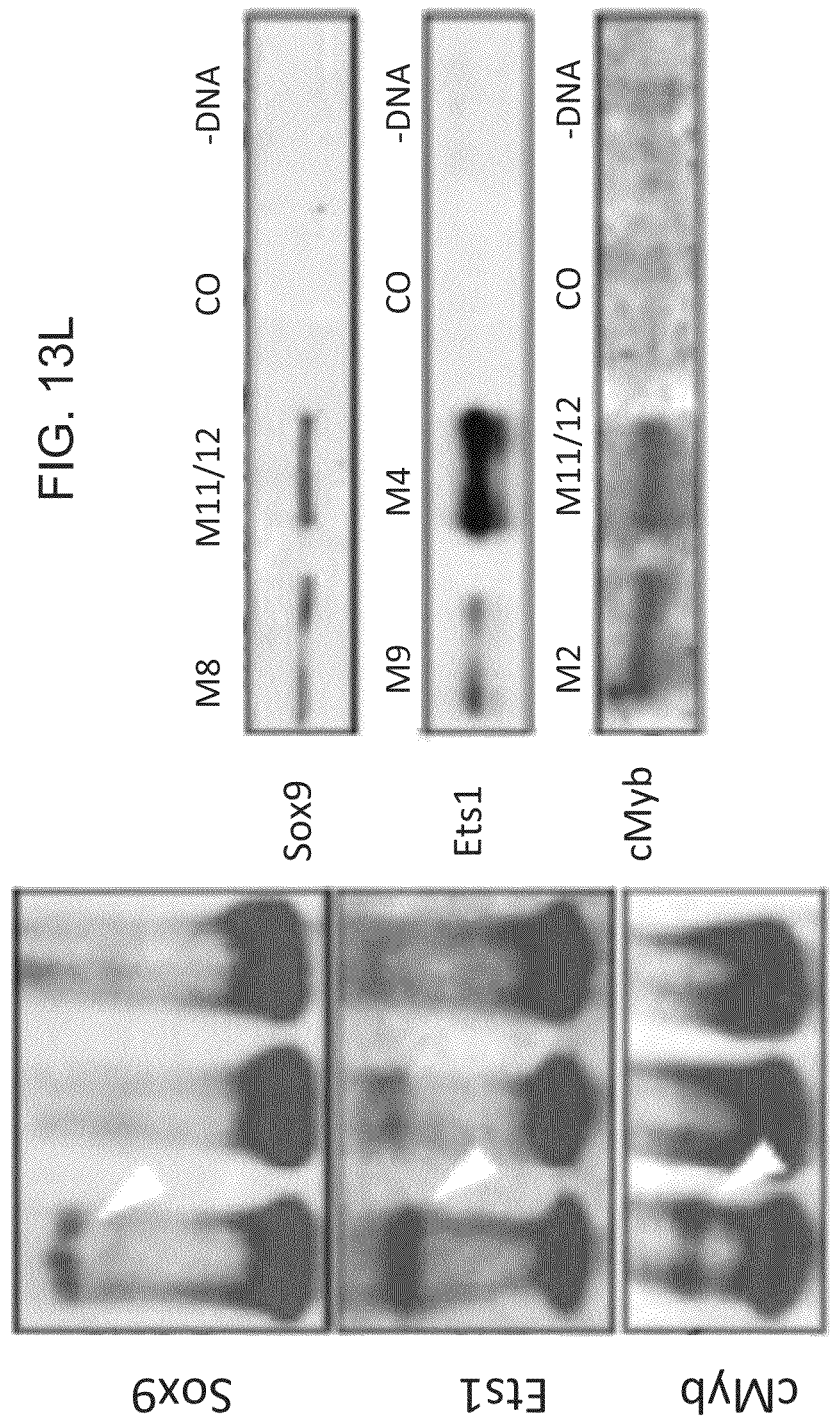

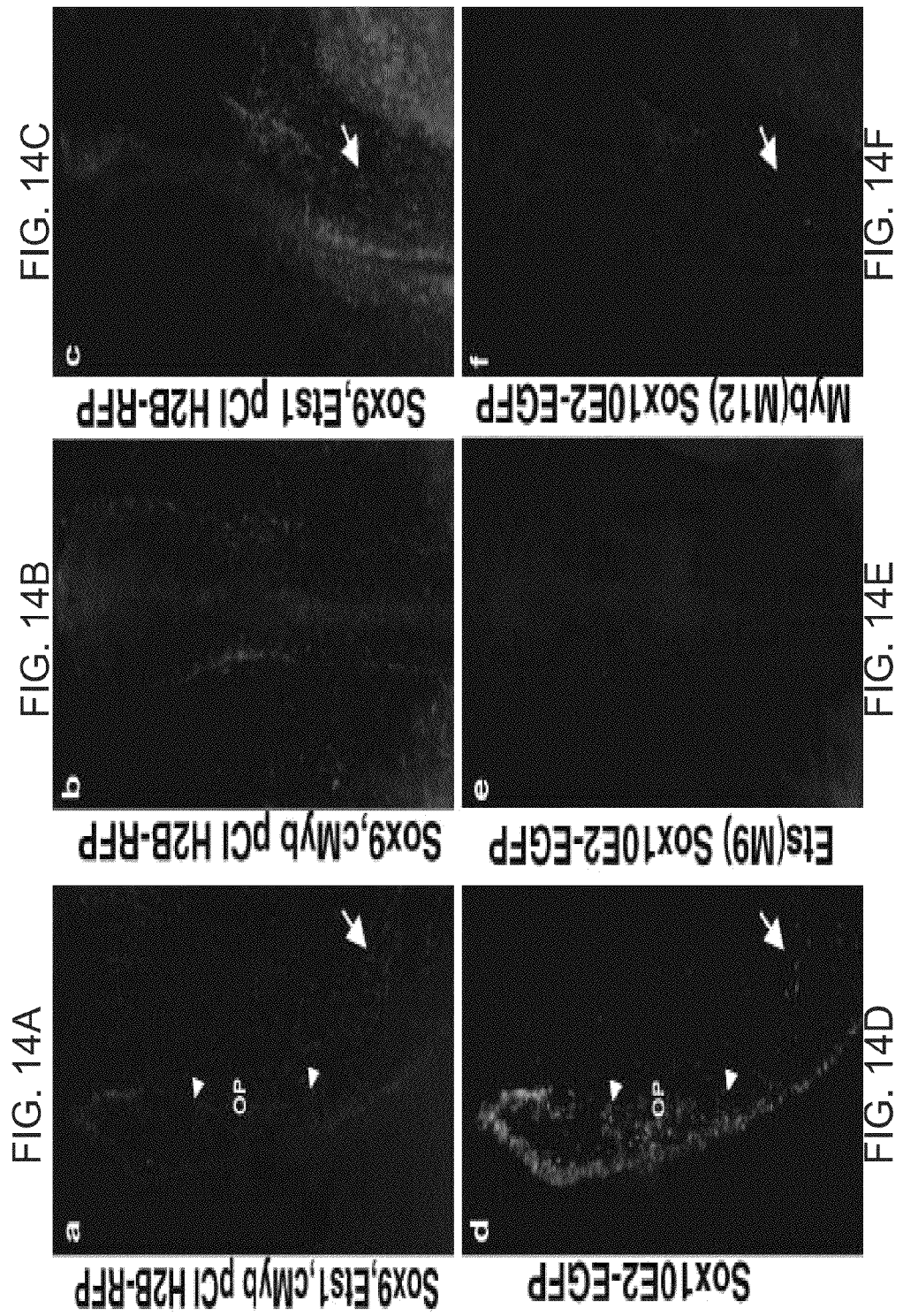

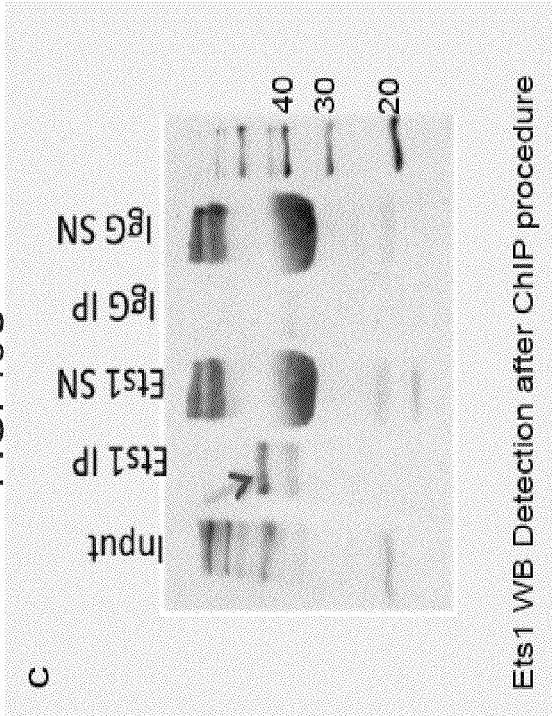
FIG. 15A
FIG. 15C
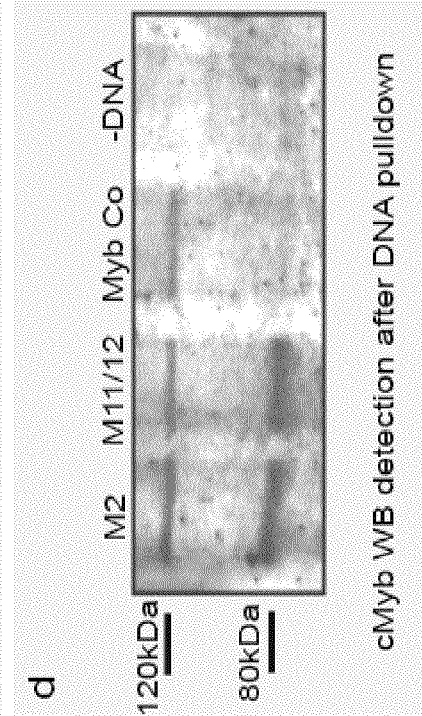
FIG. 15D
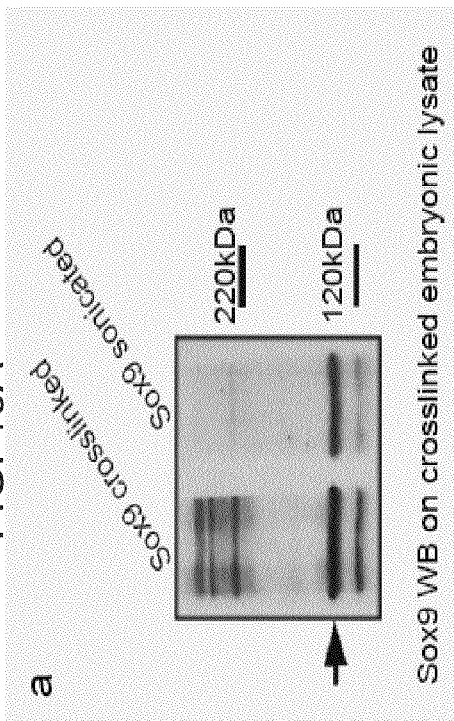
FIG. 15B
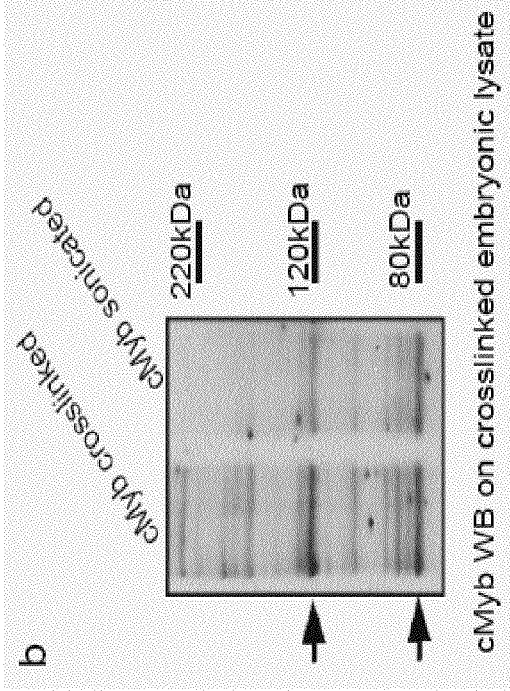

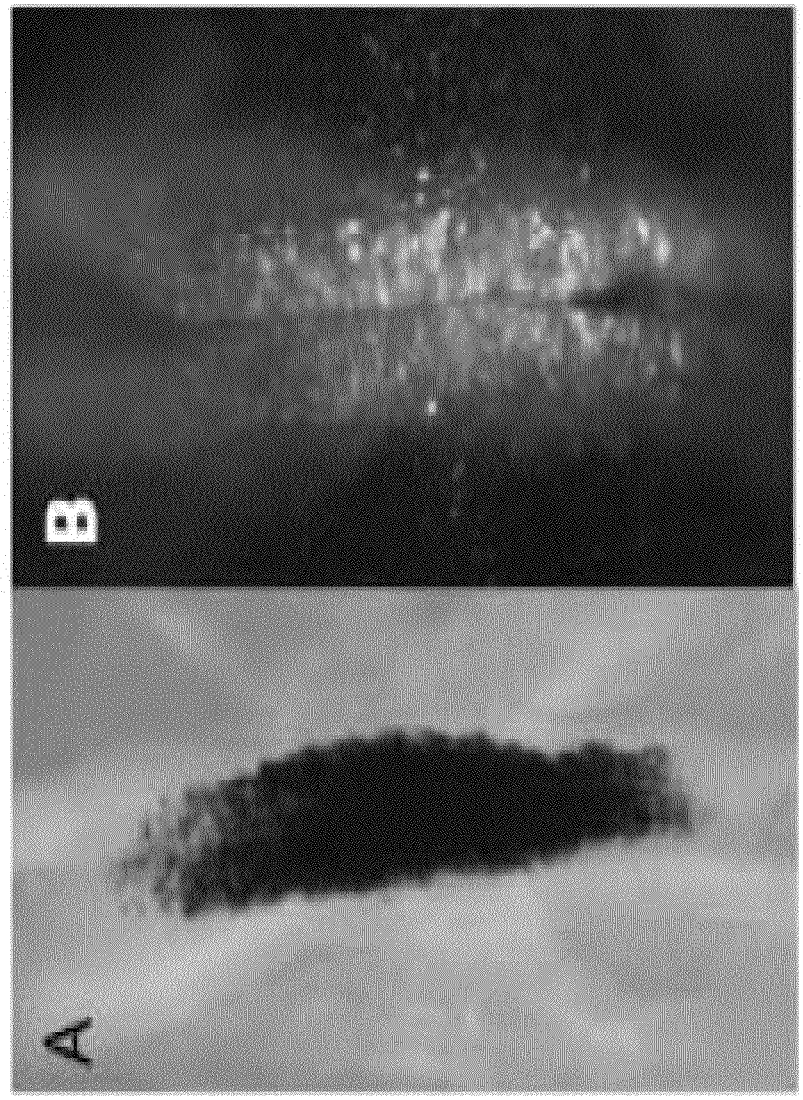

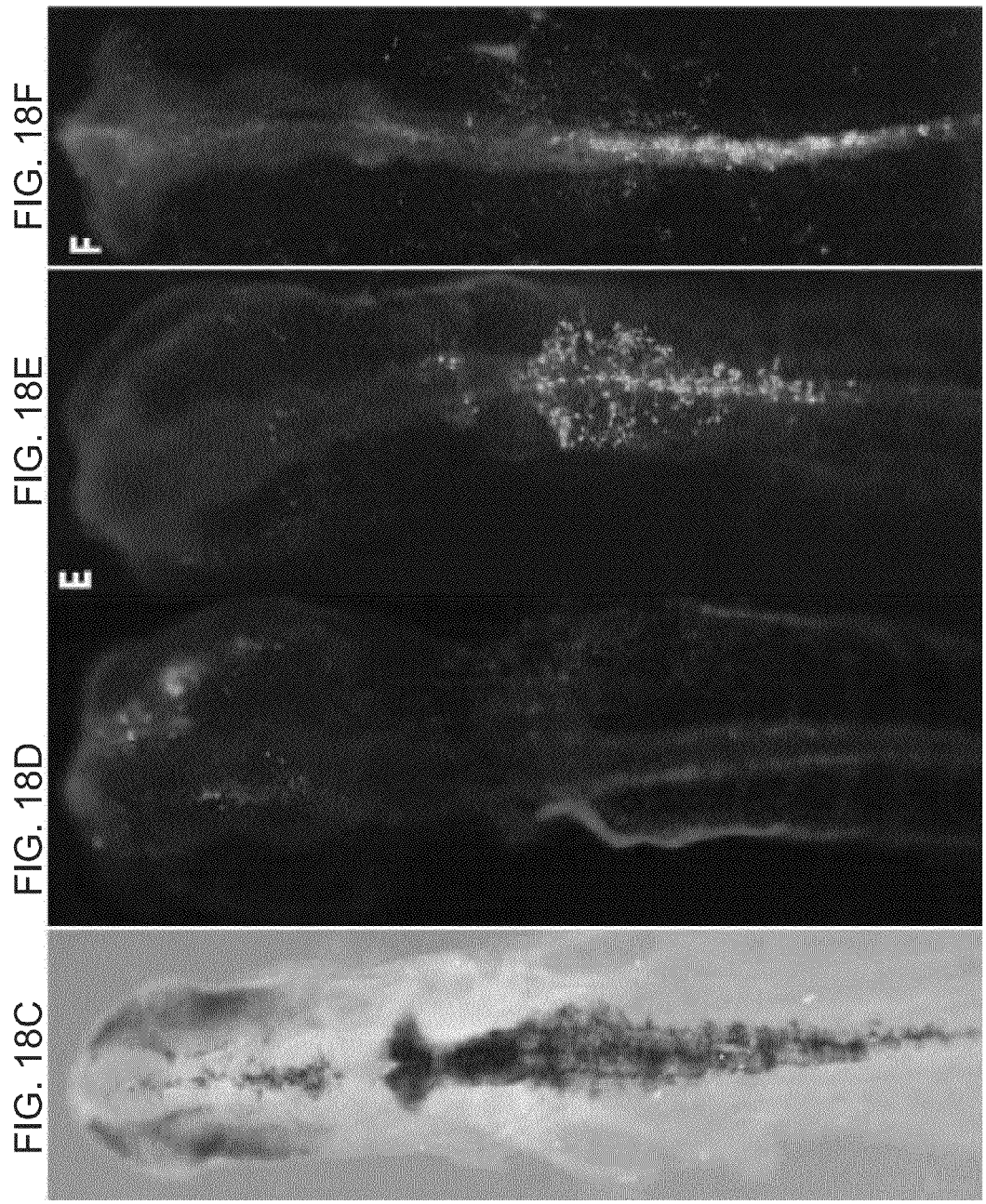

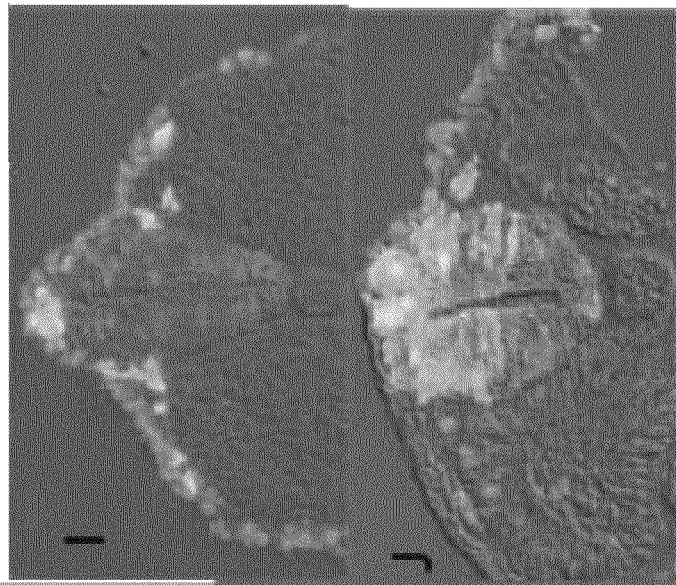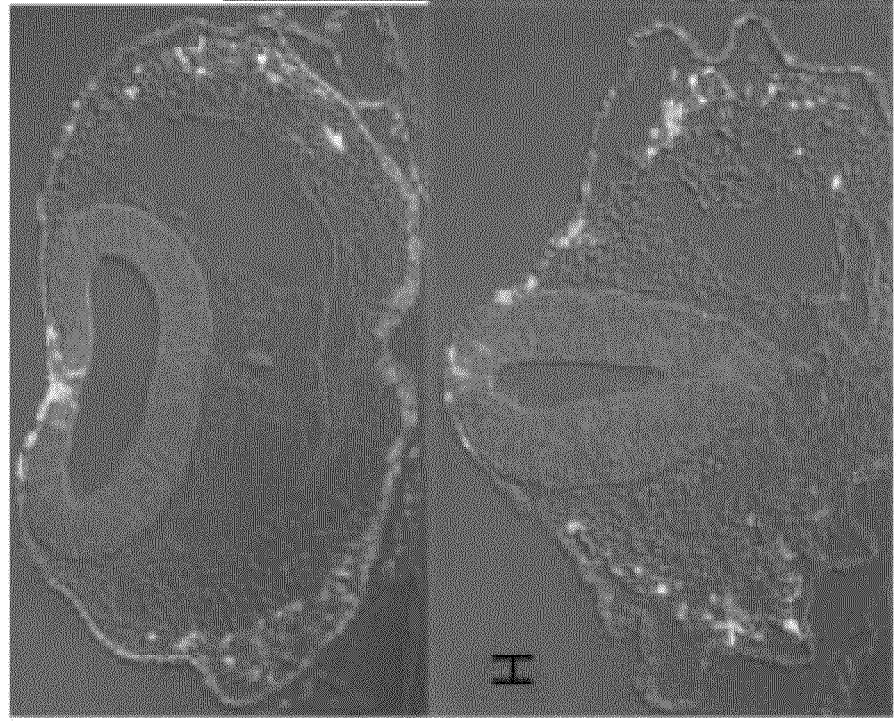

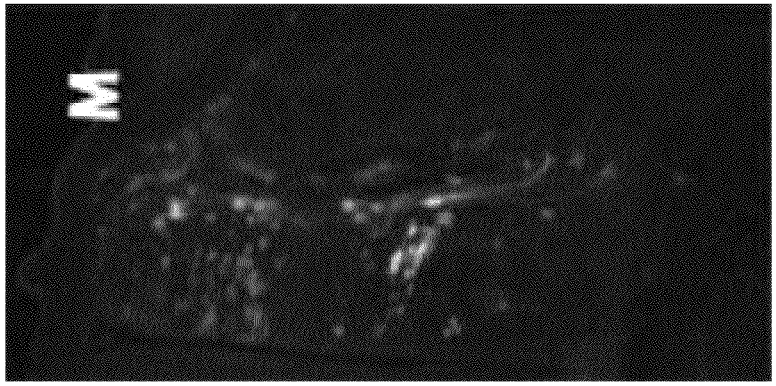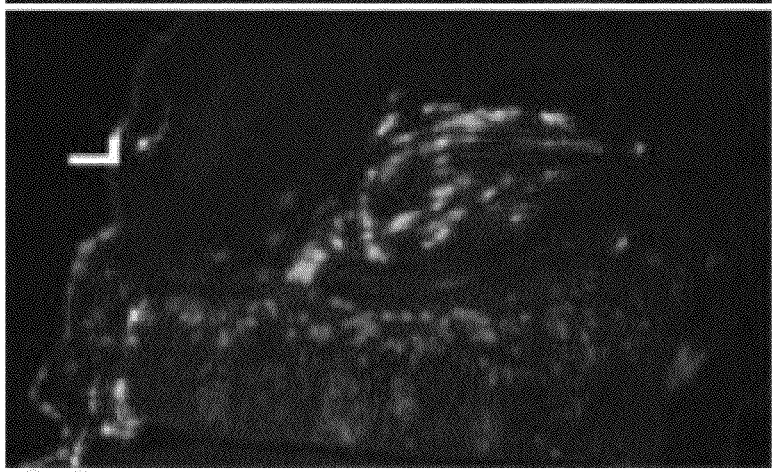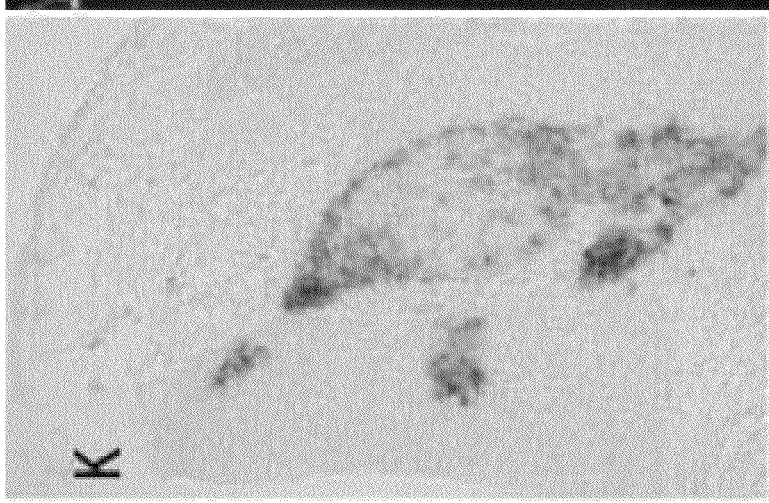

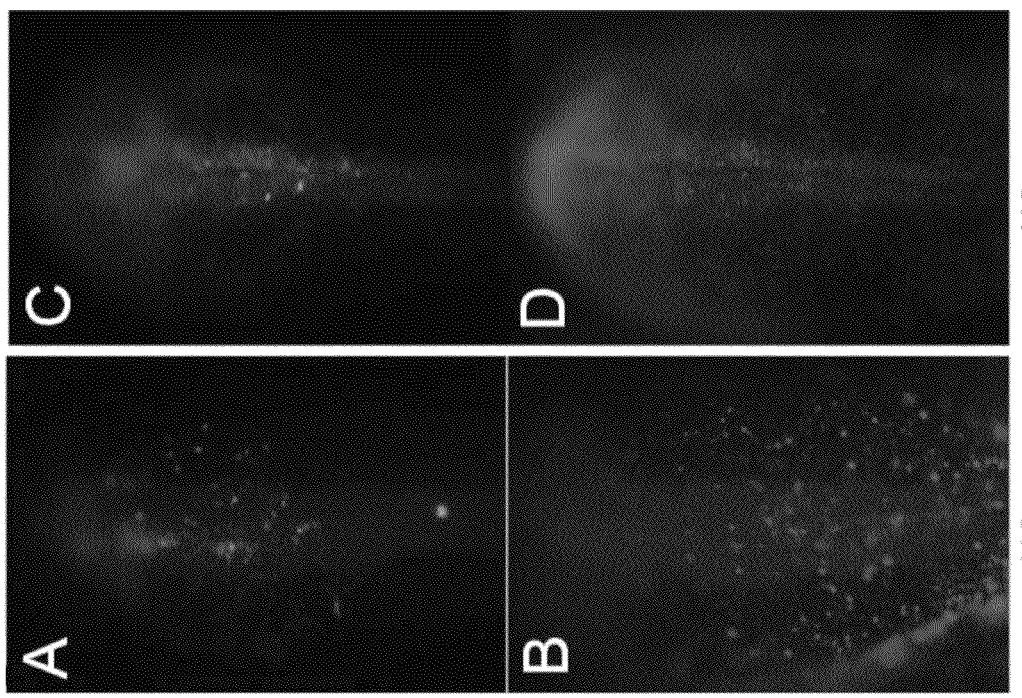

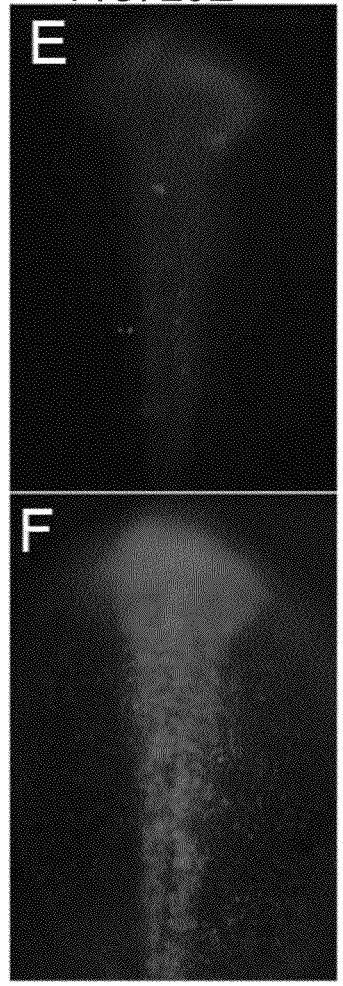
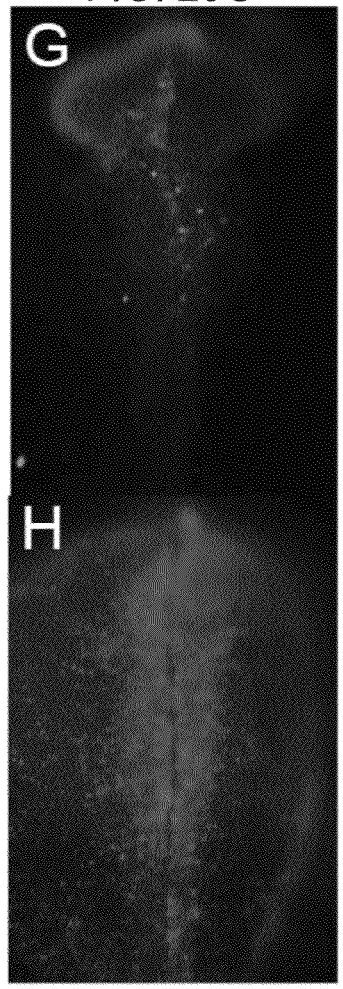
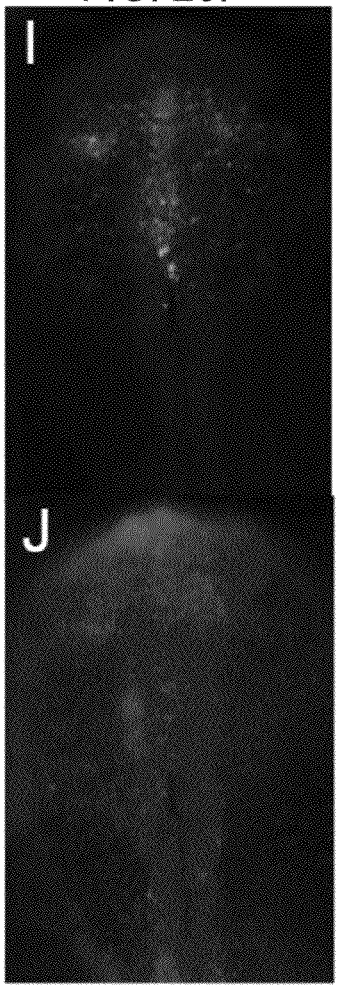
FIG. 20E  FIG. 20G  FIG. 20I
Mut.7  Mut.8  Mut.12
FIG. 20F  FIG. 20H  FIG. 20J

FIG. 21A

Ikaros   Ets/Zeb   HD
CATTAGATATTCCCTGGCCTATTCCTAAGTAATTAGATT
Ets/Gata
TTAACAGGATTTCAACAGATCAGAGCAATCTCTGTGGG FIG. 21B
FIG. 21D
FIG. 21F
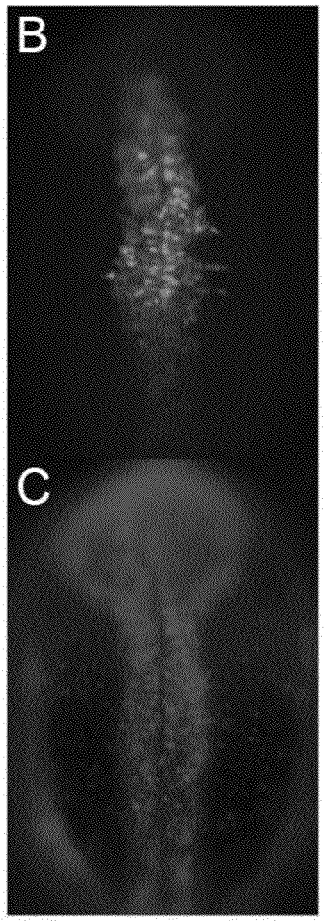
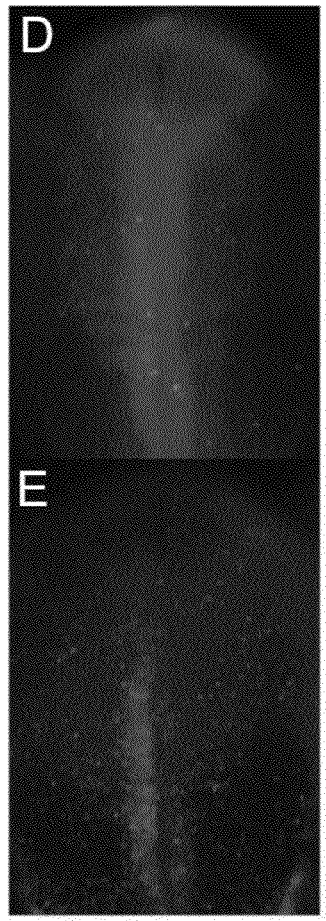
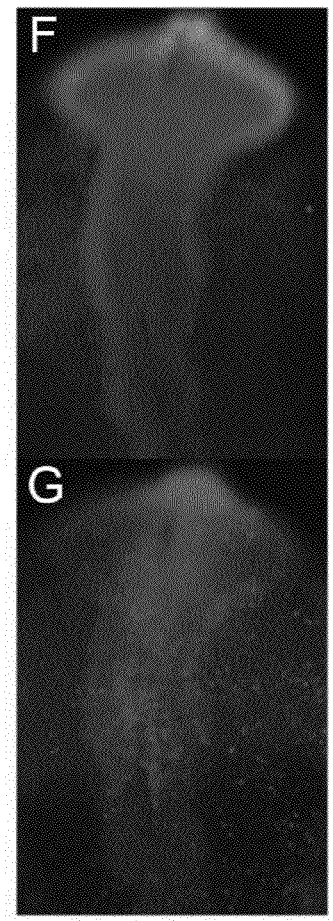
Mut. Ets/Zeb
FIG. 21C
Mut. HD
FIG. 21E
Mut. Ets/Gata
FIG. 21G

FIGURE 23

| Enhancer fragment | Location | Cranial NC | Vagal/Trunk NC | Eye | Otic vesicle | N |
|---|---|---|---|---|---|---|
| NC2 | 0-2099 | + | + | + (weak) | - | 10+ |
| NC2.1 (a) | 0-1361 | - (v weak R4) | + (R5/6 →) | - | - | 7 |
| NC2.2 (b) | 0-792 | - | - | - | - | 7 |
| NC2.3 (c) | 761-2099 | + | + | + (weak) | - | 10+ |
| NC2.4 (ac) | 761-1361 | - | + (weak) | + (weak) | - | 6 |
| NC2.5 (df) | 536-1521 | + (weak) | + | + (weak) | - | 6 |
| NC2.6 (cf) | 761-1521 | + (weak) | + | - | - | 6 |
| NC2.7 (e) | 1192-2099 | - | - | - | + | 5 |
| NC2.8 (eg) | 1192-1840 | - | - | - | + | 5 |
| NC2.9 (cg) | 761-1840 | + (weak) | + | + (weak) | - | 7 |
| NC2.10 (gh) | 958-1840 | + (weak) | + | + (weak) | - | 7 |
| NC | (201-300) | + (weak) | + (weak) | + (weak) | + (weak) | |
| | 304-403 | + (V weak) | + (v weak) | - | + (weak) | |
| | 404-503 | - | - | - | - | |
| | 501-600 | - | - | - | - | |
| | 601-700 | - | -/+ (few weak cells vagal level) | - | - | |
| | 701-800 | + (v weak) | + (weak) | - | - | |
| | 801-900 | + | + | + (weak) | - | |
| | 907-1006 | + | + | + (weak) | - | |
| | 304-333 | + (v weak) | + (weak) | - | + (weak) | 10+ |
| | 334-363 | + (v weak) | + (weak) | - | + | 8 |
| | 364-393 | - | - | - | - | 7 |
| | 394-423 | + (weak) | + | + (weak) | + (weak) | 13 |
| | 424-453 | - | - | - | - | 11 |
| | 454-483 | - | - | - | - | 10+ |
| | 484-513 | - | +(w) (few at R4 v weak) | - | +(weak) | 4 |
| | 514-543 | - | + (weak) and R4 | - | + (weak) | 10+ |
| | 544-573 | - | + (weak) not R4 | + (weak) | + (some) | 6 |
| | 574-603 | - | + (weak) not r4 | +(weak) | +(vweak) | 10+ |
| | 604-633 | - | + (weak) and R4 | + (weak) | - | 7 |
| | 634-663 | - | +(weak) (R4 in some not others) | +(weak) in some embryos | - | 8 |
| | 664-693 | + | + | + | - | 6 |

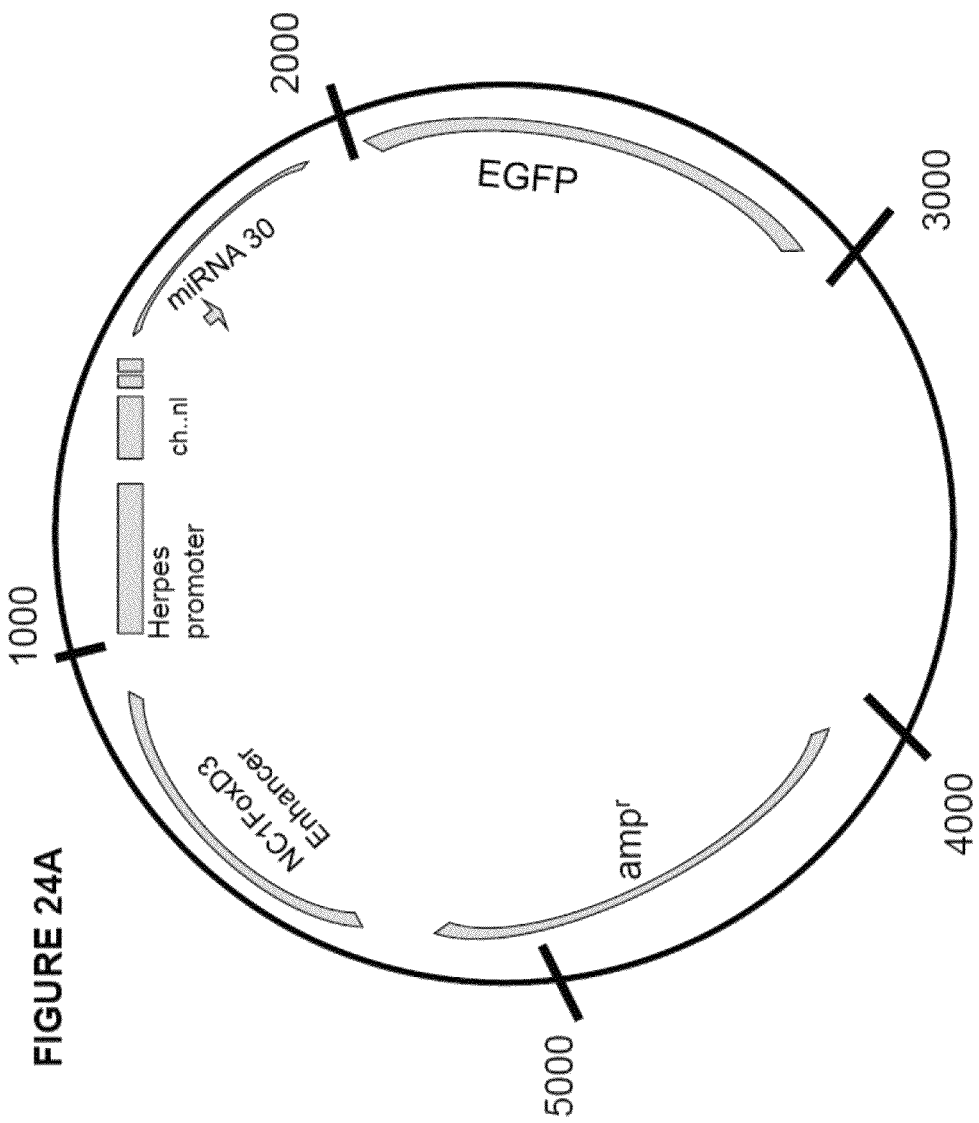

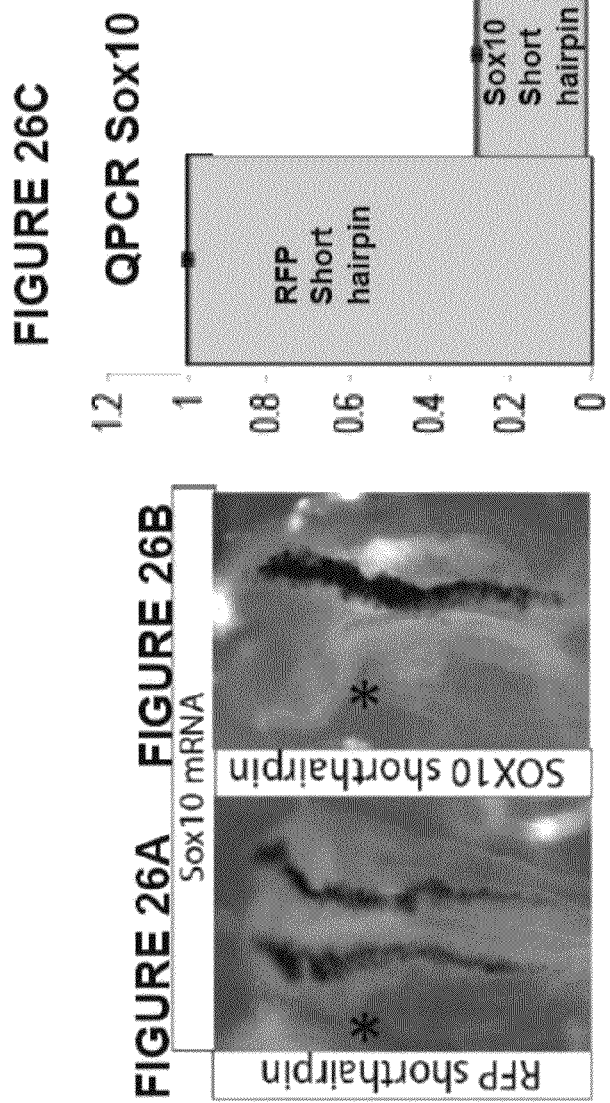

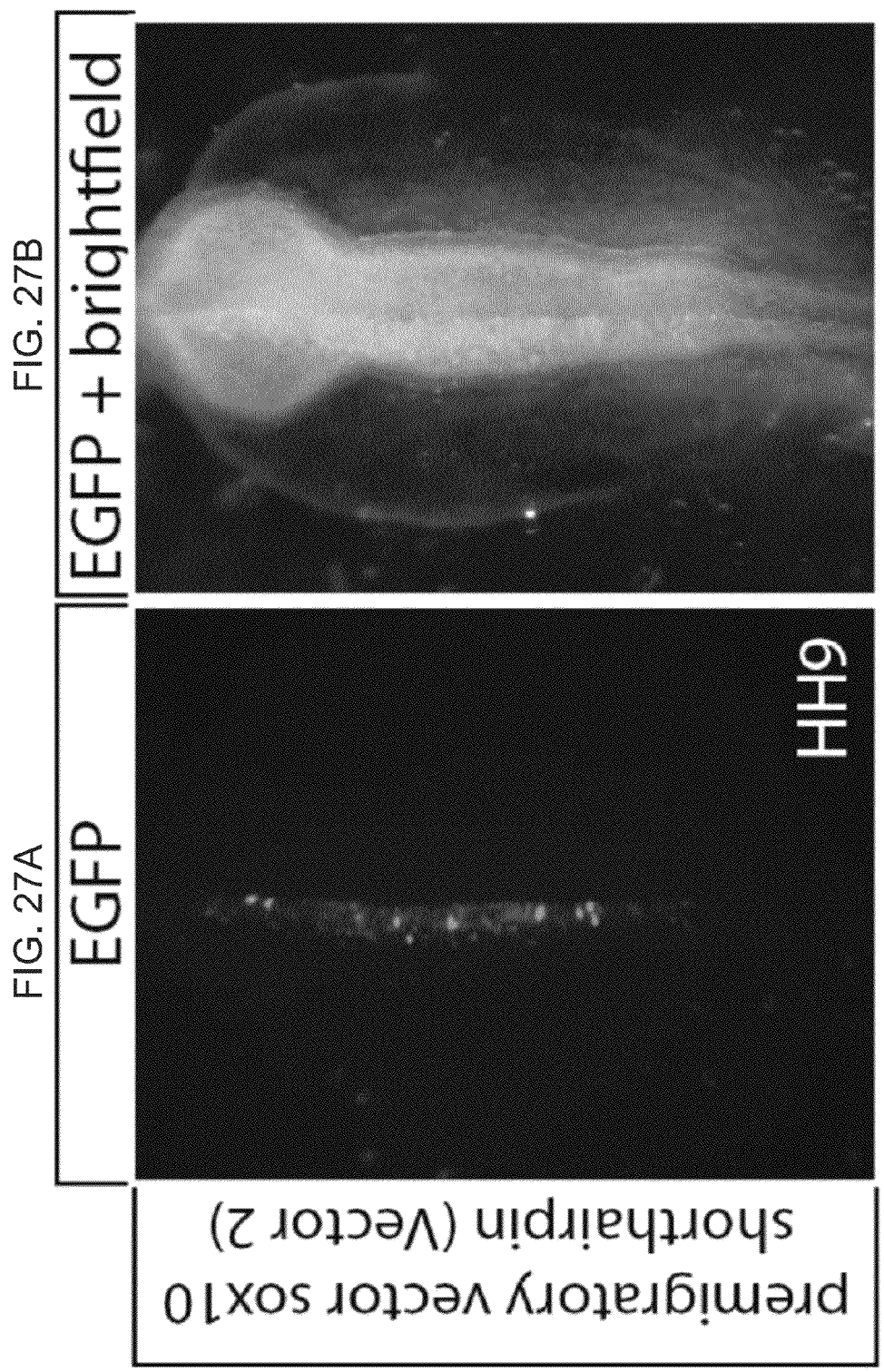

SEQUENCE LISTING

<160> NUMBER OF SEQ ID NOS: 192

<210> SEQ ID NO 1
<211> LENGTH: 2281
<212> TYPE: DNA
<213> ORGANISM: Gallus gallus

<400> SEQUENCE: 1

```
aaaggaatat gtgcagggga tactggcctg cttgagaaca tctctcaagh bgccaatggg      60
aacaagatag gattacactg agcaaaaaac tccacaaaaa tttaaaaaaa tatataggtt     120
ccaaggcttc aaagcaaaag cacgatctat tctgtgagtt tgtgttcact gaacacttaa     180
taggtgagta gaataagcag gagatctagg aaatgcagag cactcagcac actttggatg     240
tggtcctatt agggccaatg gcttaacgac atctaaaaac agtgatgcag atctaaacat     300
ttccgtgcaa aataggactg tgaccactca gtggagagga gaaatctcta ccccgaactg     360
tgggctgtgg gaaaggtcca gatgggaacc actgcactgc tgagcaggtt catatggagg     420
ggataagggg agccatggca gagctagggt aggagagtgg atcacagggg tggaagagag     480
aaagaccatg gtgtgggtga acagaagact ggtagaagaa agtacttaac catacgtacg     540 taccctttctc cagttcttca aacaaagaaa gcaggtgggc tccatatcaa ccattctcca     600
gtggaagggg acgcctcctc tcatccaaga gtgccccac aagtagaaca ccgctggtaa       660 cagagggggtt aagcaatcct ctcgcagcct agcaggagct ggcccagcat ccttccctat     720
ccctttaatc gtatctgata cagatgcaag gctggggagg ggaggcgggc agggaacaaa     780
gaagccattt aaaaaaaaag gaggaaaaaa aaaaaggaca agaaaacgac ccccgcgctc     840
catggcggac gccaaaacga ttgcacaaag gcaccatttc agggctgaaa tttcaccaca     900
ccaacgtgat taaaggattc cacagagggc gggggagaa ggctgaaggc cacagtgctg     960
caaattaacc ttttcttggt aaggatggcc tggatcagga agcacttgtg ttccttgggg    1020
tcaaccccct tcccacacct gcaggcatct ccatatcccc tctgagcttt ttgcccaggg    1080
acccattcaa ctcctgcatt cttgcttccc cctcctgtgc acactgcatc cctgcacaga    1140
ccaacaaagg aagggtggat ggaaggggtgt tcttacaggg agctgtaaaa ggataacata    1200
catggctggt tatatgagct gagttcccag gcaggtgcac acaaactccc gttgggatat    1260
ggatccacac atacagcaca aagaatgcaa gcttcaaaca taagcacaaa ctaggtggaa    1320
```

```
aaatcctccc tgtagctctg caaagagaaa acaacataa agcagaaaca acaggtgcac      1380
tttttaataa gatcacctgc tacagagaga gtgttctgct ccagagctca gagcaagagc      1440
ctaggtgcag agatgattaa gacatgaaaa ccaagcagta gctggctgga aaccctccca      1500
gattataatg catccaccta acttttttgat ttcagcaagg ggctgcattt ttcttttcct      1560
tgcacatcag aagtgagaac gaagggattt taatgggaca aatcacccat ctgtcatcac      1620
actacagatt acagaaaggg actctagaat ttaactattg ctgtgccacc gtaagagctt      1680
ctggtgttca taccagtgag atgccttgag agcacccacg caccaagggc catcagctcc      1740
actgcacatc agagaacagc agcatgagtg gcagagtgg caatttaacc tacaactgct      1800
gagcttgtag gactgtgact ggcgactgtg cttccggctg gggcagtgcc actgaaaggg      1860
gatccccatc actgataagc agcaggagca gggaaacaat aggtgatttg atgagagctg      1920
ctctacgata ctcctgagaa gacccacagc cagctctggc cagagaggaa attgggggtt      1980
tccacagcaa cctgctcagg gcacaaaggc ccaactgtct aggggggaagc aatggaggtg      2040 tctcagcact cctgttttaa gaagggctgg aatctctctg aagccaaagt acctgcaaga      2100
tcagttctgt acaacggccc tttaattggc tgctggtcct ataaccaggg aggagttgtg      2160
gtggaggcag ttactgtact cttaccccta gataaaactt acaggttgct cagttggaaa      2220
aaaagctgta atgaaagcat agcgctcgac tccctaatat taataaatag ggcccaggca      2280
g                                                                      2281

<210> SEQ ID NO 2
<211> LENGTH: 621
<212> TYPE: DNA
<213> ORGANISM: Gallus gallus

<400> SEQUENCE: 2
ggaagagaga aagaccatgg tgtgggtgaa cagaagactg gtagaagaaa gtacttaacc        60
atacgtacgt acccttctcc agttcttcaa acaaagaaag caggtgggct ccatatcaac       120
cattctccag tggaagggga cgcctcctct catccaagag tgcccccaca agtagaacac       180
cgctggtaac agaggggtta agcaatcctc tcgcagccta gcaggagctg gcccagcatc       240
cttccctatc cctttaatcg tatctgatac agatgcaagg ctggggaggg gaggcgggca       300
gggaacaaag aagccattta aaaaaaaagg aggaaaaaaa aaaggacaa gaaaacgacc       360 cccgcgctcc atggcggacg ccaaaacgat tgcacaaagg caccatttca gggctgaaat       420
ttcaccacac caacgtgatt aaaggattcc acagagggcg ggggggagaag gctgaaggcc       480 acagtgctgc aaattaacct tttcttggta aggatggcct ggatcaggaa gcacttgtgt       540 tccttgggt caacccccctt cccacacctg caggcatctc catatcccct ctgagctttt       600
tgcccaggga cccattcaac t                                                621

<210> SEQ ID NO 3
<211> LENGTH: 264
<212> TYPE: DNA
<213> ORGANISM: Gallus gallus

<400> SEQUENCE: 3
ggcaagagtg gcaatttaac ctacaactgc tgagcttgta ggactgtgac tggcgactgt        60
gcttccggct ggggcagtgc cactgaaagg ggatccccat cactgataag cagcaggagc       120
agggaaacaa taggtgattt gatgagagct gctctacgat actcctgaga agacccacag       180
ccagctctgg ccagagagga aattgggggt ttccacagca acctgctcag ggcacaaagg       240
```

```
cccaactgtc tagggggaag caat                                           264
```

<210> SEQ ID NO 4
<211> LENGTH: 888
<212> TYPE: DNA
<213> ORGANISM: Gallus gallus

<400> SEQUENCE: 4

```
aggcaatgca gcgaatgacc ttctctgaga gttttcccac aggccaagcc ctgggctccc    60
tcagcatgta tgtgcttggt gagcttctcc cagcgacctg gtttcactaa cattttctca   120
caaaacaaag aagaaattat cataaacaaa gattacattt ggtttaaagt aagctttcca   180
ccaacactta acctttatga agaaccaaat tattttgttc catgactaag aaaaatctgg   240
cgatatataa ttaaaacaac aaagaagagt cccattctat acaagtgtaa ttacgttcat   300
gtggtatcac tgtaattgaa acacagaaga tgtttcagtc tgtattaaaa gagaatttct   360
ttcagtgggt ttcctgaagc tcattagata ttccctggcc tattctccta agtaattaga   420
ttttaacagg attttcaaca gatcagagca atctctgtgg gtgccaatag gagactctcc   480
ctctggcctt accagcaggg cagcatggat aacatccagg ctgggagtta ataggacaat   540
tactggcctc ttttaaatga gttacattaa tgcacttaag ctaaatggct ctgcatatga   600
ttaaatatta acatctgcaa aatatgaaat catgatatgc aatcaagttt tgttgtttta   660
atttcccaaa tgtcggattt tggtggtgta tgtaaatgtg cattggatag tgtatgttaa   720
actttcaaaa cacagatcaa cactatttgc aaatggttct tttggaacta cttagttaaa   780
catcttaaaa tagcacaagc agagaggaaa ttatcaaaaa tgatataaaa acaagaaaag   840
gaaaaaaaat taaaacttca ttttgaatgt ctcaaaggga gccaggtc                 888
```

<210> SEQ ID NO 5
<211> LENGTH: 2098
<212> TYPE: DNA
<213> ORGANISM: Gallus gallus

<400> SEQUENCE: 5

```
tgagtgtgcc tccatgtgtc gtctgtccgt gaaatggtta aaacttaagg ttacccatcc    60
aaggagtaga aaatgaaggt tctcagtttg atggacaaca gctcagagat ccctgatgtc   120
ccaaaatatt aggtttctct tctaataatg ttggaaatat tgcctactgt catgattaat   180
cttagcagca tctccggctg attgcaggtg acgcagtcac agcgcagtgc ctgtgttggt   240
ttccacacac cgtcaaatct gctacaaatg ccggggtgaa ggggaaagaa ctgtgatacc   300
aggtatccca gtggctaata gattatgaca tgaagaaggg aaaccttttat tttaattcaa   360
aaaacaaaag ccaaatagca aaacttatgt acgtgcctaa ctttttttttc cttcctcaag   420
tggaaaacat tcgcctgcta caactcttg gctggcatca agggaaagtg gaggtatttg    480
cagatgtgga ggaagacata caaaacattt ttcaaatcaa aggcttgaat tattgcactg   540
ggttcatgaa gtttcacagg catgtagaca caccattgtc tgcaccctgg aacaagctgc   600
cctttcttcg ggaaggaaaa acaactcaat gtttcttaca atccgatctg tatgtatcag   660
ggagctatct atattttgga attctttgca ttgtctgtgg taagggtgtg ctgttttggc   720
ccaacaatgg caacattgat tttagaattt cagaattttg gtgcatagaa caaactgtga   780
aacaaaaccg gcctgctctc aatagtacaa caacagtgct cttatataaa cttgcctttc   840
ctatgccatt ttacatagtc aaagatcaat accgctcatt cagccaacat tattaaagcc   900
```

-continued

| | |
|---|---|
| atttatcagc gactttttt tttgttgtta ataaaaggat tttgccgaca aagttatgtc | 960 |
| atcttccgct cacttggtag cagagcagat aattagcttt gttgtctccc caacaattgg | 1020 |
| gccttgttta tgaacttaca tttattaagt gaaagtattt ggaaactgat ggtacattga | 1080 |
| agtttggttg ccatgggcaa taatcatccc aaaaaagtca tgacctccct gttatgcagc | 1140 |
| tagtaactaa ttgaaatgat acaaattact ccgattctct gtctgccaat ttagaggctg | 1200 |
| gttgtggtca agggtcaaat gagctcctat tcatgaaact atgtttgaag tggctgctgc | 1260 |
| catagcaagg ggcttggtgt ggacgcggcg actcctctgg acattacccc atactgtgga | 1320 |
| ggagagtgct gcacagatag caaaacaata agcctaccac cgctaccttc agccgacaca | 1380 |
| tcaaaagctt ctctgtgtca gtcatttagc agtggctgcc tctgaccagg atatgcttta | 1440 |
| ctgggtagag ataagtgttg tattcatccc caagggctac cttacacatt taactgatgc | 1500 |
| tacaatgcct tctgaggtag gtttaagaaa tcaaagtatc tctctgcttg cgctcggttc | 1560 |
| agtaggaaaa acaaagacct cattttcttt gaaaataac acaagaaatt aaaatctgat | 1620 |
| agggcgtctg aagcatcatc cttaaaaaa catccaaaat agttcaactg tgtgctacag | 1680 |
| gaagacagca cgtttatctc agtaaatatg gggacctgag caataaaaag tcagtagtaa | 1740 |
| aatgagagtt tatcctttag gaaattcagt gcaattccaa ggagtgttgc caagggctg | 1800 |
| attaaatttg tgccaaatat actggtttac tgggtgaaca ttcacaatgc cagtaaagag | 1860 |
| atttcttct ttgtgtaagc tcctacagct ttaacatgtc taaatctatt aaaactgtga | 1920 |
| tggaagaaac catgccacat gaacaagtca ggctccttgg ataatgaaga ttaacatttt | 1980 |
| ctatgtttca acattatttg aaagattttc tttgtagttt tagtacagca tgtttcaaca | 2040 |
| aatatttctg tcaacatcaa acgttctgta ggccaaacca accgtgtgct gcaccatc | 2098 |

<210> SEQ ID NO 6
<211> LENGTH: 2479
<212> TYPE: DNA
<213> ORGANISM: Gallus gallus

<400> SEQUENCE: 6

| | |
|---|---|
| tagacaaaga taaccatcct cctcatactt tatgcacaga aatgcaagtt attttccact | 60 |
| ccatttagac ttttcacctt cctttcattt accttgtttt ttacagttca ataaatattt | 120 |
| ttccaagctc cacttgccaa acaaaagagt ttagcttcag tgttactcct ctgacaaata | 180 |
| tccttatggt gttgcacatg tgagccattg ataaacaaat taaaattctg tcccagctca | 240 |
| gagctcagct ggcccatttc atcttgcggt atgggtttgt aaaggtctgg gtgtctgtca | 300 |
| tcctccccta accttgtctt tgtcaagggg atacaaaagc ctgcacgctc ggggccttac | 360 |
| gatactgatt agtgtgagtg acaaagtgga gtagcaagtc cactcagccc ttcataataa | 420 |
| atctatcaaa gagtaataga attccatcaa ttctgcatca tccccgaggg tcgctgtgct | 480 |
| gggatggaaa gtgtgttccg ctgggattgt acaactgtta ttattcaatt acactctttt | 540 |
| cttcctagtt aaagaccatg atatcattat cacttaatga atacatataa ttggatctgg | 600 |
| actctatgtt tggctgatga ataccactca ctattcattc agtctcagct catcttctga | 660 |
| ccatttatta tagactttg gctgaaaacc atgatgacaa agggaatttg aaattagctg | 720 |
| agatttcact caatgctcag ttagacacaa aggcaaaata caattccgac gcctaaatga | 780 |
| ggctgagaac acatggagaa gttgtgccta acttaatagc tgttgatttc tgcacaaacg | 840 |
| caatgaggta aatgcaaaga tatttttcaa ggcagtcccg tgactttgca aacaagcaga | 900 |
| gattttctcc ctttcttccc ccaactttaa tatatatgtg tatatatata tatattgact | 960 |

-continued

```
caaaggtaaa tactgagctg ttaagttggt actttatttc ccaacttagg cacaatatta    1020
gctttaaaga tatcatctga ggccattatg atctttaact cagccctgct aagccaaaca    1080
caattttatg atgaaataac agttaaatct gacaaagcag aagtgctttc tatacagtat    1140
atttattacg cctaatatcg agaccatcat taagtttcat caaacagtgt gcccccaaag    1200
gaaactggcc ctcctattca tattgttggg agtaaatgta gcatacctcc tttggatcac    1260
tggtgaacag gccacctcat taatcctagt tagtagatgc tgctgggcat gtggagcagc    1320
caaatccaga tgctacccac agagcctctc caggcagtta gggaatcaca gagtaccacc    1380
tcaagccctc catacatcac ttcaaattaa atttacatta agtgctactc catcagagct    1440
gagagaagct gacatctttg aaaatgcag atgataatcc attaaatcct attatataca     1500
tgtcttctaa ttttacttaa gctcatgcat accaaagtgt gagtttgtgt taaaaattaa    1560 agacccttt actagaacaa aagactttat gaactgttga ctttgggagg gtttattacg     1620
ggatcaggct attctgtcaa gacaagtaga cttttttttt tttcctgtaa aatttctggt    1680
taatcatttg ttccagggat cttttttcaa atgcacaatg tgtctttgct atttccatct    1740
caaactcttt gttctctcaa atggaagtgc agcctcttta acttaatcaa atgttatgaa    1800
tgaaacagtg ggacacatat tgtctccttt tgcaattaag aaaatatttg ctggcagctc    1860
caaaactggc aacagtaaga agatgctata aaatcatcac agtgaaaaag ctaaggattt    1920
aattgcccta ttatcacata tgttaatccc tttatatttt catagtcctt agtcacagtt    1980
acttctactt tgatgagtct cttctaattt catagcaatg atcttattat ttttgattca    2040
aggcacttaa attttatat ttaaccactg tattttatgt ttatgcttct gtctgattta     2100
cctttctgca agacctatgc taaaatggaa aacatacaat ttcagaagaa ggtaataatt    2160
atttcagata ttaggcaaag catattacca attaaaaaaa ataattaaaa aaaagcatat    2220
caagaaacaa aacacacacg tggtcctaca tacacactat taatttaaaa gctatttatc    2280
aaacctttta aaatttaatc agagtttgga tttcaggcac ttagatttgc tttaactttc    2340
aaatcgtttc tttccaagca tttcactgta tgcctgctat acagtacaca cagtatctat    2400
gtgttagttt ttaaccactg tcattcctca gcaattgaag aagtgatggg acagactgtc    2460
atcaacataa ataagagta                                                 2479
```

<210> SEQ ID NO 7
<211> LENGTH: 556
<212> TYPE: DNA
<213> ORGANISM: Gallus gallus

<400> SEQUENCE: 7

```
cagtaagctt tccaccaaca cttaaccttt atgaagaacc aaattatttt gttccatgac      60
taagaaaaat ctggcgatat ataattaaaa caacaaagaa gagtcccatt ctatacaagt     120
gtaattacgt tcatgtggta tcactgtaat tgaaacacag aagatgtttc agtctgtatt     180
aaaagagaat ttctttcagt gggtttcctg aagctcatta gatattccct ggcctattct     240
cctaagtaat tagattttaa caggattttc aacagatcag agcaatctct gtgggtgcca     300
ataggagact ctccctctgg ccttaccagc agggcagcat ggataacatc caggctggga     360
gttaatagga caattactgg cctcttttaa atgagttaca ttaatgcact taagctaaat     420
ggctctgcat atgattaaat attaacatct gcaaaatatg aaatcatgat atgcaatcaa     480
gttttgttgt tttaatttcc caaatgtcgg attttggtgg tgtatgtaaa tgtgcattgg     540
```

| | |
|---|---|
| atagtgtatg ttaaac | 556 |

<210> SEQ ID NO 8
<211> LENGTH: 304
<212> TYPE: DNA
<213> ORGANISM: Gallus gallus

<400> SEQUENCE: 8

| | |
|---|---|
| cctgaagctc attagatatt ccctggccta ttctcctaag taattagatt ttaacaggat | 60 |
| tttcaacaga tcagagcaat ctctgtgggt gccaatagga gactctccct ctggccttac | 120 |
| cagcagggca gcatggataa catccaggct gggagttaat aggacaatta ctggcctctt | 180 |
| ttaaatgagt tacattaatg cacttaagct aaatggctct gcatatgatt aaatattaac | 240 |
| atctgcaaaa tatgaaatca tgatatgcaa tcaagttttg ttgttttaat ttcccaaatg | 300 |
| tcgg | 304 |

<210> SEQ ID NO 9
<211> LENGTH: 172
<212> TYPE: DNA
<213> ORGANISM: Gallus gallus

<400> SEQUENCE: 9

| | |
|---|---|
| cattagatat ccctggcct attctcctaa gtaattagat tttaacagga ttttcaacag | 60 |
| atcagagcaa tctctgtggg tgccaatagg agactctccc tctggcctta ccagcagggc | 120 |
| agcatggata acatccaggc tgggagttaa taggacaatt actggcctct tt | 172 |

<210> SEQ ID NO 10
<211> LENGTH: 80
<212> TYPE: DNA
<213> ORGANISM: Gallus gallus

<400> SEQUENCE: 10

| | |
|---|---|
| cattagatat ccctggcct attctcctaa gtaattagat tttaacagga ttttcaacag | 60 |
| atcagagcaa tctctgtggg | 80 |

<210> SEQ ID NO 11
<211> LENGTH: 1339
<212> TYPE: DNA
<213> ORGANISM: Gallus gallus

<400> SEQUENCE: 11

| | |
|---|---|
| ggtgcataga acaaactgtg aaacaaaacc ggcctgctct caatagtaca acaacagtgc | 60 |
| tcttatataa acttgccttt cctatgccat tttacatagt caaagatcaa taccgctcat | 120 |
| tcagccaaca ttattaaagc catttatcag cgactttttt ttttgttgtt aataaaagga | 180 |
| ttttgccgac aaagttatgt catcttccgc tcacttggta gcagagcaga taattagctt | 240 |
| tgttgtctcc ccaacaattg ggccttgttt atgaacttac atttattaag tgaaagtatt | 300 |
| tggaaactga tggtacattg aagtttggtt gccatgggca ataatcatcc caaaaaagtc | 360 |
| atgacctccc tgttatgcag ctagtaacta attgaaatga tacaaattac tccgattctc | 420 |
| tgtctgccaa tttagaggct ggttgtggtc aagggtcaaa tgagctccta ttcatgaaac | 480 |
| tatgtttgaa gtggctgctg ccatagcaag gggcttggtg tggacgcggc gactcctctg | 540 |
| gacattaccc catactgtgg aggagagtgc tgcacagata gcaaacaat aagcctacca | 600 |
| ccgctacctt cagccgacac atcaaaagct tctctgtgtc agtcatttag cagtggctgc | 660 |
| ctctgaccag gatatgcttt actgggtaga gataagtgtt gtattcatcc ccaagggcta | 720 |

```
ccttacacat ttaactgatg ctacaatgcc ttctgaggta ggtttaagaa atcaaagtat    780
ctctctgctt gcgctcggtt cagtaggaaa aacaaagacc tcattttctt tgaaaaataa    840
cacaagaaat taaaatctga tagggcgtct gaagcatcat cctttaaaaa acatccaaaa    900
tagttcaact gtgtgctaca ggaagacagc acgtttatct cagtaaatat ggggacctga    960
gcaataaaaa gtcagtagta aaatgagagt ttatccttta ggaaattcag tgcaattcca   1020
aggagtgttg cccaagggct gattaaattt gtgccaaata tactggttta ctgggtgaac   1080
attcacaatg ccagtaaaga gatttctttc tttgtgtaag ctcctacagc tttaacatgt   1140
ctaaatctat taaaactgtg atggaagaaa ccatgccaca tgaacaagtc aggctccttg   1200
gataatgaag attaacattt tctatgtttc aacattattt gaaagatttt ctttgtagtt   1260
ttagtacagc atgtttcaac aaatatttct gtcaacatca acgttctgt aggccaaacc    1320 aaccgtgtgc tgcaccatc                                                 1339

<210> SEQ ID NO 12
<211> LENGTH: 601
<212> TYPE: DNA
<213> ORGANISM: Gallus gallus

<400> SEQUENCE: 12
ggtgcataga acaaactgtg aaacaaaacc ggcctgctct caatagtaca acaacagtgc      60
tcttatataa acttgccttt cctatgccat tttacatagt caaagatcaa taccgctcat     120
tcagccaaca ttattaaagc catttatcag cgacttttt ttttgttgtt aataaaagga      180
ttttgccgac aaagttatgt catcttccgc tcacttggta gcagagcaga taattagctt     240
tgttgtctcc ccaacaattg ggccttgttt atgaacttac atttattaag tgaaagtatt     300
tggaaactga tggtacattg aagtttggtt gccatgggca ataatcatcc caaaaaagtc     360
atgacctccc tgttatgcag ctagtaacta attgaaatga tacaaattac tccgattctc     420
tgtctgccaa tttagaggct ggttgtggtc aagggtcaaa tgagctccta ttcatgaaac     480
tatgtttgaa gtggctgctg ccatagcaag gggcttggtg tggacgcggc gactcctctg     540
gacattaccc catactgtgg aggagagtgc tgcacagata gcaaacaat aagcctacca      600 c                                                                     601

<210> SEQ ID NO 13
<211> LENGTH: 2851
<212> TYPE: DNA
<213> ORGANISM: Gallus gallus
<220> FEATURE:
<221> NAME/KEY: misc_feature
<222> LOCATION: (1944)..(2061)
<223> OTHER INFORMATION: n is a, c, g, or t

<400> SEQUENCE: 13
ttgcaacttg aaaaaccagc gatgtaaagc ctaacgaggt ttctgagacc ctgcaggtgg      60
aaagtttggg atcttggcct ttgcacacca aggacacgat cacactttat tgcacagtct     120
agaaggactg tccatcttgc aaggtgctac caaagctcac agtgctttgg ttaagccctg     180
agggtgtaga gcccggtggt gaaagaggaa cggggcatat aggggccgc atttcatgag      240 cagtggcaga gtgtaggatg ggaaacaggc agagatttgc cctcattatg cctgggtcta     300
acatgtccaa ttaccccatc ctctcctcac ctcctggatg taaagactc ttgttgagag      360 tggccataat tcacagtgaa caccctgcct ccccccttact cccttcacac ccgctgctct    420
```

-continued

```
ccattttcct tccagaaaaa aatatgtctt tgatgaaatg aaatggctca gtcaaagaac      480
ccctcaaatg gttggggacc cctgcacttg gccaccttg cccacttccc agctctattt       540
ctggccgagt ttggagttta agtaggctga ccttgtgccc cggctgccct ggggtcagt       600 gatgaaagcg gatggaggct tcacagtcag gtctcttgtg tgtgactctt ttgttcccgg     660 acagggtgt gcagtgcctg ggacagtgct taattgttca ggggcactgc tttacccgtc       720
atgcccttcc ccgggcggcc ccagcccttc ttgctcatgt gtgggaggga ggcggcttct     780
ccacttgggg tagggaggag gaagcacagt ctgggttgct cggcataatt tctggctgtt     840
tattaatcca tgtaataaat tttagagtgt caggaagcaa aaataaaaat aagaaaaaaa     900 aaaaaagga attcctggca tcattcacaa ttcctgtttg tcactgggtg caccctccct      960
tgtcctgttg cttggtctat ctgtcgtgct tcatggatgc accccggcac caggggttga    1020
gggaaacgag gttgggctta gcctgagagg aggtggtggg cttgtgacag ggagtgcaga    1080
agccttgggt tggagcacac tgataagaca aggtggtggt gtggaaaagt gagtccaaga    1140
ctggaggtgt tgaagctcct ggacaacttt gctaggccca ggctgagcac ccacacctgg    1200
caatgccctg atggcatgca gtgggtttgc ggtaggtatg aaggagaagg atgccgagca    1260
gccttggggg ctgatgataa agagctgaag gctttcagac atccgtggtg gaggtagatg    1320
agcatgtggg aagctttgta ccattcaata cctctttgat gctccctctg catctttctt    1380
tttgcagtga gcccttcccg tgcctcacat cttcattgca gctgcaggct ggggcagaat    1440
actgcatagc aggccgtctc ctctgccgtt tcagtgagtg actgcacaaa ggaaatggat    1500
aaaaggagtg gagggtcaga gtttaattac cctattgtgt gcagagatga gtgatggaca    1560
gagactgtca gtgggtcacc gattagctgc catgaagcag acagaggagg ggaaaatcgt    1620
gatgagcccc caggacagag caatgttggg gacagccaag tgatagtgag acatggagta    1680
ggcagctcag aataggagac ccttttcat tcagttgctc ccccaatcc ttccgctttg      1740 ttcctgcctc cataaggagc cccatgggct ccgaactctc tgctgggccc tgagtgcttc    1800
actggccagg gtgtgagagc tgcttgggtg gtaggacctc tgggggatg tagaataagg     1860 tgagtcattg ccccgactg cactgagctc tcatgtcctg gtgggcgga ggcaaggaaa      1920 gagggaagga aggcaggagg gaannnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn ngagatgagg gtgcttctgg cagagctggt gacctgtttt    2100
tgtgtaagat ggcagaagca acaaatttct gtaactctta ccccttttgc tcccaacccc    2160
tcatcctaca cactgcccag tttccctctc ctacacctc agcaacttga tccactcatc     2220
cccaatcctg ccctcagtcc tgccacacaa tatcacacct agccttcttc caccagtcct    2280 attaccttg tcttaaggct cctctttctt ccccttttc ctacaaaccc tgtatacatc      2340
ctcttaggga ttctggcatc catatttgac ctccaaggtc cagctctcct tgtcccctct    2400
ccctttcacc tctgcttctc cctttcttgc ctttctctcc tcgctcatct tttacctctc    2460
tttcctgtcc ccttcacccc tcatctccca gggctgtttg catgaatcat ctctgaaatc    2520
atgagatcac tgttttttc tggctctctg tcagtgggaa tatcacaata aggagcgtgg    2580
agaagtgacc gggagccatt ggggtgacgc tggcacccc tctcttcact cttcctaccc     2640
ccctcttctt ctgtatcaaa ggaacctttg ttgtccaaaa gcagaaaaag aaaagcagat    2700
aaaaaggcgg aacatgtgat ctcattgatt ttatttagac atccagctaa cccgcctctc    2760
ctttctagat tcatccaaaa ttgtctaagt aagaaaccac aatccatctt caggtttcta    2820
```

```
atttgtgaaa gagatggcgg tgagttgctt t                                  2851
```

<210> SEQ ID NO 14
<211> LENGTH: 2780
<212> TYPE: DNA
<213> ORGANISM: Gallus gallus

<400> SEQUENCE: 14

```
ttccatataa agtcttacat ccacagcttt gtatgcatgt gtgtcagaag cctccttctg     60
tgtcactaag gacgatgtaa agagattgtt tcaagggtct gctcaaataa ttaaggagct    120
gcatgggaga atggtgcaga aagcatggca gatgaggtta gggagtgtac gtcctgttca    180
cctagagcac cagacggact gagatagagc tggaatgaaa ggcagtcaga ggagcaaaga    240
gggtctgtag agaagaagaa aagaaggaag acagaggagg aagatttgct tcaggtaaga    300
atgaagaatt tgtttgtttg tttgtttgtt tgtttgcaga aggtagtgtc agtgaaggat    360
acaccaaagt gctcccaatc caaaaggcag agaatttggc tgggaaattg tttctgttgt    420
ggcagaatgg ccgttatgga agttgcagtg acttcagcat cacgtgaact tttacacatc    480
tatatatatg catgtaaaat gactcagtga agcagtatgt gcaaggagaa ggctatagct    540
agaaggatct ttgtgggaat acttgaggcg taatttaatg ggatgtagga agacatgatg    600
tccatggggt tttgccagag ctctactgta ttgggtattg gcatgtactg ggtgttattg    660
ctgtgggaag cagaggggtt ttgcttagaa aatgaaggct atgttaaact gaggtattct    720
tgactgggag gatgtcaagt gtcagtaggc agcactgagg ggttacactg ctgagaagag    780
aaaaaaattc ttgcagggca tccccatgca caacaggatt tacagcaatg gcttggacat    840
cacaacctct ccaacaacaa gtgttggctt cagcttacaa gatgcaaaat caatagatgt    900
agaggcaaga cagcgacttt tctatctttt taaactaaat gcagtgttcc tgtaaaaatc    960
tagacccatt gtagccacca ctgaaccccct gccagttctg agtccccatc atttgctttt   1020
tctgaaacag gcaccatgac tccattcgta agacatttcc attagcatgt cgggctgatt   1080
caacttatat cctgccctgt tgtgtctgac tcattttttcc ccatctccag gagaagcctg   1140
aaggaaagca gagggcccctt cacatagatg ctcagggtct ctatcagata ataactgaag   1200
aaatatttgc catgaccgtg ctatggtcat ttttttgccat tccttagtca cttggcagcc   1260
aatggaggga agaggcgaga gcagggtggg ggagagtaaa tgagacagag ggacaagaac   1320
aaaagatttc tttgtagtgc agagagagag aaaagggaaa gcatcaccaa atgcccagaa   1380
gccatctttg taacaagaga cctattctct ctgcttcttg gaaaacaagt tggagtaaaa   1440
ggccctggtt gaattaaccc ttcacagagg caactcactg agcatgaagg aaagaggcat   1500
ggccatgaga ggcgtgatct gtgtggtgag gtagtggcac tggcccttaa gcaatttaaa   1560
gcaaggattg gttgtctggg aagaggaggt ggggatgagg ttgggtggtt tgaccatacc   1620
acagatctaa aatgtcagat gtcctttctt cacagacgct ttggttttgg caaagatctt   1680
cagaggggtt tttgcagcat atgaggcaac aaatcttttc catggacatt ttttcttgg    1740
gaggcagaga gaaaggaaaa cattccccct caaaatacac attttactgc aacataatct   1800
tgtccaagaa acctctgtaa attacctcc tgtcactgcc cttcaaaaat tccattcttg    1860
cacactgcat ctctcttatt catgtcttag accttcctt ggctgagcag aacaattta    1920
ttggagttag gggttcccta tagaaatggt aaacaaaagg taaacaaaat cctccatccc   1980
caaagaagca accactgttt ttcatcatga acactctctc ttagttctct tcccaccttc   2040
```

-continued

| | | |
|---|---|---|
| tctaagaaag cttcctctt tactctgtgg acacttttga gtgaaatgag acttcagcaa | 2100 | |
| cgataataca agaaaaaaga tatagccatg gaaagacacg ttgaacctat ttggagatca | 2160 | |
| aacgtgggat atcagtatat gcgagatcat tttgtatctg agcttgctcc aagctctctg | 2220 | |
| ctaattaaaa gaagtgagac agccaggtca gaaataaagg ctttttatct ccatgaaaat | 2280 | |
| acagaaagaa cagcaccctg cttctggagc ctcatcccac agagccaagc aaagagaagc | 2340 | |
| aaaggataga ttggaaatga atacagaacg ggagcagtgt ccagccatgg gtcagccatc | 2400 | |
| cccctgggcg ctgatggggt agataccatg ggtgcccct gagcctgcag tcagttgggc | 2460 | |
| tgcagagcgg atgtgagatg cacacaacat tacgcctgtg ctttcgtaaa ttaccgatca | 2520 | |
| catgggactc gtgcgtctgt gtttgagcag tgctttgaaa acaactagga aattcataca | 2580 | |
| gccacaggac actgcagtat cccggcagtg tcccactccc tggccttctc cctcccttt | 2640 | |
| gcctcctttc tatgtctctc tctgtcttac agggatggta accacaaagg ttggagttga | 2700 | |
| gttttgctcc cactaacttc atcctgggcc ttggggtgtt tgtgttggca cctggtgttg | 2760 | |
| gcatccaacc tacctgtgct | 2780 | |

<210> SEQ ID NO 15
<211> LENGTH: 4039
<212> TYPE: DNA
<213> ORGANISM: Gallus gallus
<220> FEATURE:
<221> NAME/KEY: misc_feature
<222> LOCATION: (403)..(589)
<223> OTHER INFORMATION: n is a, c, g, or t

<400> SEQUENCE: 15

| | | |
|---|---|---|
| cactgtaaac acctttcagg tactggaaca gagtaataag gtctcccctc tacctcctct | 60 | |
| tccccagact aaacagcccc agctccctca gcctttcctc atagggctga ttttccaagc | 120 | |
| ccttcactag ccttgttgcc cttctttgga cctgctccag tacctccatg tccttcttgt | 180 | |
| actgaggtgc ccaaaactga acacagtaca cgaggtgagg cctcaccaat gccgagtaca | 240 | |
| ggggcaggat gacttcccta gttctgctca ccacaccgtt cctgatacaa gccaggatgc | 300 | |
| cattgacctt cttagccacc tgggcacggt gctggctcat attcagaaga ctgtccaaca | 360 | |
| gtacaccaag gtccctttcc atcaggaaga atccaccaca ggnnnnnnnn nnnnnnnnnn | 420 | |
| nnnnnnnnnn nnnnnnnnnn nnnnnnnnnn nnnnnnnnnn nnnnnnnnnn nnnnnnnnnn | 480 | |
| nnnnnnnnnn nnnnnnnnnn nnnnnnnnnn nnnnnnnnnn nnnnnnnnnn nnnnnnnnnn | 540 | |
| nnnnnnnnnn nnnnnnnnnn nnnnnnnnnn nnnnnnnnnn nnnnnnnnnt tcttattctg | 600 | |
| ttccccatct ttatctacca gcacaagggg ctgtgttccc agggagtaac aagtcttatt | 660 | |
| attaaagact gaggcaaaga aggcattaag tacctcagcc ttatccctat ccttggtgac | 720 | |
| gaggttgtcc tcggcatcca acaggggatg gagattctcc ctagccttcc tcttgctgtt | 780 | |
| aatgtgttta tacaagcatt tactgtttac ctttgcttta gtggccaacc tcagttctag | 840 | |
| ctgcgctttg gcttttctaa ttttctccct gcacagcttc actacatacc tgtaatcctc | 900 | |
| tgttgccttc tgcaactgtg atgttagcca cctgtgttag ccctagcgcg agctggccaa | 960 | |
| ttacctggtc aggaccaaat gactgcagat gcacaccaat atgatgagca gcaaaatggc | 1020 | |
| gtctattcac tactaagcac agcttatata cctttactta agctatcatg ccctgtcctg | 1080 | |
| attcgtccgt actggatctt agccccttac cacaattcct tatttggctc ctattgtctc | 1140 | |
| ctcattcctt cgccttctta tcttatttac tttgttagcc aggacagtct gtctgagcac | 1200 | |
| aacagcaccc tttcactatg cttagggaga ggcctatccc gtacagcacg tatccccacc | 1260 | |

```
aagcacctac tacaacaatc ctcataagta gcttgcccgc tcttccagag accataaact    1320
ttccttttgt tcttgagatc cagccaaaat ggctggatgg cttctttttcc gatggctaga   1380
gttcatcaac tgcaaaattt ggtatgttct attgtaggca tgtgcaatgc actggcacag   1440
tgttaccaat caagggataa aattaatatt taacttgaag gcaagattga gccccaaata   1500
aaagaaaatt caaactattt ccaaatagtg tcagcaaatg tctcagcata aaatgtggta   1560
cctggatatt ctgacaaatc agtctgtgtg gggtgacagt gctatcaaat ccctcccctc   1620
cccacttgtt tgagctctgc ttttaaaag aacacaggaa gaaatgcgta gtgatggata   1680
ggagacagcg tggtcctagg gagaagcaga gccccaccgc tttacagagc gagcagagag   1740
tggagcagga gagcggaggg tagcacagca ctgtacagct gcaggctgc tcacaacagg    1800
gcagagcttg tggagaatgt gctctttgtt ccctgccttt aaagggtaag agaaacactt   1860
atgcatggca aattagccca aaatgtatt tctctaaaac acccgattgt ctggccagct    1920
ctgcagctgc agggaagttc caggagaga aggggaggc ggcgggaagg aggaggaga      1980
gggaggcagg gaaggaggat tctgatggct ggggagggg gaaagcaaga tgattgtaca   2040
agcaagggag aaattctcat gcttcaattg aggcacaagc gagtgaagat atcccaatgg   2100
aggagccacc ttggtggtca ggggagagtc cccatggggc tagagaggaa aggggacatg   2160
agacagcaac agctggcagt gttggggcgt cctgacctcc agcaggttca gctgtgccat   2220
ctggactggg atgctccgcg ctggtgccat gctcctcttg tcaccatgtt gtgcatcctg   2280
gggctgactg gatgagtatc ctcttctgag aaacacacac acaggatgta actcaccacg   2340
gaggtgtggg gctcacattc ctctctggag tgcttccatg ctgacacttg gctgtaaaat   2400
gtcccaaata tacccagact ttgcctgggc ttgctatgaa tttccacccc aatgctggta   2460
ctcaattaga aattcacata ccattgctgg tggacaagtg aattccctga tcttcccttg   2520
gtttggggtg caaaactcaa tggtgatttt cccagcaact gcagaagctc ttccagttct   2580
atggactcag aatcaagagc acactgaatt tctccaggca gcatctatca ataaccacat   2640
cttctgaagg ttaggacatg ttcacttggg tgcccagatt ccctagagaa tttctgagct   2700
ctcaaaggag ctgctgtctg ttttctcttt ggagagcaag agaagacttg tgaataggat   2760
caaatctttg aaaagtgggg gcacgctctg tgggaatagc accacagaga caaagaaact   2820
ggagtgagct cagactgtga cagtcctgcc cctgcctcaa gggatgccac tgaaaccaga   2880
gccaggccca ctgccagcat agttgagaac taaatgtcca aggagggtct ctcaccctt    2940
ttgggctgaa ggtttctct ttgtgcctgt gatgaaaatg catttgttct tctgttatcc    3000
atatggaaga actactccct gctgcaaact ttgcaagcac aatctggagg cagtctagtt   3060
atgtctcatt gctacctact gaatgctcct gagagcatct gctgtgtgac ccactcttca   3120
agttggtaat ccagaagtcc tacaaatctt ctcccactgg actggaggaa ggctgaggca   3180
ggcgggcctg gatgtactat gtgaacatat aataccagct gttggtggga attattcatt   3240
caagctgatg acaactctac aatcctgttg tcattaccta gctcatctct gcgtggccca   3300
ctctaccact gctgtattta agagaagagg ggagtgaaaa tcatagaatc acagaatcat   3360
taaggttgga aaagacctgt aaggtcatac agttcaactg acagcccgcc cccaccgtgc   3420
ccactgacca tgtccctcag tgccacatcc acacagttct ggaacacctc cagaggccac   3480
tgccccacc cctccccca cctccctggg cagcctgtgc cactgcagca ctgctctttt    3540
ggagaagaaa ttgttcctaa tattcaacaa gaacctctcc tgataacacg tgagtcctct   3600
```

```
catcctattg ctgttacctg ggagaagagg cagacccca atttgctaca accacctttc    3660
aggtcattgt agagagtggt aaggtctccc cagagcctct tcttatccaa gttacgtgag    3720
tttaagcctc agttcttaag gccacaaagc tacagctgtg tcagcattgg gcctcatggt    3780
atgcagggag tgaatggcac agctcaatgg caggcctgcc actggtcgcc acatcttttg    3840
cagcaaaatg ggacttgggg acaccatgaa tccagacaca gtccagcact ctgtggagac    3900
cctaaggctt tccagggatg tggcatcatc tgagagtggg agtgacaaga gcttagtggc    3960
aaacagtttg ccaagaatga ggatttcagg ggagtgaaag atgcagaccc agttctaatt    4020
caaccagcag ttttagctg                                                 4039
```

```
<210> SEQ ID NO 16
<211> LENGTH: 3015
<212> TYPE: DNA
<213> ORGANISM: Gallus gallus

<400> SEQUENCE: 16
```

```
attagtggta atcatactgt ggcagacaga gttgaaggaa gtcaaggttt catcagcaca      60
ggatgcctgg atggtgctca aacctgggca tgggagaata tgttgtgac ttggatcccc     120 ttgcacctcc ctgagatgct gagagctcct tacagcagag ctcctgcatg tctggatcag     180
cattcccata ggtgacacct ctgggatggt ggatcatcaa tatctatatt gattatatgg     240 atgagggat taagtggccc ctcagtacgt ttgcagacga cacagcattg ggaggaagtg     300
ttcacctgtc tgaggatagg atggccctac agagggatct gggcaggctg gattgatgga     360
ctgaggccaa ttgtgtgagc ttcaaaaaga tcaagtgttg agtcttgcac tttggtcaca     420
acaaccccat gcattgctac aggcttgggg cagagttggc tggaaagata cgtggaggaa     480
aaggatctgg gggtgttctt tgacagctga acatgagcca gcagtgtgtc caggtggcca     540
aaaaggccaa tggcatcctg gcttgtatca gcaatagtgc agccagcagg agcggggagg     600
tgaccgtccc tctgtactca gctctgctga ggctgcacct cgagtgctgt gttcagttct     660
gggcccctca ctgcaagaaa gacatggagg ccctggagtg tgtccagaga agggcagcgg     720
agctgtgagg ggtctggagc acaactctga tggggagcgg ctgagggaac tggggttgtt     780
caggctggag aagagaagct caggggagac ctcatcactc tctatgatga cctgaaaaga     840
ggctgtggct cctaggtaac agtgatagga tgaaaggtaa tggcctcatg ttgcactggg     900
agaggttcag gttggatatt agggaaaatt tcttctccaa aagagcggtg ctgcattggc     960
acaggctgca cagggaggtg atggagtcac cgtccctgga ggtgttccag agccgtgtgg    1020
atgtagcact gaggacgtgg tcagtgggca tggtgggggt gggctggtgg ttggaccagg    1080
tgatctttag aggtctattc caaccaaaag gattctgcga ttctgtgagt cactggagca    1140
gaaatgtggt tgagatatct cacctatcca gtgtcactgt gcttgggata aaaccatcca    1200
ggtagtgacc tgaggagatg aactaactta tagcccagga aaaatgtcac tcatctcaat    1260
atattccact cacttcagta cagctactta cagtgggtt ttcgctgtgc acttctcagc    1320
actgtttgca tcagctcatt tccacaggta gcaacaagca aagtgaagat gagcaaagcc    1380
gtggtggctg cactggtttt gtcatcttgt ttagtcaggg tgacaaaagc aggttcaatc    1440
tcgaggaacg cggagaacag ccctcctcct gcttccctcg cccccacagt cccaatgaat    1500
agagttggca agggtgggca cagccccagc cactggcgct gatggctctc gacgtgaata    1560
agcagcataa aggcacagag cggccccgtc gcggctccgt cccgacccat cctcccagc    1620 tgcagcagca tccgctgcga gaccagaccg gccattccta ccccgtcttt ctgtgtagtt    1680
```

-continued

| | |
|---|---|
| catcttttc tccccctctc atctccccc acctccctct ctctctcttt ctctctccct | 1740 |
| ctctttctct ctctcttttt tttttttttt ttttaattta atcccctttt ttttccgaac | 1800 |
| atatcattac aggagcaaca aaaaagatgg gacaatacag ccattgatga gctgctctcg | 1860 |
| tcctcccgtc ccggtccccc ccactccctc cctcccctcc tctggtgcgt gccaacactc | 1920 |
| tttccacccg cccagggctg gagccagagc caaacaacct ctgctaataa acaagaggaa | 1980 |
| ccagataaac caggaacaca atagagggat ttgttgcact ttagtgatgg tgggaacaat | 2040 |
| gtcaactccg tggcgcagct gcatggaccc cctcccatcc tctcccctca ctgccttgtg | 2100 |
| ccccccgcgc actcgcagcc caacactgtg atttatgaaa ggccagaggt cactttgcat | 2160 |
| taaaggggtc ctttcttgca tcatttatta acccctctac gacaagggt gcttattgtg | 2220 |
| gcggtggtgg cacagggatg gagagggggc ggaggagtcc atcccagagg cactgcacat | 2280 |
| ctcttgtagg atgctgagat gctgagctag tgcttaaatc catttcaca gcaacctgag | 2340 |
| gcacatggga aggaaggaaa gctttagtgg gatgcatttt ggctaccagc tgtgtgccaa | 2400 |
| taaaagcaac ttgtgcaatc cagtgtagat ctgttcccat ttcacacggg tcatcttcca | 2460 |
| cccaacctgt gctcgatgcc gtgctggtga gccgaactca tgtttagtcc tgcagctact | 2520 |
| catgcaccca ggactggcct gaaggattgc cctgcagacc acatcagcca tatggtggtc | 2580 |
| ctgcaggacg aacctgggta tgtcactgca gccttgggac ccttgtgcc agcaggtgtg | 2640 |
| aacctgtagc gcatccaggc agagaggtgg caggttggcc acctcaaaat tcccttctca | 2700 |
| ggccaggata gaggtggtca aaatctctcc ttgccttgtg gaagcaggtt tccatcacag | 2760 |
| gcaatgctgc actgtcacca cgcaatgctt tcaagcctct ctttgtaact gcggagcaaa | 2820 |
| acaatgaaac atggacgtgc taatttgcag gcttggtctt ttgttgcagt gaccacggtc | 2880 |
| actttgggag aactgatgtg gtggcaaagc actgaactct acagtcccct gagctaccca | 2940 |
| catcctcaga tgtgcttatg ggctccttgg agaccctcac cctggccaag cttgctagga | 3000 |
| aagacaaaac ccatc | 3015 |

<210> SEQ ID NO 17
<211> LENGTH: 1782
<212> TYPE: DNA
<213> ORGANISM: Gallus gallus

<400> SEQUENCE: 17

| | |
|---|---|
| accagctgtg tgccaataaa agcaacttgt gcaatccagt gtagatctgt tcccatttca | 60 |
| cacgggtcat cttccaccca acctgtgctc gatgccgtgc tggtgagccg aactcatgtt | 120 |
| tagtcctgca gctactcatg cacccaggac tggcctgaag gattgccctg cagaccacat | 180 |
| cagccatatg gtggtcctgc aggacgaacc tgggtatgtc actgcagcct gggacacct | 240 |
| tgtgccagca ggtgtgaacc tgtagcgcat ccaggcagag aggtggcagg ttggccacct | 300 |
| caaaattccc ttctcaggcc aggatagagg tggtcaaaat ctctccttgc cttgtggaag | 360 |
| caggtttcca tcacaggcaa tgctgcactg tcaccacgca atgctttcaa gcctctcttt | 420 |
| gtaactgcgg agcaaaacaa tgaaacatgg acgtgctaat ttgcaggctt ggtcttttgt | 480 |
| tgcagtgacc acggtcactt tgggagaact gatgtggtgg caaagcactg aactctacag | 540 |
| tcccctgagc tacccacatc ctcagatgtg cttatgggct ccttggagac cctcaccctg | 600 |
| gccaagcttg ctaggaaaga caaaacccat cccttctgat gacctatgg tttggtgcag | 660 |
| gggatacaat ggtgctggtg ggctgaggca tcttcccctct catgaaatag atggggaaca | 720 |

-continued

| | |
|---|---|
| agggacaaaa gaactggaaa ccagtcccca aattagggcc tggtgtgagc cctttgtgta | 780 |
| tgggctcaca gggcagaggg gatgtaaagg ttggggtccc accactcaaa tgccggctgg | 840 |
| tagctctggt taccagccca aatgcttctg ccctggctgt ggtgcctcag cctggggccg | 900 |
| tgctctgtgg ctcgctctcc ctcacattcc tccgggagct gatcagggct tgaatgacac | 960 |
| cccagatgac tccttgctat taattcctgc gaacagaatg ggttccttgt tctcccagtc | 1020 |
| ctactctctg gaggaattac aggggccaag gcagcgggct gaagccttcc tgatttaacc | 1080 |
| cttccccgg ctccccagga gcttcccgc ttccactggg ttgttggagc tgaaagtctt | 1140 |
| cccagagcta cctcggcctc cactgaacga gtccatgagg gtcacccggc accgttacaa | 1200 |
| tcagagaacc cctccagaga gtatccttt ctggtcattc tgcccacatg tatttaggag | 1260 |
| tactcatttc ctttcttctc ccccgggca tccttccttg gtcatgcagt caaagaacgc | 1320 |
| tcagttccct ccattgtatc atgctggaca tggaagattc cacctaagaa agcataaaac | 1380 |
| tttctccccc atctcctcat tccttcagta cttgcttttt gggatttgct ttttggaatt | 1440 |
| acacctggtc tcttggttag gaggtgaggg ggttaatagt ctgccaccca tcaaagcagg | 1500 |
| tagcagacag acctgccagg ccttgctact cttttgatctt ccaggccct ggtaatgcag | 1560 |
| ggaattgtcc cagggacaat gaggacttgc atagcattac cattaccaat tctccacatg | 1620 |
| cttatgaaga actggaccag atgttgggcc aggagctgcc tgggatcttt gcaatgctct | 1680 |
| gaggtgcttg ccctctctgc tttccaggag ggctcctgcc cccccaaggt tgagatttaa | 1740 |
| gaaagcttcc ctagaactct catcttgggg tgatgaaaga ca | 1782 |

<210> SEQ ID NO 18
<211> LENGTH: 3295
<212> TYPE: DNA
<213> ORGANISM: Gallus gallus
<220> FEATURE:
<221> NAME/KEY: misc_feature
<222> LOCATION: (1979)..(2091)
<223> OTHER INFORMATION: n is a, c, g, or t

<400> SEQUENCE: 18

| | |
|---|---|
| atggctcaga tggtcccata ctgccagaat cttgcccttc ccagcctcca cgtttaccac | 60 |
| aggactgagc cgtgtgtctt cccatctatt tcatggtcat ggtgacgagg tgtgagaggg | 120 |
| cctcatgcta cttccacatc aaaggggatg tgcagtgctc actgaggagg ctggacacac | 180 |
| tatttctggc taggggaggg ggatttccag caggcgccaa ccatccccca cgtcctcaac | 240 |
| cctcccacca ttgggttgtc tggtccttct atcctttctc cctcctaagt gaggggatag | 300 |
| agtaaataca tttagatctc cccatagcat ggctttgagg ggctgaagac acacacttcc | 360 |
| aggaggggg tttcctccat tctttattct ccacattcca tcttccattc tccatcctcc | 420 |
| atcttccact ctccatcctc tgtcttccac cctccattct ccattcccca ccgtccatcc | 480 |
| tcctcttcct caccacctgc ctctccactc catccacagt gggaccagca agcctcatcc | 540 |
| ttagcgagga tgccagtgag gatgctcatc ccacccagga gctggggagg gatgagtgct | 600 |
| cagcttcggc acccctctc taccccaccc caggtgccaa cccacaccca cagaaggttg | 660 |
| gaaggacaag accccgggtc ccccatcctc accccaagac ccacgtaccc catgcgtcca | 720 |
| cctccatggg acagggtgct ctccctgctg ctcccagccc gggtctcctc tccgtcctc | 780 |
| gggtctgagg cgagctgggc gctctgaaaa acctttttat gtgcgcgcgc gcgtgtgcgt | 840 |
| gaatcacatg atgccgttc acctgtatcc cgaacaaagg cagcgcactg tttgaggctc | 900 |
| aaacaagcaa gcaggcaagg ggaaggaggg gggtgccagg aaaactgaag gggctgttga | 960 |

```
gagagcgggt gcgcgcggga gaaaatcctt atcaaactcc caattcatgg gtctcccttt    1020
ccctcagcac actgccggta ttgtttgccc gttgtgtgtg tgttttttct ggtgtctgcc    1080 ctgaccccc cattcccagc tctgacgttg ttttgctcta tggaaaggtt tcatggggaa    1140
cccctcccat tttcccaggc agtcctggga caataccagt gctgtgcccc caggctgggc    1200
acaggacaaa agctggccct gtctcgcaga tgggaagctt gctggggtgc ggccatgcca    1260
ggttttaggg gtccctcacc taccagtggc tgagagcaga caccaaaacc tcccagtgga    1320
catcctctgg ccttttttc cccttccaag ctgttatctg tgtttcttct cgcttatttc    1380
ctgtagacag actctcacct cttagtcctc ccttcccacc ggtgcaatca ttcagcaacg    1440
ttcttcccca gcaaactcag tggaggttgt ccttggtgtc ccaccaacat ggtcttcaca    1500
ttgagaccct actgagctgg gtcctgctcc tgtgacgatg cttcatgcac acagcctgga    1560
tgcagaaaca cctacagtgg taggacaaat ctccttccca catcagttct gtctgttgcc    1620
ctcctgacgt gccttttggg tgaagaagtg caccctccaa cctttgcata tcgaggaagc    1680
acagacaata gatttctcca atctgtggtg taggaaggtc gagcttgtga actaactccc    1740
tttactgtta gatccttcat ctgccaaaga ctgtctcttt ttatgggcta cccaatactt    1800
ggagcacctc actgacatag taatataagc ttaaactaag ggaatgaaac ctactatatg    1860
agaacttccc agatccagtc ataaggaaga cttaaaatga tgaagccatg acagcccagt    1920
gattcttgaa acaagagatt tcctctcctc tcctctcctc tccactccac tccactccnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn ngtggattcg    2100
tggaggttgt tctgcccagc ttgctctcct gtgtctctgt tttcatagca caaggaaaga    2160
gatgaatcat ggatggaaga taatttggtc aaggaagcat ggcattgatg ctggattctg    2220
agtgcgttag ctcagatgtt cagcaccatc cttgggattg gttcccttat gtttcaaata    2280
gtgacagaca gggtttctgt ggggtattac attgaattgt agaatcatta aggttggaaa    2340
agacctctga catcacctag tccaactgtc agcctatccc caccatgccc accaaccatg    2400
tccttctgtg ccacatccac atggttcttg aacacttcca gggatggtga gtccaccacc    2460
tccctgggca gcaccgttct ttctaccatt aagattctgg agagtgaaga cctgctacaa    2520
aagctaaaaa tgttcttgaa atcctttgaa cttgttccc tgggtcacag tcattcacct    2580
ccttgcattt tcttgcttcg cgccttcagg ttagatctcc agcaaagacc tggggcagca    2640
ctagatctac ctccttgctg gctcaggagg atctgggaag attgtcagaa tttcatgggt    2700
gatctctcat ggttacagga ttggcactgc tctctgtcat ccccagtgag aagggaaagt    2760
gaagaagcca acaaccacat gcatccggga aggaaggcaa gctagaaaat ggaagaattt    2820
gtgggaacat tttgtaacct gttgtgtgat tagaatctgt acgtgttcca gtgcatgagc    2880
agcaaggagt gaatgactat gagatagtcc tcatatttga gaagacctca tatctgcctt    2940
caggagcaat tcaacacatc caaggaagtt cagcgtggtc atcttggtga gagcccacag    3000
agatggagat gttgtgagga ccccatcttt agagtgcaag agtcctaagt gggttcaagc    3060
tgacatgact tgctctgcac agtgctcttc tggacctaac gtcctccatc ctcaggatgc    3120
tcctgacctc ttgcaacccc ttctccatac tcaggatgct cttttgcag catcttggcc    3180 ccattatcct gggccagatt gttgcagtgc actgggatcc ccaccagact ccgtggtggg    3240
gatcaaggac atgctgggga tgtggatacc acaagcgtgt tggtggtggc ggggg          3295
```

<210> SEQ ID NO 19
<211> LENGTH: 31
<212> TYPE: DNA
<213> ORGANISM: Artificial Sequence
<220> FEATURE:
<223> OTHER INFORMATION: Sox10E1_5'

<400> SEQUENCE: 19
attaggtacc tctgatacag atgcaaggct g                                     31

<210> SEQ ID NO 20
<211> LENGTH: 31
<212> TYPE: DNA
<213> ORGANISM: Artificial Sequence
<220> FEATURE:
<223> OTHER INFORMATION: Sox10E1_3'

<400> SEQUENCE: 20
taatctcgag aatttgcagc actgtggcct t                                     31

<210> SEQ ID NO 21
<211> LENGTH: 31
<212> TYPE: DNA
<213> ORGANISM: Artificial Sequence
<220> FEATURE:
<223> OTHER INFORMATION: Sox10E2_5'

<400> SEQUENCE: 21
aattggtacc ggcaagagtg gcaatttaac c                                     31

<210> SEQ ID NO 22
<211> LENGTH: 31
<212> TYPE: DNA
<213> ORGANISM: Artificial Sequence
<220> FEATURE:
<223> OTHER INFORMATION: Sox10E2_3'

<400> SEQUENCE: 22
attactcgag attgcttccc cctagacagt t                                     31

<210> SEQ ID NO 23
<211> LENGTH: 30
<212> TYPE: DNA
<213> ORGANISM: Artificial Sequence
<220> FEATURE:
<223> OTHER INFORMATION: Sox10E3_5'

<400> SEQUENCE: 23
ttttggtacc taaccaggga ggagttgtgg                                       30

<210> SEQ ID NO 24
<211> LENGTH: 28
<212> TYPE: DNA
<213> ORGANISM: Artificial Sequence
<220> FEATURE:
<223> OTHER INFORMATION: Sox10E3_3'

<400> SEQUENCE: 24
aattctcgag aaggcccaca gcagagtg                                         28

<210> SEQ ID NO 25
<211> LENGTH: 80
<212> TYPE: DNA
<213> ORGANISM: Artificial Sequence
<220> FEATURE:
<223> OTHER INFORMATION: (M1,M3)_5'

```
<400> SEQUENCE: 25
aattggtacc ggcaaagccc atgatttaac ctacaactgc tgagcttgta ggaagcccat      60
gggcgactgt gcttccggct                                                  80

<210> SEQ ID NO 26
<211> LENGTH: 67
<212> TYPE: DNA
<213> ORGANISM: Artificial Sequence
<220> FEATURE:
<223> OTHER INFORMATION: Myb (M2)_5'

<400> SEQUENCE: 26
attaggtacc tggcaagagt ggcaagggat ggactggtag atggaagtgt aggactgtga      60
ctggcga                                                                67

<210> SEQ ID NO 27
<211> LENGTH: 70
<212> TYPE: DNA
<213> ORGANISM: Artificial Sequence
<220> FEATURE:
<223> OTHER INFORMATION: (M5,M7)_3'

<400> SEQUENCE: 27
tccctgctcc tgctgcttat catgggctgg gatccccttt catgggctct gccccagccg      60
gaagcacagt                                                             70

<210> SEQ ID NO 28
<211> LENGTH: 99
<212> TYPE: DNA
<213> ORGANISM: Artificial Sequence
<220> FEATURE:
<223> OTHER INFORMATION: Ets/Elk (M4)_5'

<400> SEQUENCE: 28
attaggtacc tggcaagagt ggcaatttaa cctacaactg ctgagcttgt aggactgtga      60
ctggcgactg tatggttaat tggggcagtg ccactgaaa                             99

<210> SEQ ID NO 29
<211> LENGTH: 47
<212> TYPE: DNA
<213> ORGANISM: Artificial Sequence
<220> FEATURE:
<223> OTHER INFORMATION: NFKB1 (M6)_3'

<400> SEQUENCE: 29
tgctgcttat cagtgatgag cccatggtct cagtggcact gccccag                    47

<210> SEQ ID NO 30
<211> LENGTH: 46
<212> TYPE: DNA
<213> ORGANISM: Artificial Sequence
<220> FEATURE:
<223> OTHER INFORMATION: Lef/Tcf/SoxE (M8)_3'

<400> SEQUENCE: 30
tctcatcaaa tcacctccat ctaccctgct cctgctgctt atcagt                     46

<210> SEQ ID NO 31
<211> LENGTH: 96
<212> TYPE: DNA
<213> ORGANISM: Artificial Sequence
<220> FEATURE:
```

<223> OTHER INFORMATION: Ets (M9)_3

<400> SEQUENCE: 31
aattctcgag attgcttccc cctagacagt tgggcctttg tgccctgagc aggttgctgt        60 ggaaacccccc aatgggctct ctggccagag ctggct        96

<210> SEQ ID NO 32
<211> LENGTH: 90
<212> TYPE: DNA
<213> ORGANISM: Artificial Sequence
<220> FEATURE:
<223> OTHER INFORMATION: NFKB1/Lef/Tcf/Ets1_3'

<400> SEQUENCE: 32
aattctcgag ttgcttcccc ctagacagtt gggcctttgt gccctgagca ggttgctgtg        60
gagcccatgg tcttcctctc tggccagagc        90

<210> SEQ ID NO 33
<211> LENGTH: 65
<212> TYPE: DNA
<213> ORGANISM: Artificial Sequence
<220> FEATURE:
<223> OTHER INFORMATION: SoxE/Lef/Tcf (M10)_3'

<400> SEQUENCE: 33
attactcgag attgcttccc cctagacagt tgggcgtatg cgccctgagc aggttgctgt        60
ggaaa        65

<210> SEQ ID NO 34
<211> LENGTH: 51
<212> TYPE: DNA
<213> ORGANISM: Artificial Sequence
<220> FEATURE:
<223> OTHER INFORMATION: Myb (M11)_3'

<400> SEQUENCE: 34
attactcgag attgcttccc cctactccat aaggcctttg tgccctgagc a        51

<210> SEQ ID NO 35
<211> LENGTH: 35
<212> TYPE: DNA
<213> ORGANISM: Artificial Sequence
<220> FEATURE:
<223> OTHER INFORMATION: SoxD (M12_3'

<400> SEQUENCE: 35
attactcgag gccaattccc cctagacagt tgggc        35

<210> SEQ ID NO 36
<211> LENGTH: 39
<212> TYPE: DNA
<213> ORGANISM: Artificial Sequence
<220> FEATURE:
<223> OTHER INFORMATION: Delta 1_3'

<400> SEQUENCE: 36
aatttcctct ctggccagaa aatcacctat tgtttccct        39

<210> SEQ ID NO 37
<211> LENGTH: 83
<212> TYPE: DNA
<213> ORGANISM: Artificial Sequence
<220> FEATURE:
<223> OTHER INFORMATION: R1_3'

<400> SEQUENCE: 37
aatttcctct ctggccagcc tcggggtaca tccgctcgga ggaggcctcc cagcccatgg    60
tctaaatcac ctattgtttc cct                                           83

<210> SEQ ID NO 38
<211> LENGTH: 100
<212> TYPE: DNA
<213> ORGANISM: Artificial Sequence
<220> FEATURE:
<223> OTHER INFORMATION: EGFP100bp

<400> SEQUENCE: 38
tggagtacaa ctacaacagc cacaacgtct atatcatggc cgacaagcag aagaacggca    60
tcaaggtgaa cttcaagatc cgccacaaca tcgaggacgg                         100

<210> SEQ ID NO 39
<211> LENGTH: 20
<212> TYPE: DNA
<213> ORGANISM: Artificial Sequence
<220> FEATURE:
<223> OTHER INFORMATION: EGFP20bp

<400> SEQUENCE: 39
tggagtacaa ctacaacagc                                               20

<210> SEQ ID NO 40
<211> LENGTH: 30
<212> TYPE: DNA
<213> ORGANISM: Artificial Sequence
<220> FEATURE:
<223> OTHER INFORMATION: EGFP30bp

<400> SEQUENCE: 40
acaagcagaa gaacggcatc aaggtgaact                                    30

<210> SEQ ID NO 41
<211> LENGTH: 20
<212> TYPE: DNA
<213> ORGANISM: Artificial Sequence
<220> FEATURE:
<223> OTHER INFORMATION: NC1 fwd

<400> SEQUENCE: 41
aggcaatgca gcgaatgacc                                               20

<210> SEQ ID NO 42
<211> LENGTH: 20
<212> TYPE: DNA
<213> ORGANISM: Artificial Sequence
<220> FEATURE:
<223> OTHER INFORMATION: NC1 rev

<400> SEQUENCE: 42
gacctggctc cctttgagac                                               20

<210> SEQ ID NO 43
<211> LENGTH: 20
<212> TYPE: DNA
<213> ORGANISM: Artificial Sequence
<220> FEATURE:
<223> OTHER INFORMATION: NC1.1 fwd

<400> SEQUENCE: 43
cagtaagctt tccaccaaca                                              20

<210> SEQ ID NO 44
<211> LENGTH: 22
<212> TYPE: DNA
<213> ORGANISM: Artificial Sequence
<220> FEATURE:
<223> OTHER INFORMATION: NC1.1 rev

<400> SEQUENCE: 44
gtttaacata cactatccaa tg                                           22

<210> SEQ ID NO 45
<211> LENGTH: 20
<212> TYPE: DNA
<213> ORGANISM: Artificial Sequence
<220> FEATURE:
<223> OTHER INFORMATION: NC1.2 fwd

<400> SEQUENCE: 45
cctgaagctc attagatatt                                              20

<210> SEQ ID NO 46
<211> LENGTH: 20
<212> TYPE: DNA
<213> ORGANISM: Artificial Sequence
<220> FEATURE:
<223> OTHER INFORMATION: NC1.2 rev

<400> SEQUENCE: 46
ccgacatttg ggaaattaaa                                              20

<210> SEQ ID NO 47
<211> LENGTH: 17
<212> TYPE: DNA
<213> ORGANISM: Artificial Sequence
<220> FEATURE:
<223> OTHER INFORMATION: NC1.3 fwd

<400> SEQUENCE: 47
cattagatat tccctgg                                                 17

<210> SEQ ID NO 48
<211> LENGTH: 19
<212> TYPE: DNA
<213> ORGANISM: Artificial Sequence
<220> FEATURE:
<223> OTHER INFORMATION: NC1.3 rev

<400> SEQUENCE: 48
aaagaggcca gtaattgtc                                               19

<210> SEQ ID NO 49
<211> LENGTH: 15
<212> TYPE: DNA
<213> ORGANISM: Artificial Sequence
<220> FEATURE:
<223> OTHER INFORMATION: NC1 80bp core fwd

<400> SEQUENCE: 49
cattagatat tccct                                                   15

<210> SEQ ID NO 50
<211> LENGTH: 15
<212> TYPE: DNA
<213> ORGANISM: Artificial Sequence
<220> FEATURE:
<223> OTHER INFORMATION: NCI 80bp core rev

<400> SEQUENCE: 50
cccacagaga ttgct                                             15

<210> SEQ ID NO 51
<211> LENGTH: 69
<212> TYPE: DNA
<213> ORGANISM: Artificial Sequence
<220> FEATURE:
<223> OTHER INFORMATION: NC1.1 Mut 1 fwd

<400> SEQUENCE: 51
caagcagaag aacggcatca aggtgaactt caagatccgc cacaacatcg aggacgggag    60
actctccct                                                    69

<210> SEQ ID NO 52
<211> LENGTH: 74
<212> TYPE: DNA
<213> ORGANISM: Artificial Sequence
<220> FEATURE:
<223> OTHER INFORMATION: NC1.1 Mut 1 rev

<400> SEQUENCE: 52
gatgccgttc ttctgcttgt cggccatgat atagacgttg tggctgttgt agttgtactc    60
caaaacccac tgaa                                              74

<210> SEQ ID NO 53
<211> LENGTH: 72
<212> TYPE: DNA
<213> ORGANISM: Artificial Sequence
<220> FEATURE:
<223> OTHER INFORMATION: NC1.1 Mut 2 fwd

<400> SEQUENCE: 53
caagcagaag aacggcatca aggtgaactt caagatccgc cacaacatcg aggacggact    60
taagctaaat gg                                                72

<210> SEQ ID NO 54
<211> LENGTH: 74
<212> TYPE: DNA
<213> ORGANISM: Artificial Sequence
<220> FEATURE:
<223> OTHER INFORMATION: NC1.1 Mut 2 rev

<400> SEQUENCE: 54
gatgccgttc ttctgcttgt cggccatgat atagacgttg tggctgttgt agttgtactc    60
cactcctatt ggca                                              74

<210> SEQ ID NO 55
<211> LENGTH: 69
<212> TYPE: DNA
<213> ORGANISM: Artificial Sequence
<220> FEATURE:
<223> OTHER INFORMATION: NC1.1 Mut 3 fwd

<400> SEQUENCE: 55
caagcagaag aacggcatca aggtgaactt caagatccgc cacaacatcg aggacggcgg    60
attttggtg                                                    69

<210> SEQ ID NO 56

<211> LENGTH: 77
<212> TYPE: DNA
<213> ORGANISM: Artificial Sequence
<220> FEATURE:
<223> OTHER INFORMATION: NC1.1 Mut 3 rev

<400> SEQUENCE: 56
gatgccgttc ttctgcttgt cggccatgat atagacgttg tggctgttgt agttgtactc        60
cacgattaat gtaactc        77

<210> SEQ ID NO 57
<211> LENGTH: 30
<212> TYPE: DNA
<213> ORGANISM: Artificial Sequence
<220> FEATURE:
<223> OTHER INFORMATION: NC1.1 Mut 4 fwd

<400> SEQUENCE: 57
agtacaacta caacagccat tagatattcc        30

<210> SEQ ID NO 58
<211> LENGTH: 32
<212> TYPE: DNA
<213> ORGANISM: Artificial Sequence
<220> FEATURE:
<223> OTHER INFORMATION: NC1.1 Mut 4 rev

<400> SEQUENCE: 58
tgttgtagtt gtactccaaa gaattctctt tt        32

<210> SEQ ID NO 59
<211> LENGTH: 30
<212> TYPE: DNA
<213> ORGANISM: Artificial Sequence
<220> FEATURE:
<223> OTHER INFORMATION: NC1.1 Mut 5 fwd

<400> SEQUENCE: 59
agtacaacta caacagcatt ctcctaagta        30

<210> SEQ ID NO 60
<211> LENGTH: 30
<212> TYPE: DNA
<213> ORGANISM: Artificial Sequence
<220> FEATURE:
<223> OTHER INFORMATION: NC1.1 Mut 5 rev

<400> SEQUENCE: 60
tgttgtagtt gtactccaag cttcaggaaa        30

<210> SEQ ID NO 61
<211> LENGTH: 30
<212> TYPE: DNA
<213> ORGANISM: Artificial Sequence
<220> FEATURE:
<223> OTHER INFORMATION: NC1.1 Mut 6 fwd

<400> SEQUENCE: 61
agtacaacta caacagctaa caggattttc        30

<210> SEQ ID NO 62
<211> LENGTH: 30
<212> TYPE: DNA
<213> ORGANISM: Artificial Sequence
<220> FEATURE:
<223> OTHER INFORMATION: NC1.1 Mut 6 rev

<400> SEQUENCE: 62
tgttgtagtt gtactccaat aggccaggga                              30

<210> SEQ ID NO 63
<211> LENGTH: 29
<212> TYPE: DNA
<213> ORGANISM: Artificial Sequence
<220> FEATURE:
<223> OTHER INFORMATION: NC1.1 Mut 7 fwd

<400> SEQUENCE: 63
agtacaacta caacagcgag caatctctg                               29

<210> SEQ ID NO 64
<211> LENGTH: 36
<212> TYPE: DNA
<213> ORGANISM: Artificial Sequence
<220> FEATURE:
<223> OTHER INFORMATION: NC1.1 Mut 7 rev

<400> SEQUENCE: 64
tgttgtagtt gtactccata aaatctaatt acttag                       36

<210> SEQ ID NO 65
<211> LENGTH: 29
<212> TYPE: DNA
<213> ORGANISM: Artificial Sequence
<220> FEATURE:
<223> OTHER INFORMATION: NC1.1 Mut 8 fwd

<400> SEQUENCE: 65
agtacaacta caacagcaat aggagactc                               29

<210> SEQ ID NO 66
<211> LENGTH: 31
<212> TYPE: DNA
<213> ORGANISM: Artificial Sequence
<220> FEATURE:
<223> OTHER INFORMATION: NC1.1 Mut 8 rev

<400> SEQUENCE: 66
tgttgtagtt gtactccatg atctgttgaa a                            31

<210> SEQ ID NO 67
<211> LENGTH: 29
<212> TYPE: DNA
<213> ORGANISM: Artificial Sequence
<220> FEATURE:
<223> OTHER INFORMATION: NC1.1 Mut 9 fwd

<400> SEQUENCE: 67
agtacaacta caacagctct ggccttacc                               29

<210> SEQ ID NO 68
<211> LENGTH: 30
<212> TYPE: DNA
<213> ORGANISM: Artificial Sequence
<220> FEATURE:
<223> OTHER INFORMATION: NC1.1 Mut 9 rev

<400> SEQUENCE: 68
tgttgtagtt gtactccacc cacagagatt                              30

<210> SEQ ID NO 69

<211> LENGTH: 29
<212> TYPE: DNA
<213> ORGANISM: Artificial Sequence
<220> FEATURE:
<223> OTHER INFORMATION: NC1.1 Mut10 fwd

<400> SEQUENCE: 69
agtacaacta caacagcagc atggataac                                    29

<210> SEQ ID NO 70
<211> LENGTH: 32
<212> TYPE: DNA
<213> ORGANISM: Artificial Sequence
<220> FEATURE:
<223> OTHER INFORMATION: NC1.1 Mut 10 rev

<400> SEQUENCE: 70
tgttgtagtt gtactccagg gagagtctcc ta                                32

<210> SEQ ID NO 71
<211> LENGTH: 30
<212> TYPE: DNA
<213> ORGANISM: Artificial Sequence
<220> FEATURE:
<223> OTHER INFORMATION: NC1.1 Mut 11 fwd

<400> SEQUENCE: 71
agtacaacta caacagctgg gagttaatag                                   30

<210> SEQ ID NO 72
<211> LENGTH: 31
<212> TYPE: DNA
<213> ORGANISM: Artificial Sequence
<220> FEATURE:
<223> OTHER INFORMATION: NC1.1 Mut 11 rev

<400> SEQUENCE: 72
tgttgtagtt gtactccagc cctgctggta a                                 31

<210> SEQ ID NO 73
<211> LENGTH: 29
<212> TYPE: DNA
<213> ORGANISM: Artificial Sequence
<220> FEATURE:
<223> OTHER INFORMATION: NC1.1 Mut 12 fwd

<400> SEQUENCE: 73
agtacaacta caacagcact ggcctctttt                                   29

<210> SEQ ID NO 74
<211> LENGTH: 30
<212> TYPE: DNA
<213> ORGANISM: Artificial Sequence
<220> FEATURE:
<223> OTHER INFORMATION: NC1.1 Mut 12 rev

<400> SEQUENCE: 74
tgttgtagtt gtactccagc ctggatgtta                                   30

<210> SEQ ID NO 75
<211> LENGTH: 32
<212> TYPE: DNA
<213> ORGANISM: Artificial Sequence
<220> FEATURE:
<223> OTHER INFORMATION: NC1.1 Mut 13 fwd

<400> SEQUENCE: 75
agtacaacta caacagctta cattaatgca ct        32

<210> SEQ ID NO 76
<211> LENGTH: 33
<212> TYPE: DNA
<213> ORGANISM: Artificial Sequence
<220> FEATURE:
<223> OTHER INFORMATION: NC1.1 Mut 13 rev

<400> SEQUENCE: 76
tgttgtagtt gtactccaaa ttgtcctatt aac        33

<210> SEQ ID NO 77
<211> LENGTH: 31
<212> TYPE: DNA
<213> ORGANISM: Artificial Sequence
<220> FEATURE:
<223> OTHER INFORMATION: NC1.1 Mut 14 fwd

<400> SEQUENCE: 77
agtacaacta caacagcact taagctaaat g        31

<210> SEQ ID NO 78
<211> LENGTH: 31
<212> TYPE: DNA
<213> ORGANISM: Artificial Sequence
<220> FEATURE:
<223> OTHER INFORMATION: NC1.1 Mut 14 rev

<400> SEQUENCE: 78
tgttgtagtt gtactccaaa agaggccagt a        31

<210> SEQ ID NO 79
<211> LENGTH: 20
<212> TYPE: DNA
<213> ORGANISM: Artificial Sequence
<220> FEATURE:
<223> OTHER INFORMATION: NC2 fwd

<400> SEQUENCE: 79
tgagtgtgcc tccatgtgtc        20

<210> SEQ ID NO 80
<211> LENGTH: 20
<212> TYPE: DNA
<213> ORGANISM: Artificial Sequence
<220> FEATURE:
<223> OTHER INFORMATION: NC2 rev

<400> SEQUENCE: 80
gatggtgcag cacacggttg        20

<210> SEQ ID NO 81
<211> LENGTH: 23
<212> TYPE: DNA
<213> ORGANISM: Artificial Sequence
<220> FEATURE:
<223> OTHER INFORMATION: NC2.1/NC2.4 rev

<400> SEQUENCE: 81
tgtggtaggc ttattgtttt gct        23

<210> SEQ ID NO 82
<211> LENGTH: 21
<212> TYPE: DNA

```
<213> ORGANISM: Artificial Sequence
<220> FEATURE:
<223> OTHER INFORMATION: NC2.2 rev

<400> SEQUENCE: 82
tcggttttgt ttcacagttt g                                              21

<210> SEQ ID NO 83
<211> LENGTH: 20
<212> TYPE: DNA
<213> ORGANISM: Artificial Sequence
<220> FEATURE:
<223> OTHER INFORMATION: NC2.3/NC2.4/NC2.6/NC2.9 fwd

<400> SEQUENCE: 83
ggtgcataga acaaactgtg                                                20

<210> SEQ ID NO 84
<211> LENGTH: 21
<212> TYPE: DNA
<213> ORGANISM: Artificial Sequence
<220> FEATURE:
<223> OTHER INFORMATION: NC2.5 fwd

<400> SEQUENCE: 84
gcactgggtt catgaagttt c                                              21

<210> SEQ ID NO 85
<211> LENGTH: 20
<212> TYPE: DNA
<213> ORGANISM: Artificial Sequence
<220> FEATURE:
<223> OTHER INFORMATION: NC2.5 rev

<400> SEQUENCE: 85
ctacctcaga aggcattgta                                                20

<210> SEQ ID NO 86
<211> LENGTH: 21
<212> TYPE: DNA
<213> ORGANISM: Artificial Sequence
<220> FEATURE:
<223> OTHER INFORMATION: NC2.7/NC2.8 fwd

<400> SEQUENCE: 86
cgattctctg tctgccaatt t                                              21

<210> SEQ ID NO 87
<211> LENGTH: 20
<212> TYPE: DNA
<213> ORGANISM: Artificial Sequence
<220> FEATURE:
<223> OTHER INFORMATION: NC2.8/NC2.9/NC2.10 rev

<400> SEQUENCE: 87
gttcacccag taaaccagta                                                20

<210> SEQ ID NO 88
<211> LENGTH: 19
<212> TYPE: DNA
<213> ORGANISM: Artificial Sequence
<220> FEATURE:
<223> OTHER INFORMATION: NC2.10 fwd

<400> SEQUENCE: 88
tgtcatcttc cgctcactt                                                 19
```

<210> SEQ ID NO 89
<211> LENGTH: 69
<212> TYPE: DNA
<213> ORGANISM: Artificial Sequence
<220> FEATURE:
<223> OTHER INFORMATION: NC2.9 Mut 1 fwd

<400> SEQUENCE: 89
caagcagaag aacggcatca aggtgaactt caagatccgc cacaacatcg aggacgggga    60
aactgatgg                                                            69

<210> SEQ ID NO 90
<211> LENGTH: 76
<212> TYPE: DNA
<213> ORGANISM: Artificial Sequence
<220> FEATURE:
<223> OTHER INFORMATION: NC2.9 Mut 1 rev

<400> SEQUENCE: 90
gatgccgttc ttctgcttgt cggccatgat atagacgttg tggctgttgt agttgtactc    60
cagacataac tttgtc                                                    76

<210> SEQ ID NO 91
<211> LENGTH: 71
<212> TYPE: DNA
<213> ORGANISM: Artificial Sequence
<220> FEATURE:
<223> OTHER INFORMATION: NC2.9 Mut 2 fwd

<400> SEQUENCE: 91
caagcagaag aacggcatca aggtgaactt caagatccgc cacaacatcg aggacggaaa    60
ttactccgat t                                                         71

<210> SEQ ID NO 92
<211> LENGTH: 77
<212> TYPE: DNA
<213> ORGANISM: Artificial Sequence
<220> FEATURE:
<223> OTHER INFORMATION: NC2.9 Mut 2 rev

<400> SEQUENCE: 92
gatgccgttc ttctgcttgt cggccatgat atagacgttg tggctgttgt agttgtactc    60
caccaaatac tttcact                                                   77

<210> SEQ ID NO 93
<211> LENGTH: 70
<212> TYPE: DNA
<213> ORGANISM: Artificial Sequence
<220> FEATURE:
<223> OTHER INFORMATION: NC2.9 Mut 3 fwd

<400> SEQUENCE: 93
caagcagaag aacggcatca aggtgaactt caagatccgc cacaacatcg aggacggtag    60
caagggctt                                                            70

<210> SEQ ID NO 94
<211> LENGTH: 78
<212> TYPE: DNA
<213> ORGANISM: Artificial Sequence
<220> FEATURE:
<223> OTHER INFORMATION: NC2.9 Mut 3 rev

```
<400> SEQUENCE: 94
gatgccgttc ttctgcttgt cggccatgat atagacgttg tggctgttgt agttgtactc    60
cagtatcatt tcaattag                                                  78

<210> SEQ ID NO 95
<211> LENGTH: 69
<212> TYPE: DNA
<213> ORGANISM: Artificial Sequence
<220> FEATURE:
<223> OTHER INFORMATION: NC2.9 Mut 4 fwd

<400> SEQUENCE: 95
caagcagaag aacggcatca aggtgaactt caagatccgc cacaacatcg aggacggccg    60
ctaccttca                                                            69

<210> SEQ ID NO 96
<211> LENGTH: 74
<212> TYPE: DNA
<213> ORGANISM: Artificial Sequence
<220> FEATURE:
<223> OTHER INFORMATION: NC2.9 Mut 4 rev

<400> SEQUENCE: 96
gatgccgttc ttctgcttgt cggccatgat atagacgttg tggctgttgt agttgtactc    60
cacagcagcc actt                                                      74

<210> SEQ ID NO 97
<211> LENGTH: 71
<212> TYPE: DNA
<213> ORGANISM: Artificial Sequence
<220> FEATURE:
<223> OTHER INFORMATION: NC2.9 Mut 5 fwd

<400> SEQUENCE: 97
caagcagaag aacggcatca aggtgaactt caagatccgc cacaacatcg aggacgggta    60
ttcatcccca a                                                         71

<210> SEQ ID NO 98
<211> LENGTH: 74
<212> TYPE: DNA
<213> ORGANISM: Artificial Sequence
<220> FEATURE:
<223> OTHER INFORMATION: NC2.9 Mut 5 rev

<400> SEQUENCE: 98
gatgccgttc ttctgcttgt cggccatgat atagacgttg tggctgttgt agttgtactc    60
catggtaggc ttat                                                      74

<210> SEQ ID NO 99
<211> LENGTH: 70
<212> TYPE: DNA
<213> ORGANISM: Artificial Sequence
<220> FEATURE:
<223> OTHER INFORMATION: NC2.9 Mut 6 fwd

<400> SEQUENCE: 99
caagcagaag aacggcatca aggtgaactt caagatccgc cacaacatcg aggacggcag    60
taggaaaaac                                                           70

<210> SEQ ID NO 100
<211> LENGTH: 77
```

```
<212> TYPE: DNA
<213> ORGANISM: Artificial Sequence
<220> FEATURE:
<223> OTHER INFORMATION: NC2.9 Mut 6 rev

<400> SEQUENCE: 100
gatgccgttc ttctgcttgt cggccatgat atagacgttg tggctgttgt agttgtactc      60
caaacactta tctctac                                                    77

<210> SEQ ID NO 101
<211> LENGTH: 71
<212> TYPE: DNA
<213> ORGANISM: Artificial Sequence
<220> FEATURE:
<223> OTHER INFORMATION: NC2.9 Mut 7 fwd

<400> SEQUENCE: 101
caagcagaag aacggcatca aggtgaactt caagatccgc cacaacatcg aggacggtag      60
ttcaactgtg t                                                          71

<210> SEQ ID NO 102
<211> LENGTH: 74
<212> TYPE: DNA
<213> ORGANISM: Artificial Sequence
<220> FEATURE:
<223> OTHER INFORMATION: NC2.9 Mut 7 rev

<400> SEQUENCE: 102
gatgccgttc ttctgcttgt cggccatgat atagacgttg tggctgttgt agttgtactc      60
caaaccgagc gcaa                                                       74

<210> SEQ ID NO 103
<211> LENGTH: 69
<212> TYPE: DNA
<213> ORGANISM: Artificial Sequence
<220> FEATURE:
<223> OTHER INFORMATION: NC2.9 Mut 8 fwd

<400> SEQUENCE: 103
caagcagaag aacggcatca aggtgaactt caagatccgc cacaacatcg aggacggtca      60
gtgcaattc                                                             69

<210> SEQ ID NO 104
<211> LENGTH: 76
<212> TYPE: DNA
<213> ORGANISM: Artificial Sequence
<220> FEATURE:
<223> OTHER INFORMATION: NC2.9 Mut 8 rev

<400> SEQUENCE: 104
gatgccgttc ttctgcttgt cggccatgat atagacgttg tggctgttgt agttgtactc      60
cagaactatt ttggat                                                     76

<210> SEQ ID NO 105
<211> LENGTH: 35
<212> TYPE: DNA
<213> ORGANISM: Artificial Sequence
<220> FEATURE:
<223> OTHER INFORMATION: NC2.9 Mut 9 fwd

<400> SEQUENCE: 105
gaagaacggc atcaaggtga actatgggca ataat                                35
```

<210> SEQ ID NO 106
<211> LENGTH: 35
<212> TYPE: DNA
<213> ORGANISM: Artificial Sequence
<220> FEATURE:
<223> OTHER INFORMATION: NC2.9 Mut 9 rev

<400> SEQUENCE: 106
ttgatgccgt tcttctgctt gtccaaatac tttca                    35

<210> SEQ ID NO 107
<211> LENGTH: 35
<212> TYPE: DNA
<213> ORGANISM: Artificial Sequence
<220> FEATURE:
<223> OTHER INFORMATION: NC2.9 Mut 10 fwd

<400> SEQUENCE: 107
gaagaacggc atcaaggtga actacctccc tgtta                    35

<210> SEQ ID NO 108
<211> LENGTH: 34
<212> TYPE: DNA
<213> ORGANISM: Artificial Sequence
<220> FEATURE:
<223> OTHER INFORMATION: NC2.9 Mut 10 rev

<400> SEQUENCE: 108
ttgatgccgt tcttctgctt gtggcaacca aact                     34

<210> SEQ ID NO 109
<211> LENGTH: 37
<212> TYPE: DNA
<213> ORGANISM: Artificial Sequence
<220> FEATURE:
<223> OTHER INFORMATION: NC2.9 Mut 11 fwd

<400> SEQUENCE: 109
gaagaacggc atcaaggtga actgaaatga tacaaat                  37

<210> SEQ ID NO 110
<211> LENGTH: 35
<212> TYPE: DNA
<213> ORGANISM: Artificial Sequence
<220> FEATURE:
<223> OTHER INFORMATION: NC2.9 Mut 11 rev

<400> SEQUENCE: 110
ttgatgccgt tcttctgctt gtcatgactt ttttg                    35

<210> SEQ ID NO 111
<211> LENGTH: 35
<212> TYPE: DNA
<213> ORGANISM: Artificial Sequence
<220> FEATURE:
<223> OTHER INFORMATION: NC2.9 Mut 12 rev

<400> SEQUENCE: 111
gaagaacggc atcaaggtga actctgccaa tttag                    35

<210> SEQ ID NO 112
<211> LENGTH: 36
<212> TYPE: DNA
<213> ORGANISM: Artificial Sequence
<220> FEATURE:
<223> OTHER INFORMATION: NC2.9 Mut 12 rev

<400> SEQUENCE: 112
ttgatgccgt tcttctgctt gtaattagtt actagc          36

<210> SEQ ID NO 113
<211> LENGTH: 35
<212> TYPE: DNA
<213> ORGANISM: Artificial Sequence
<220> FEATURE:
<223> OTHER INFORMATION: NC2.9 Mut 13 fwd

<400> SEQUENCE: 113
gaagaacggc atcaaggtga actggtcaaa tgagc          35

<210> SEQ ID NO 114
<211> LENGTH: 34
<212> TYPE: DNA
<213> ORGANISM: Artificial Sequence
<220> FEATURE:
<223> OTHER INFORMATION: NC2.9 Mut 13 rev

<400> SEQUENCE: 114
ttgatgccgt tcttctgctt gtacagagaa tcgg          34

<210> SEQ ID NO 115
<211> LENGTH: 35
<212> TYPE: DNA
<213> ORGANISM: Artificial Sequence
<220> FEATURE:
<223> OTHER INFORMATION: NC2.9 Mut 14 fwd

<400> SEQUENCE: 115
gaagaacggc atcaaggtga actgtttgaa gtggc          35

<210> SEQ ID NO 116
<211> LENGTH: 34
<212> TYPE: DNA
<213> ORGANISM: Artificial Sequence
<220> FEATURE:
<223> OTHER INFORMATION: NC2.9 Mut 14 rev

<400> SEQUENCE: 116
ttgatgccgt tcttctgctt gtcttgacca caac          34

<210> SEQ ID NO 117
<211> LENGTH: 35
<212> TYPE: DNA
<213> ORGANISM: Artificial Sequence
<220> FEATURE:
<223> OTHER INFORMATION: NC2.9 Mut 15 fwd

<400> SEQUENCE: 117
gaagaacggc atcaaggtga actcttggtg tggac          35

<210> SEQ ID NO 118
<211> LENGTH: 36
<212> TYPE: DNA
<213> ORGANISM: Artificial Sequence
<220> FEATURE:
<223> OTHER INFORMATION: NC2.9 Mut 15 rev

<400> SEQUENCE: 118
ttgatgccgt tcttctgctt gtatagtttc atgaat          36

<210> SEQ ID NO 119

```
<211> LENGTH: 35
<212> TYPE: DNA
<213> ORGANISM: Artificial Sequence
<220> FEATURE:
<223> OTHER INFORMATION: NC2.9 Mut 16 fwd

<400> SEQUENCE: 119
gaagaacggc atcaaggtga actcattacc ccata                              35

<210> SEQ ID NO 120
<211> LENGTH: 34
<212> TYPE: DNA
<213> ORGANISM: Artificial Sequence
<220> FEATURE:
<223> OTHER INFORMATION: NC2.9 Mut 16 rev

<400> SEQUENCE: 120
ttgatgccgt tcttctgctt gtccccttgc tatg                               34

<210> SEQ ID NO 121
<211> LENGTH: 35
<212> TYPE: DNA
<213> ORGANISM: Artificial Sequence
<220> FEATURE:
<223> OTHER INFORMATION: NC2.9 Mut 17 fwd

<400> SEQUENCE: 121
gaagaacggc atcaaggtga actcacagat agcaa                              35

<210> SEQ ID NO 122
<211> LENGTH: 34
<212> TYPE: DNA
<213> ORGANISM: Artificial Sequence
<220> FEATURE:
<223> OTHER INFORMATION: NC2.9 Mut 17 rev

<400> SEQUENCE: 122
ttgatgccgt tcttctgctt gttccagagg agtc                               34

<210> SEQ ID NO 123
<211> LENGTH: 35
<212> TYPE: DNA
<213> ORGANISM: Artificial Sequence
<220> FEATURE:
<223> OTHER INFORMATION: NC2.9 Mut 18 fwd

<400> SEQUENCE: 123
gaagaacggc atcaaggtga actgctacct tcagc                              35

<210> SEQ ID NO 124
<211> LENGTH: 34
<212> TYPE: DNA
<213> ORGANISM: Artificial Sequence
<220> FEATURE:
<223> OTHER INFORMATION: NC2.9 Mut 18 rev

<400> SEQUENCE: 124
ttgatgccgt tcttctgctt gtcagcactc tcct                               34

<210> SEQ ID NO 125
<211> LENGTH: 35
<212> TYPE: DNA
<213> ORGANISM: Artificial Sequence
<220> FEATURE:
<223> OTHER INFORMATION: NC2.9 Mut 19 fwd

<400> SEQUENCE: 125
```
gaagaacggc atcaaggtga acttctgtgt cagtc        35

<210> SEQ ID NO 126
<211> LENGTH: 34
<212> TYPE: DNA
<213> ORGANISM: Artificial Sequence
<220> FEATURE:
<223> OTHER INFORMATION: NC2.9 Mut 19 rev

<400> SEQUENCE: 126
ttgatgccgt tcttctgctt gtggtggtag gctt        34

<210> SEQ ID NO 127
<211> LENGTH: 35
<212> TYPE: DNA
<213> ORGANISM: Artificial Sequence
<220> FEATURE:
<223> OTHER INFORMATION: NC2.9 Mut 20 fwd

<400> SEQUENCE: 127
gaagaacggc atcaaggtga actctgacca ggata        35

<210> SEQ ID NO 128
<211> LENGTH: 35
<212> TYPE: DNA
<213> ORGANISM: Artificial Sequence
<220> FEATURE:
<223> OTHER INFORMATION: NC2.9 Mut 20 rev

<400> SEQUENCE: 128
ttgatgccgt tcttctgctt gtgaagcttt tgatg        35

<210> SEQ ID NO 129
<211> LENGTH: 37
<212> TYPE: DNA
<213> ORGANISM: Artificial Sequence
<220> FEATURE:
<223> OTHER INFORMATION: NC2.9 Mut 21 fwd

<400> SEQUENCE: 129
gaagaacggc atcaaggtga acttaagtgt tgtattc        37

<210> SEQ ID NO 130
<211> LENGTH: 34
<212> TYPE: DNA
<213> ORGANISM: Artificial Sequence
<220> FEATURE:
<223> OTHER INFORMATION: NC2.9 Mut 21 rev

<400> SEQUENCE: 130
ttgatgccgt tcttctgctt gtaggcagcc actg        34

<210> SEQ ID NO 131
<211> LENGTH: 20
<212> TYPE: DNA
<213> ORGANISM: Artificial Sequence
<220> FEATURE:
<223> OTHER INFORMATION: SC1 fwd

<400> SEQUENCE: 131
gacaaagata accatcctcc        20

<210> SEQ ID NO 132
<211> LENGTH: 20
<212> TYPE: DNA

```
<213> ORGANISM: Artificial Sequence
<220> FEATURE:
<223> OTHER INFORMATION: SC1 rev

<400> SEQUENCE: 132
cacttcttca attgctgagg                                                     20

<210> SEQ ID NO 133
<211> LENGTH: 20
<212> TYPE: DNA
<213> ORGANISM: Artificial Sequence
<220> FEATURE:
<223> OTHER INFORMATION: SC1.1 rev

<400> SEQUENCE: 133
atagcaaaga cacattgtgc                                                     20

<210> SEQ ID NO 134
<211> LENGTH: 19
<212> TYPE: DNA
<213> ORGANISM: Artificial Sequence
<220> FEATURE:
<223> OTHER INFORMATION: SC1.1a rev

<400> SEQUENCE: 134
gtgcagaaat caacagcta                                                      19

<210> SEQ ID NO 135
<211> LENGTH: 20
<212> TYPE: DNA
<213> ORGANISM: Artificial Sequence
<220> FEATURE:
<223> OTHER INFORMATION: SC1.1b fwd

<400> SEQUENCE: 135
ggccattatg atctttaact                                                     20

<210> SEQ ID NO 136
<211> LENGTH: 24
<212> TYPE: DNA
<213> ORGANISM: Artificial Sequence
<220> FEATURE:
<223> OTHER INFORMATION: NC1.1 Ikaros mut. fwd

<400> SEQUENCE: 136
gactacaaga gccctattct ccta                                                24

<210> SEQ ID NO 137
<211> LENGTH: 25
<212> TYPE: DNA
<213> ORGANISM: Artificial Sequence
<220> FEATURE:
<223> OTHER INFORMATION: NC1.1 Ikaros mut. rev

<400> SEQUENCE: 137
agggctcttg tagtctaatg agctt                                               25

<210> SEQ ID NO 138
<211> LENGTH: 26
<212> TYPE: DNA
<213> ORGANISM: Artificial Sequence
<220> FEATURE:
<223> OTHER INFORMATION: NC1.1 Ets/Zeb mut. fwd

<400> SEQUENCE: 138
ctatttagaa cagtaattag atttta                                              26
```

<210> SEQ ID NO 139
<211> LENGTH: 23
<212> TYPE: DNA
<213> ORGANISM: Artificial Sequence
<220> FEATURE:
<223> OTHER INFORMATION: NC1.1 Ets/Zeb mut. rev

<400> SEQUENCE: 139
tactgttcta aataggccag gga                                          23

<210> SEQ ID NO 140
<211> LENGTH: 24
<212> TYPE: DNA
<213> ORGANISM: Artificial Sequence
<220> FEATURE:
<223> OTHER INFORMATION: NC1.1 HD mut. fwd

<400> SEQUENCE: 140
cctactacca ccgattttaa cagg                                         24

<210> SEQ ID NO 141
<211> LENGTH: 23
<212> TYPE: DNA
<213> ORGANISM: Artificial Sequence
<220> FEATURE:
<223> OTHER INFORMATION: NC1.1 HD mut. rev

<400> SEQUENCE: 141
atcggtggta gtaggagaat agg                                          23

<210> SEQ ID NO 142
<211> LENGTH: 24
<212> TYPE: DNA
<213> ORGANISM: Artificial Sequence
<220> FEATURE:
<223> OTHER INFORMATION: NC1.1 Ets/Gata mut. fwd

<400> SEQUENCE: 142
ttaaacaaca gctcaacaga tcag                                         24

<210> SEQ ID NO 143
<211> LENGTH: 26
<212> TYPE: DNA
<213> ORGANISM: Artificial Sequence
<220> FEATURE:
<223> OTHER INFORMATION: NC1.1 Ets/Gata mut. rev

<400> SEQUENCE: 143
tgagctgttg tttaaaatct aattac                                       26

<210> SEQ ID NO 144
<211> LENGTH: 30
<212> TYPE: DNA
<213> ORGANISM: Artificial Sequence
<220> FEATURE:
<223> OTHER INFORMATION: M2,

<400> SEQUENCE: 144
gcaatttaac ctacaactgc tgagcttgta                                   30

<210> SEQ ID NO 145
<211> LENGTH: 28
<212> TYPE: DNA
<213> ORGANISM: Artificial Sequence
<220> FEATURE:

-continued

```
<223> OTHER INFORMATION: M4,

<400> SEQUENCE: 145
ggcgactgtg cttccggctg gggcagtg                                          28

<210> SEQ ID NO 146
<211> LENGTH: 25
<212> TYPE: DNA
<213> ORGANISM: Artificial Sequence
<220> FEATURE:
<223> OTHER INFORMATION: M8,

<400> SEQUENCE: 146
ggagcaggga aacaataggt gattt                                             25

<210> SEQ ID NO 147
<211> LENGTH: 25
<212> TYPE: DNA
<213> ORGANISM: Artificial Sequence
<220> FEATURE:
<223> OTHER INFORMATION: M9

<400> SEQUENCE: 147
tggccagaga ggaaattggg ggttt                                             25

<210> SEQ ID NO 148
<211> LENGTH: 31
<212> TYPE: DNA
<213> ORGANISM: Artificial Sequence
<220> FEATURE:
<223> OTHER INFORMATION: M11/12

<400> SEQUENCE: 148
tcagggcaca aaggcccaac tgtctagggg g                                      31

<210> SEQ ID NO 149
<211> LENGTH: 25
<212> TYPE: DNA
<213> ORGANISM: Artificial Sequence
<220> FEATURE:
<223> OTHER INFORMATION: Myb Co

<400> SEQUENCE: 149
tcttcaagtc cgccatgccc gaagg                                             25

<210> SEQ ID NO 150
<211> LENGTH: 25
<212> TYPE: DNA
<213> ORGANISM: Artificial Sequence
<220> FEATURE:
<223> OTHER INFORMATION: Sox9 Co

<400> SEQUENCE: 150
tacggcaagc tgttcatctg cacca                                             25

<210> SEQ ID NO 151
<211> LENGTH: 25
<212> TYPE: DNA
<213> ORGANISM: Artificial Sequence
<220> FEATURE:
<223> OTHER INFORMATION: Ets1 Co

<400> SEQUENCE: 151
atgtctacgt cgagcgcgac ggcga                                             25
```

```
<210> SEQ ID NO 152
<211> LENGTH: 18
<212> TYPE: DNA
<213> ORGANISM: Artificial Sequence
<220> FEATURE:
<223> OTHER INFORMATION: Sox10E2_1

<400> SEQUENCE: 152
tgctcctgct gcttatca                                                 18

<210> SEQ ID NO 153
<211> LENGTH: 18
<212> TYPE: DNA
<213> ORGANISM: Artificial Sequence
<220> FEATURE:
<223> OTHER INFORMATION: Sox10E2_1 rev

<400> SEQUENCE: 153
atcagctcca ctgcacat                                                 18

<210> SEQ ID NO 154
<211> LENGTH: 18
<212> TYPE: DNA
<213> ORGANISM: Artificial Sequence
<220> FEATURE:
<223> OTHER INFORMATION: Sox10E2_2

<400> SEQUENCE: 154
tgataagcag caggagca                                                 18

<210> SEQ ID NO 155
<211> LENGTH: 20
<212> TYPE: DNA
<213> ORGANISM: Artificial Sequence
<220> FEATURE:
<223> OTHER INFORMATION: Sox10E2_2 rev

<400> SEQUENCE: 155
tgagcaggtt gctgtggaaa                                               20

<210> SEQ ID NO 156
<211> LENGTH: 20
<212> TYPE: DNA
<213> ORGANISM: Artificial Sequence
<220> FEATURE:
<223> OTHER INFORMATION: negcont_1

<400> SEQUENCE: 156
tcggatttta atgggctcag                                               20

<210> SEQ ID NO 157
<211> LENGTH: 20
<212> TYPE: DNA
<213> ORGANISM: Artificial Sequence
<220> FEATURE:
<223> OTHER INFORMATION: negcont_1 rev

<400> SEQUENCE: 157
ccgcagatag ttctgcatca                                               20

<210> SEQ ID NO 158
<211> LENGTH: 20
<212> TYPE: DNA
<213> ORGANISM: Artificial Sequence
<220> FEATURE:
<223> OTHER INFORMATION: negcont_2
```

-continued

<400> SEQUENCE: 158
ggttggattt ccagtctcca                                              20

<210> SEQ ID NO 159
<211> LENGTH: 20
<212> TYPE: DNA
<213> ORGANISM: Artificial Sequence
<220> FEATURE:
<223> OTHER INFORMATION: negcont_2 rev

<400> SEQUENCE: 159
tgttttgctg gacaatctgc                                              20

<210> SEQ ID NO 160
<211> LENGTH: 36
<212> TYPE: DNA
<213> ORGANISM: Artificial Sequence
<220> FEATURE:
<223> OTHER INFORMATION: Sox9_5'

<400> SEQUENCE: 160
aattctcgag gccacctgct caagggctac gactgg                            36

<210> SEQ ID NO 161
<211> LENGTH: 30
<212> TYPE: DNA
<213> ORGANISM: Artificial Sequence
<220> FEATURE:
<223> OTHER INFORMATION: Sox9_3'

<400> SEQUENCE: 161
attagatatc tttaaggccg ggtgagctgc                                   30

<210> SEQ ID NO 162
<211> LENGTH: 37
<212> TYPE: DNA
<213> ORGANISM: Artificial Sequence
<220> FEATURE:
<223> OTHER INFORMATION: Ets1_5'

<400> SEQUENCE: 162
aatactcgag ggcctcaacc atgaaggcgg cggtgga                           37

<210> SEQ ID NO 163
<211> LENGTH: 32
<212> TYPE: DNA
<213> ORGANISM: Artificial Sequence
<220> FEATURE:
<223> OTHER INFORMATION: Ets1_3'

<400> SEQUENCE: 163
attagatatc tcactcatca gcatctggct tg                                32

<210> SEQ ID NO 164
<211> LENGTH: 29
<212> TYPE: DNA
<213> ORGANISM: Artificial Sequence
<220> FEATURE:
<223> OTHER INFORMATION: cMyb_5'

<400> SEQUENCE: 164
attactcgag gccaccatgg cccggagac                                    29

<210> SEQ ID NO 165
<211> LENGTH: 27

```
<212> TYPE: DNA
<213> ORGANISM: Artificial Sequence
<220> FEATURE:
<223> OTHER INFORMATION: cMyb_3'

<400> SEQUENCE: 165
attaatcgat tcacatcacc agagtcc                                        27

<210> SEQ ID NO 166
<211> LENGTH: 48
<212> TYPE: DNA
<213> ORGANISM: Artificial Sequence
<220> FEATURE:
<223> OTHER INFORMATION: Sox9mut_5'

<400> SEQUENCE: 166
attactcgag gccaccatga acttgttgga tcccttcatg aaaatgac                 48

<210> SEQ ID NO 167
<211> LENGTH: 56
<212> TYPE: DNA
<213> ORGANISM: Artificial Sequence
<220> FEATURE:
<223> OTHER INFORMATION: Ets1mut_5'

<400> SEQUENCE: 167
attactcgag tcaaccatga aagctgccgt cgatttaaaa cccaccctga ccatca        56

<210> SEQ ID NO 168
<211> LENGTH: 25
<212> TYPE: DNA
<213> ORGANISM: Artificial Sequence
<220> FEATURE:
<223> OTHER INFORMATION: Ets1

<400> SEQUENCE: 168
gcttcaggtc caccgccgcc ttcat                                          25

<210> SEQ ID NO 169
<211> LENGTH: 25
<212> TYPE: DNA
<213> ORGANISM: Artificial Sequence
<220> FEATURE:
<223> OTHER INFORMATION: cMyb

<400> SEQUENCE: 169
atggccgcga gctccgcgtg cagat                                          25

<210> SEQ ID NO 170
<211> LENGTH: 25
<212> TYPE: DNA
<213> ORGANISM: Artificial Sequence
<220> FEATURE:
<223> OTHER INFORMATION: Sox9

<400> SEQUENCE: 170
gggtctagga gattcatgcg agaaa                                          25

<210> SEQ ID NO 171
<211> LENGTH: 25
<212> TYPE: DNA
<213> ORGANISM: Artificial Sequence
<220> FEATURE:
<223> OTHER INFORMATION: Control

<400> SEQUENCE: 171
```
atggcctcgg agctggagag cctca                                        25

<210> SEQ ID NO 172
<211> LENGTH: 5592
<212> TYPE: DNA
<213> ORGANISM: Artificial Sequence
<220> FEATURE:
<223> OTHER INFORMATION: shRNA vector

<400> SEQUENCE: 172

```
gtaagtaata ttaaggtacg ggaggtactt ggagcggccg caataaaata tctttatttt      60
cattacatct gtgtgttggt tttttgtgtg aatcgatagt actaacatac gctctccatc     120
aaaacaaaac gaaacaaaac aaactagcaa ataggctgt ccccagtgca agtgcaggtg      180
ccagaacatt tctctatcga taggtaccga gctcttacgc gtgctagccc gggctccaga     240
tctgcgatct aagtaagctt gctgcttcat ccccgtggcc cgttgctcgc gtttgctggc     300
ggtgtccccg aagaaatat atttgcatgt ctttagttct atgatgacac aaaccccgcc      360
cagcgtcttg tcattggcgt attcgaacac gcagatgcag tcgggcggc gcggtccgag      420
gtccacttcg catattaagg tgacgcgtgt ggcctcgaac accgagcgac cctgcagcga     480
cccgcttaac agcgtcaaca gcgtgccgca gatcccaagc ttgcggccgc ttaactgcag     540
aagttggtcg tgaggcactg ggcaggtaag tatcaaggtt acaagacagg tttaaggaga     600
ccaatagaaa ctgggcttgt cgagacagag aagactcttg cgtttctgat aggcacctat     660
tggtcttact gacatccact ttgcctttct ctccacaggt gtccactccc aggttcaatt     720
acagctctta agcggccgca agctagcttg gcattccggt actgttggta aagccaccat     780
ggtgagcaag ggcgaggagc tgttcaccgg ggtggtgccc atcctggtcg agctggacgg     840
cgacgtaaac ggccacaagt tcagcgtgtc cggcgagggc gagggcgatg ccacctacgg     900
caagctgacc ctgaagttca tctgcaccac cggcaagctg cccgtgccct ggcccaccct     960
cgtgaccacc ctgacctacg gcgtgcagtg cttcagccgc taccccgacc acatgaagca    1020
gcacgacttc ttcaagtccg ccatgcccga aggtgagtc tatgggacgc ttgatgtttt     1080
cttccccctt cttttctatg gttaagttca tgtcatagga aggggataag taacagggta    1140
cagtttagaa tgggaaacag acgaatgatt gcatcagtgt ggaagtctca ggatcgtttt    1200
agtttctttt atttgctgtt cataacaatt gttttctttt gtttaattct tgctttcttt    1260
tttttctc ttcccgcaatttt ttactattat acttaatgcc ttaacattgt gtataacaaa    1320
aggaaatatc tctgagatac attaagtaac ttaaaaaaaa actttacaca gtctgcctag    1380
tacattacta tttggaatat atgtgtgctt atttgcatat tcataatctc cctactttat    1440
tttcttttat ttttaattga tacataatca ttatacatat ttatgggtg ctcgcttcgg     1500
cagcacatat actatgtttg aatgaggctt cagtacttta cagaatcgtt gcctgcacat    1560
cttggaaaca cttgctggga ttacttcttc aggttaaccc aacagaaggc tcgagaaggt    1620
atattgctgt tgacagtgag cgaccagtct ctatgctgtc ctagtagtga agccacagat    1680
gtactaggac agcatagaga ctgggtgcct actgcctcgg aattcaaggg gctactttag    1740
gagcaattat cttgtttact aaaactgaat accttgctat ctctttgata cattttaca    1800
aagctgaatt aaaatggtat aaattaaatc acttttttca attgttaaag tgtaatgttt    1860
taatatgtgt acacatattg accaaatcag ggtaattttg catttgtaat tttaaaaaat    1920
gctttcttct tttaatatac ttttttgttt atcttatttc taatactttc cctaatctct    1980
ttcttttcagg gcaataatga tacaatgtat catgcctctt tgcaccattc taaagaataa    2040
```

```
cagtgataat ttctgggtta aggcaatagc aatatctctg catataaata tttctgcata    2100
taaattgtaa ctgatgtaag aggtttcata ttgctaatag cagctacaat ccagctacca    2160
ttctgctttt attttatggt tgggataagg ctggattatt ctgagtccaa gctaggccct    2220
tttgctaatc atgttcatac ctcttatctt cctcccacag ctacgtccag gagcgcacca    2280
tcttcttcaa ggacgacggc aactacaaga cccgcgccga ggtgaagttc gagggcgaca    2340
ccctggtgaa ccgcatcgag ctgaagggca tcgacttcaa ggaggacggc aacatcctgg    2400
ggcacaagct ggagtacaac tacaacagcc acaacgtcta tatcatggcc gacaagcaga    2460
agaacggcat caaggtgaac ttcaagatcc gccacaacat cgaggacggc agcgtgcagc    2520
tcgccgacca ctaccagcag aacacccccca tcggcgacgg ccccgtgctg ctgcccgaca    2580
accactacct gagcacccag tccgccctga gcaaagaccc caacgagaag cgcgatcaca    2640
tggtcctgct ggagttcgtg accgccgccg ggatcactct cggcatggac gagctgtaca    2700
agtaaagcgg ccgcgactct agagtcgggg cggccggccg cttcgagcag acatgataag    2760
atacattgat gagtttggac aaaccacaac tagaatgcag tgaaaaaaat gctttatttg    2820
tgaaatttgt gatgctattg ctttatttgt aaccattata agctgcaata aacaagttaa    2880
caacaacaat tgcattcatt ttatgtttca ggttcagggg gaggtgtggg aggttttttta   2940 aagcaagtaa aacctctaca aatgtggtaa aatcgataag gatccgtcga ccgatgccct    3000
tgagagcctt caacccagtc agctccttcc ggtgggcgcg gggcatgact atcgtcgccg    3060
cacttatgac tgtcttcttt atcatgcaac tcgtaggaca ggtgccggca gcgctcttcc    3120
gcttcctcgc tcactgactc gctgcgctcg tcgttcggc tgcggcgagc ggtatcagct    3180
cactcaaagg cggtaatacg gttatccaca gaatcagggg ataacgcagg aaagaacatg    3240
tgagcaaaag gccagcaaaa ggccaggaac cgtaaaaagg ccgcgttgct ggcgttttc    3300 cataggctcc gccccctga cgagcatcac aaaaatcgac gctcaagtca gaggtggcga    3360
aacccgacag gactataaag ataccaggcg tttccccctg gaagctccct cgtgcgctct    3420
cctgttccga ccctgccgct taccggatac ctgtccgcct ttctcccttc gggaagcgtg    3480
gcgctttctc aatgctcacg ctgtaggtat ctcagttcgg tgtaggtcgt tcgctccaag    3540
ctgggctgtg tgcacgaacc ccccgttcag cccgaccgct gcgccttatc cggtaactat    3600
cgtcttgagt ccaacccggt aagacacgac ttatcgccac tggcagcagc cactggtaac    3660
aggattagca gagcgaggta tgtaggcggt gctacagagt tcttgaagtg gtggcctaac    3720
tacggctaca ctagaaggac agtatttggt atctgcgctc tgctgaagcc agttaccttc    3780
ggaaaaagag ttggtagctc ttgatccggc aaacaaacca ccgctggtag cggtggtttt    3840
tttgtttgca agcagcagat tacgcgcaga aaaaaggat ctcaagaaga tcctttgatc    3900
ttttctacgg ggtctgacgc tcagtggaac gaaaactcac gttaagggat tttggtcatg    3960
agattatcaa aaaggatctt cacctagatc cttttaaatt aaaaatgaag ttttaaatca    4020
atctaaagta tatatgagta aacttggtct gacagttacc aatgcttaat cagtgaggca    4080
cctatctcag cgatctgtct atttcgttca tccatagttg cctgactccc cgtcgtgtag    4140
ataactacga tacgggaggg cttaccatct ggccccagtg ctgcaatgat accgcgagac    4200
ccacgctcac cggctccaga tttatcagca ataaaccagc cagccggaag ggccgagcgc    4260
agaagtggtc ctgcaacttt atccgcctcc atccagtcta ttaattgttg ccgggaagct    4320
agagtaagta gttcgccagt taatagtttg cgcaacgttg ttgccattgc tacaggcatc    4380
```

-continued

```
gtggtgtcac gctcgtcgtt tggtatggct tcattcagct ccggttccca acgatcaagg    4440
cgagttacat gatcccccat gttgtgcaaa aaagcggtta gctccttcgg tcctccgatc    4500
gttgtcagaa gtaagttggc cgcagtgtta tcactcatgg ttatggcagc actgcataat    4560
tctcttactg tcatgccatc cgtaagatgc ttttctgtga ctggtgagta ctcaaccaag    4620
tcattctgag aatagtgtat gcggcgaccg agttgctctt gcccggcgtc aatacgggat    4680
aataccgcgc cacatagcag aactttaaaa gtgctcatca ttggaaaacg ttcttcgggg    4740
cgaaaactct caaggatctt accgctgttg agatccagtt cgatgtaacc cactcgtgca    4800
cccaactgat cttcagcatc ttttactttc accagcgttt ctgggtgagc aaaaacagga    4860
aggcaaaatg ccgcaaaaaa gggaataagg gcgacacgga aatgttgaat actcatactc    4920
ttcctttttc aatattattg aagcatttat cagggttatt gtctcatgag cggatacata    4980
tttgaatgta tttagaaaaa taaacaaata ggggttccgc gcacatttcc ccgaaaagtg    5040
ccacctgacg cgccctgtag cggcgcatta agcgcggcgg gtgtggtggt tacgcgcagc    5100
gtgaccgcta cacttgccag cgccctagcg cccgctcctt tcgctttctt cccttccttt    5160
ctcgccacgt tcgccggctt tccccgtcaa gctctaaatc ggggggctccc tttagggttc    5220 cgatttagtg ctttacggca cctcgacccc aaaaaacttg attagggtga tggttcacgt    5280
agtgggccat cgccctgata gacggttttt cgccctttga cgttggagtc cacgttcttt    5340
aatagtggac tcttgttcca aactggaaca cactcaacc  ctatctcggt ctattctttt    5400
gatttataag ggattttgcc gatttcggcc tattggttaa aaaatgagct gatttaacaa    5460
aaatttaacg cgaattttaa caaaatatta acgtttacaa tttcccattc gccattcagg    5520
ctgcgcaact gttgggaagg gcgatcggtg cgggcctctt cgctattacg ccagcccaag    5580
ctaccatgat aa                                                        5592
```

<210> SEQ ID NO 173
<211> LENGTH: 41
<212> TYPE: DNA
<213> ORGANISM: Artificial Sequence
<220> FEATURE:
<223> OTHER INFORMATION: SH2fwd

<400> SEQUENCE: 173

```
gatggctgct cgagaaggta tattgctgtt gacagtgagc g                         41
```

<210> SEQ ID NO 174
<211> LENGTH: 28
<212> TYPE: DNA
<213> ORGANISM: Artificial Sequence
<220> FEATURE:
<223> OTHER INFORMATION: SH2reverse

<400> SEQUENCE: 174

```
gtctagagga attccgaggc agtaggca                                        28
```

<210> SEQ ID NO 175
<211> LENGTH: 18
<212> TYPE: DNA
<213> ORGANISM: Artificial Sequence
<220> FEATURE:
<223> OTHER INFORMATION: Sox10_5 5' primer

<400> SEQUENCE: 175

```
gtgtagagcc cggtggtg                                                   18
```

```
<210> SEQ ID NO 176
<211> LENGTH: 18
<212> TYPE: DNA
<213> ORGANISM: Artificial Sequence
<220> FEATURE:
<223> OTHER INFORMATION: Sox10_5 3' primer

<400> SEQUENCE: 176
aagcaactca ccgccatc                                                 18

<210> SEQ ID NO 177
<211> LENGTH: 18
<212> TYPE: DNA
<213> ORGANISM: Artificial Sequence
<220> FEATURE:
<223> OTHER INFORMATION: Sox10_6 primer

<400> SEQUENCE: 177
tgcagaaagc atggcaga                                                 18

<210> SEQ ID NO 178
<211> LENGTH: 18
<212> TYPE: DNA
<213> ORGANISM: Artificial Sequence
<220> FEATURE:
<223> OTHER INFORMATION: Sox10_6 3' primer

<400> SEQUENCE: 178
caccaggtgc caacacaa                                                 18

<210> SEQ ID NO 179
<211> LENGTH: 18
<212> TYPE: DNA
<213> ORGANISM: Artificial Sequence
<220> FEATURE:
<223> OTHER INFORMATION: Soc10_7 5' primer

<400> SEQUENCE: 179
ccagctccct cagccttt                                                 18

<210> SEQ ID NO 180
<211> LENGTH: 18
<212> TYPE: DNA
<213> ORGANISM: Artificial Sequence
<220> FEATURE:
<223> OTHER INFORMATION: Sox 10_7 3' primer

<400> SEQUENCE: 180
atgccacatc cctggaaa                                                 18

<210> SEQ ID NO 181
<211> LENGTH: 18
<212> TYPE: DNA
<213> ORGANISM: Artificial Sequence
<220> FEATURE:
<223> OTHER INFORMATION: Sox10L8 5' primer

<400> SEQUENCE: 181
gatgcctgga tggtgctc                                                 18

<210> SEQ ID NO 182
<211> LENGTH: 18
<212> TYPE: DNA
<213> ORGANISM: Artificial Sequence
<220> FEATURE:
<223> OTHER INFORMATION: Sox10L8 3' primer
```

<400> SEQUENCE: 182
ttcagtgctt tgccacca					18

<210> SEQ ID NO 183
<211> LENGTH: 18
<212> TYPE: DNA
<213> ORGANISM: Artificial Sequence
<220> FEATURE:
<223> OTHER INFORMATION: Sox10_9 5' primer

<400> SEQUENCE: 183
gtgctggtga gccgaact					18

<210> SEQ ID NO 184
<211> LENGTH: 18
<212> TYPE: DNA
<213> ORGANISM: Artificial Sequence
<220> FEATURE:
<223> OTHER INFORMATION: Sox10_9 3' primer

<400> SEQUENCE: 184
gagggcaagc acctcaga					18

<210> SEQ ID NO 185
<211> LENGTH: 18
<212> TYPE: DNA
<213> ORGANISM: Artificial Sequence
<220> FEATURE:
<223> OTHER INFORMATION: Sox10_10 5' primer

<400> SEQUENCE: 185
gccgtgtgtc ttcccatc					18

<210> SEQ ID NO 186
<211> LENGTH: 18
<212> TYPE: DNA
<213> ORGANISM: Artificial Sequence
<220> FEATURE:
<223> OTHER INFORMATION: Sox10_10 3' primer

<400> SEQUENCE: 186
atccccacca cggagtct					18

<210> SEQ ID NO 187
<211> LENGTH: 18
<212> TYPE: DNA
<213> ORGANISM: Artificial Sequence
<220> FEATURE:
<223> OTHER INFORMATION: Sox10E 5' primer

<400> SEQUENCE: 187
ggggatactg gcctgctt					18

<210> SEQ ID NO 188
<211> LENGTH: 18
<212> TYPE: DNA
<213> ORGANISM: Artificial Sequence
<220> FEATURE:
<223> OTHER INFORMATION: Sox10E 3' primer

<400> SEQUENCE: 188
aaggcccaca gcagagtg					18

```
<210> SEQ ID NO 189
<211> LENGTH: 299
<212> TYPE: DNA
<213> ORGANISM: Homo sapiens

<400> SEQUENCE: 189
gggggcaggg gtaggcaggt gctcggtcct tgctccagct gctgacttgc ccagcagggc      60
tctgcctggg gaccacgctt cctgctgggg cactgctcct gaaagggat ccgagcccac     120 gataagaggc tcgaagcagg tccttaggaa acaatgggtg gcttgatgag acctgctctg    180
tgatactcct gagaagggag aagcccctgc agccagtccc cactggaaag gaaattgggg    240
gtttccgtgg caaccagctc cctgggcaca agacttgtc tgtctgcttg gaaggcagc     299

<210> SEQ ID NO 190
<211> LENGTH: 225
<212> TYPE: DNA
<213> ORGANISM: Mus musculus

<400> SEQUENCE: 190
ccacgcttcc tgctaaagca ccgctcctga aggggatcc gagtcctcga taagagctct      60
aggcaggtcc ctaggaacaa tggctggctt gatgaaacct gctctgtgat actcctgaga    120
agggagaagc ccctgcagcc agtccccact ggaaaggaaa ttgggggttt ccgtagcaac    180
cagctccctg ggcacaaaga ctcatctgtc tgctgagaag gcagc                    225

<210> SEQ ID NO 191
<211> LENGTH: 296
<212> TYPE: DNA
<213> ORGANISM: Rattus norvegicus

<400> SEQUENCE: 191
ggcactggcc tgggacagag tggtgatagg gctgcagttg ctgccttgcc caacagggct     60
ctgcctgggg accacgcttc ctgctaaagc accgctcctg aaggggatc tgagtcctcg    120 ataagagctc aaggcaggtc cctaggaaca atggctggct tgatgaaacc tgctctgtga    180
tactcctgag aagggagaag cccctgcagc cagtccccac tggaaaggaa attgggggtt    240
tccgtggcaa ccagctccct gggcacaaag actcatctgt ctgctgagaa ggcagc       296

<210> SEQ ID NO 192
<211> LENGTH: 218
<212> TYPE: DNA
<213> ORGANISM: Didelphis marsupialis

<400> SEQUENCE: 192
ctatgcttcc tggagggact ctgctcctga aggggatcc cgatgggtga taagggcttt     60
ggggcaggtc ctcaggaaac aatgggtggt ttgatgagac ctgctctgtg atactcctga    120
gaagcccccg aagtcagtcc ccatcggagg aaattgaagg tttccatggt aaccagctcc    180
ccgggcacaa aggccggtct gtctgctggg gaggcagc                            218
```

US 8,907,073 B2

NUCLEIC ACIDS ENCODING FOXD3 PROMOTER AND METHODS TO ISOLATE FOXD3 EXPRESSING CELLS

CROSS-REFERENCE TO RELATED APPLICATION(S)

This application is a divisional of U.S. patent application Ser. No. 12/645,431, filed Dec. 22, 2009 which claims the benefit of and priority to U.S. Provisional Application Ser. No. 61/203,334, filed Dec. 22, 2008, the entire contents of all of which are incorporated herein by reference.

STATEMENT REGARDING FEDERALLY SPONSORED RESEARCH OR DEVELOPMENT

This invention was made with government support under Grant No. NS036485 awarded by the National Institutes of Health. The government has certain rights in the invention.

INCORPORATION BY REFERENCE

The material in the text file entitled "68663SEQLISTING" amended Sep. 26, 2012 and being 82,374 bytes in size, is herein incorporated by reference in its entirety.

BACKGROUND OF THE INVENTION

Because of its stem cell properties and numerous derivatives, the vertebrate neural crest (NC) represents an excellent system for examining questions of cell specification and differentiation during development. A gene regulatory network (GRN) defines the regulatory state of neural crest cells (Meulemans D & Bronner-Fraser M (2004) Dev Cell 7(3): 291-299), such that modules of transcription factors function sequentially to first specify the neural plate border and then the nascent neural crest. The intricate regulatory interactions within the NC-GRN start with a group of transcription factors comprising an evolutionarily "inflexible" neural plate border regulatory unit, whose essential upstream function is to establish identity of the progenitor territory (Nikitina N, Sauka-Spengler T, & Bronner-Fraser M (2008) Proc Natl Acad Sci USA 105(51):20083-20088). Neural crest specifiers are genes responsible for formation of the neural crest. Sox10 is one of the earliest neural crest specifying genes, driving delamination and directly regulating numerous downstream effectors and differentiation gene batteries. FoxD3 is one of the first markers of pre-migratory neural crest in many vertebrate species including mouse, chick, Xenopus and zebrafish (Hromas et al., 1999; Kos et al., 2001; Labosky and Kaestner, 1998; Lister et al., 2006; Pohl and Knochel, 2001; Sasai et al., 2001; Yamagata and Noda, 1998). Identification of region-specific regulatory elements as described herein, provides an important tool for identifying and manipulating the spatially-specified neural crest cells.

SUMMARY OF THE INVENTION

Identified and isolated DNA enhancer sequences are provided for use in constructs to identify early stage embryonic neural crest cells. The enhancer sequences can be used in parallel with short-hairpin RNA in a vector construct for endogenously regulated gene knockdowns. The disclosed enhancer sequences can be used to isolate a selected population of early stage embryonic cells.

In a first aspect of the invention, an isolated DNA sequence is provided, the sequence being selected from the group consisting of SEQ ID NOS: 1-6.

In a second aspect of the invention, an isolated DNA sequence is provided, the sequence being selected from the group consisting of SEQ ID NOS: 7-12.

In a third aspect of the invention, a method is provided for isolating a selected group of cells from a population of cells, the method comprising: transfecting the population of cells with a DNA vector construct having at least one enhancer sequence, wherein activation of the at least one enhancer sequence occurs in the selected population and actuates expression of a reporter protein; identifying the selected group of cells; and collecting the selected population of cells by isolating cells expressing the reporter protein from cells which do not express the reporter protein.

In a fourth aspect of the invention, a DNA vector is provided for down-regulating gene expression, the DNA vector comprising: a short-hairpin RNA sequence under transcriptional control of at least one enhancer sequence.

In a fifth aspect of the invention, a method is provided for down-regulating gene expression using a DNA vector comprising a short-hairpin RNA sequence under the transcriptional control of at least one enhancer sequence, the method comprising: controlling transcription of the short-hairpin RNA sequence with endogenous factors that actuate the at least one enhancer sequence.

In a sixth aspect of the invention, a method is provided for down-regulating gene expression using a DNA vector comprising a short-hairpin RNA sequence under transcriptional control of at least one enhancer sequence, the method comprising: controlling transcription of the short-hairpin RNA sequence with endogenous factors that actuate the at least one enhancer sequence.

In a seventh aspect of the invention, an isolated DNA sequence is provided, the sequence having 60%, 70%, 80%, 90% or 95% homology to a sequence selected from the group consisting of SEQ ID NOS: 1-12.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows a table of primers used to amplify the at least 70% homologous regions across the compared genomes.

FIGS. 3B-3F show EGFP reporter expression activated by SOX10E.

FIGS. 3G-3J show in situ hybridization of endogenous Sox10.

FIGS. 4A-4F show spatially distinct expression of EGFP activated by Sox10E1 and Sox10E2 in HH9, HH15 and HH18 embryos.

FIG. 7A shows putative binding sites within Sox10E2.

FIGS. 7B-7F show Sox10E2-activated EGFP expression and the effect of mutations in putative binding sites in Sox10E2.

FIGS. 8A-8E show Sox10E2-activated EGFP expression and the effect of mutations in putative binding sites.

FIGS. 9A-9I show Sox10E2-activated EGFP expression in the presence of morpholinos to Ets1 and cMyb.

FIGS. 9J-9N show in situ hybridization of cMyb, Sox9 and Ets1 in HH6, HH8, and HH10 embryos.

FIGS. 10A-10F show Sox10E2-activated EGFP expression in the presence of Sox9 morpholinos.

FIGS. 11A-11H show that Sox9, cMyb and Ets1 morpholinos decrease endogenous Sox10 expression.

FIGS. 11I-11M show rescue of the Sox9, cMyb or Ets1 knockdown of Sox10 expression with co-expression of Sox9, cMyb or Ets1 DNA.

FIGS. 12A-12B show FITC labeled Ets1, cMyb and Sox9 morpholinos.

FIGS. 12E-12F show anti-phospho histone H3 (PH3) antibody staining.

FIGS. 12G-12H show overlays of 12A-12F.

FIGS. 12I-12J show statistical calculations of stained cells.

FIGS. 13A-13J show that overexpression of Sox9, Ets1 or cMyb ectopically induces Sox10E2-activated EGFP expression.

FIG. 13K shows agarose gel from EMSA assay.

FIG. 13L shows a Western blot of a DNA pulldown assay.

FIGS. 14A-14F show ectopic Sox10E2-activated EGFP expression with mutations in binding sites in Sox10E2 and misexpression of Sox9, cMyb and Ets1.

FIGS. 15A-15D show Western blots of cross-linked endogenous Ets1, cMyb and Sox9.

FIGS. 18A-18M show in situ hybridization of FoxD3 and NC1-, NC2- and SC1-activated EGFP expression in chick embryos.

FIGS. 20A-20J show EGFP expression activated by NC1.1 and NC1.2 fragments of NC1 and Mut.7, Mut.8, and Mut.12 mutations of NC1.

FIGS. 21A-21G show EGFP expression activated by binding site mutations in NC1.

FIG. 23 shows a table of summarizing the expression of NC2 fragments.

FIG. 24A shows short-hairpin miRNA vector under the control of NC1.

FIGS. 26A-26B show Sox10 knockdown by Sox10 shmiRNA under the control of NC1 enhancer sequence.

FIG. 26C shows corresponding QPCR and FIG. 26D shows endogenous levels of Sox10 mRNA by in situ hybridication.

FIGS. 27A-27B show EGFP tracer expression from the NC1-Sox10 shmiRNA vector of FIGS. 26A-26B.

DETAILED DESCRIPTION OF THE INVENTION

Dissection of the cis-regulatory regions of the essential neural crest specifiers, Sox10 and FoxD3, has identified enhancer sequence regions with distinct regulatory activities in the chick embryo. A Sox100 enhancer region termed Sox100E (SEQ ID NO: 1) was identified and isolated. From dissection of the Sox100E region, Sox10E1 (SEQ ID NO: 2) and Sox10E2 (SEQ ID NO: 3) were identified and isolated. Three FoxD3 enhancer regions termed NC (SEQ ID NO: 4), NC2 (SEQ ID NO: 5), and SC1 (SEQ ID NO: 6) were identified and isolated.

The enhancer regions were identified using a comparative sequence analysis approach between multiple species. Sox10 and FoxD3 are genes important for formation, migration and differentiation, and are therefore, highly conserved. Therefore, in principle, non-coding cis-regulatory regions are also conserved along with the genes they control. As shown herein, the genomic sequences from chick, zebrafish, *Xenopus*, opossum, rat, mouse and human were compared. Conserved genomic regions isolated in this manner were amplified and subcloned into reporter vectors, and the expression pattern of the reporter in vivo was tested using methods of in and ex ovo electroporation in chick embryos. The embryos were then cultured and allowed to developed for 12-24 hours and subsequently examined for reporter activity.

Figure 28A:
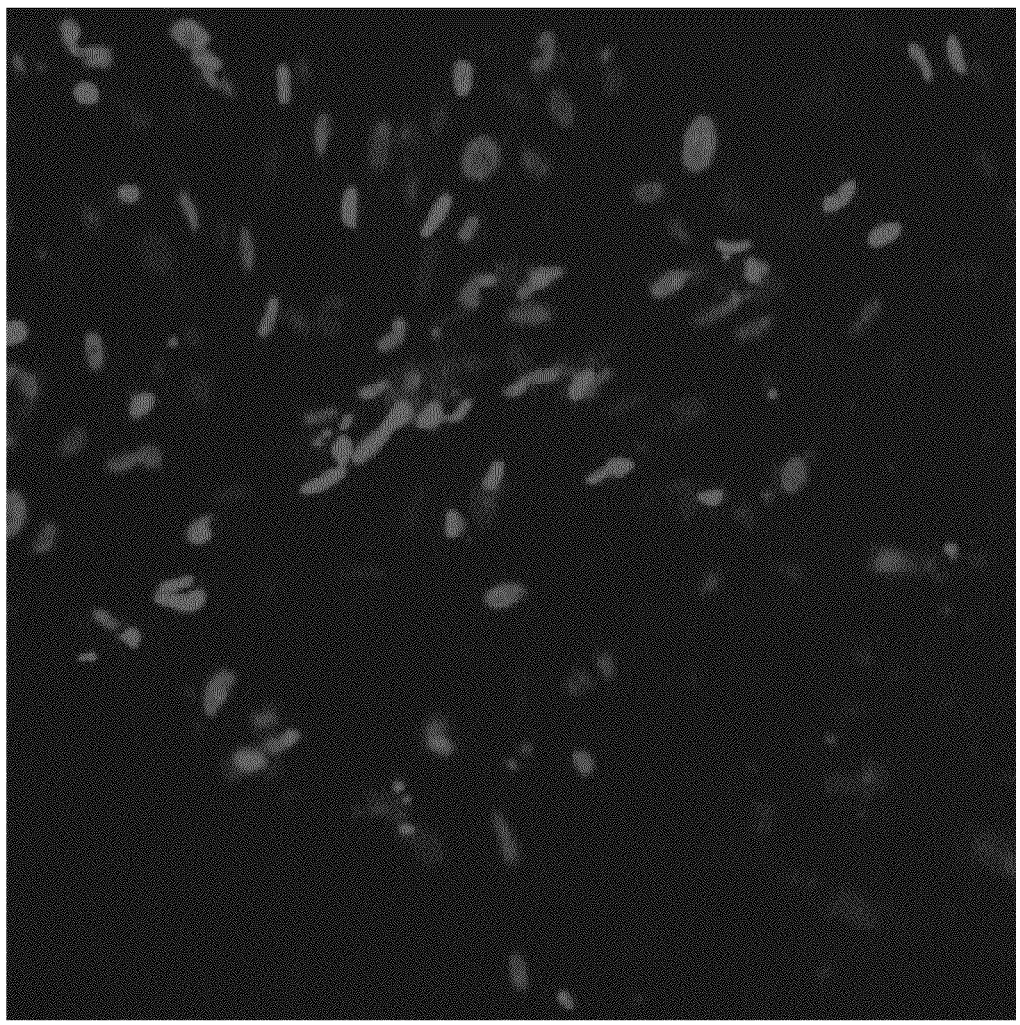
FIG. 28A shows RFP in human ES cells infected with NC1-activated RFP.
Figure 28B:
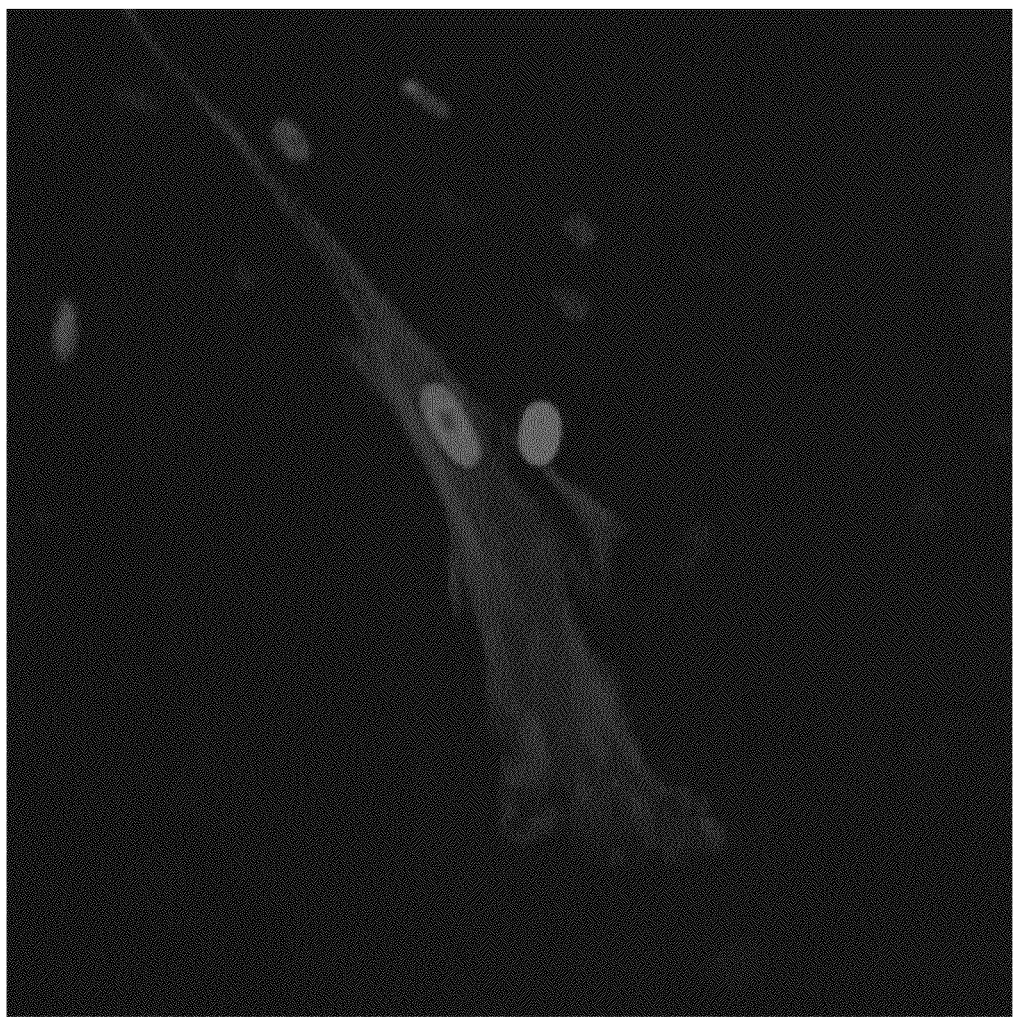
FIG. 28B shows RFP in human ES cells infected with SOX10E-activated RFP.

As further described herein, the Sox10 and FoxD3 enhancer constructs have been subcloned into a variety of expression vectors that simultaneously express fluorescent proteins. These reporter constructs can be introduced into cells either by electroporation or by viral infection using lenti virus. As shown herein, the enhancer constructs isolated from the chicken genome have been used to infect human embryonic stem (ES) cells, wherein the reporter protein was activated in cells directed to differentiate as human neural crest cells (FIGS. 28A, 28B).

Because neural crest cells represent an important stem cell population, the enhancer constructs, as described herein, are important indicators of when a cell has acquired a neural crest fate and, thus, can be utilized in regenerative medicine laboratories for replacing neural crest derivatives. In one embodiment, the enhancer regions, as described herein, are a tool for identifying and isolating neural crest cells. In another embodiment, the enhancer regions, when driving transcription of a short-hairpin RNA expression vector, control targeted gene knockdowns to endogenous levels. In another embodiment, the enhancer regions are used to infect human embryonic stem (ES) cells, thereby providing a means for directing human ES cells to differentiate.

Isolation of Sox10E. Sox10E1 and Sox10E2

Genomic sequences surrounding the Sox10 coding region from chicken, zebrafish, *Xenopus*, opossum, mouse, rat and human were compared in silico (FIG. 1), employing the ECR Browser program. Using Sox10 BAC clone, genomic fragments of approximately 3-5 kilobases (kb), containing one or more conserved regions (≥70% homology) (FIG. 2) (SEQ ID NOS: 1, 13-18), were cloned into an EGFP (enhanced green fluorescent protein) reporter vector upstream of thymidine kinase(tk) basal promoter (Uchikawa et al. (2003) *Dev Cell* 4(4):509-519) and functionally tested in vivo for its ability to recapitulate Sox10 expression during early neural crest formation. Using an ex ovo and in ovo electroporation techniques (Sauka-Spengler and Barembaum (2008) *Methods Cell Biol* 87:237-256), the entire epiblast of stage 4 (HH4) chick embryos, according to Hamburger and Hamilton (HH), or dorsal neural tube of stage HH8-12 embryos were transfected with reporter construct (green), together with a pCI-H2B-RFP (red) ubiquitous tracer to assess transfection extent and efficiency. Embryos were collected after 8-48 hours (HH8 to HH18), fixed and analyzed for EGFP expression.

The results reveal a 3.5 kb fragment, that is approximately 1 kb downstream of the Sox10 coding region, that activates EGFP reporter expression (FIGS. 3B-3F) in a manner that recapitulates endogenous Sox10 transcription (FIGS. 3G-3J), as the neural crest delaminates and migrates from the neural tube. EGFP transcripts were detected in cranial neural crest cells as early as HH8+ (FIG. 3B), in embryos with six somites, when Sox10 is first distinguishable by in situ hybridization (FIG. 3G). Both the EGFP reporter and endogenous Sox10 were maintained on actively migrating cranial neural crest (FIGS. 3D, 3F, 3I) as expression initiates progressively caudally (FIGS. 3I, 3J) (Cheng Y, et al. (2000) *Brain Res Dev Brain Res* 121(2):233-241.). However, while endogenous Sox10 is down-regulated as crest cells enter the branchial arches (FIG. 3J), expression of the EGFP reporter was maintained in branchial arches (similar to FIG. 4*b*). Both Sox10 and EGFP were also expressed in otic placode cells by stage HH10 (FIGS. 3C, 3H) and later, more caudally, in actively migrating, but not early delaminating vagal and trunk neural crest (FIGS. 3D, 3E, 3I, 3J).

Thus, this 3.5 kb Sox10 genomic fragment (denoted Sox10E) (SEQ ID NO: 1) contains regulatory modules that mediate initial Sox10 activation during early neural crest delamination at the cranial, but not more caudal levels. Of the six other fragments upstream of the coding region, five fragments lacked functional activity at the time points of interest. Another 5 kb fragment, denoted Sox10L8 (FIG. 1), exhibited weak EGFP activity in neural crest and otic cells by HH13 (6/6), but not in emigrating neural crest. (The ratio (6/6) refers to the number of times the result was observed over the number of times electroporation was performed. This ratio will be found throughout.)

Figure 5A:
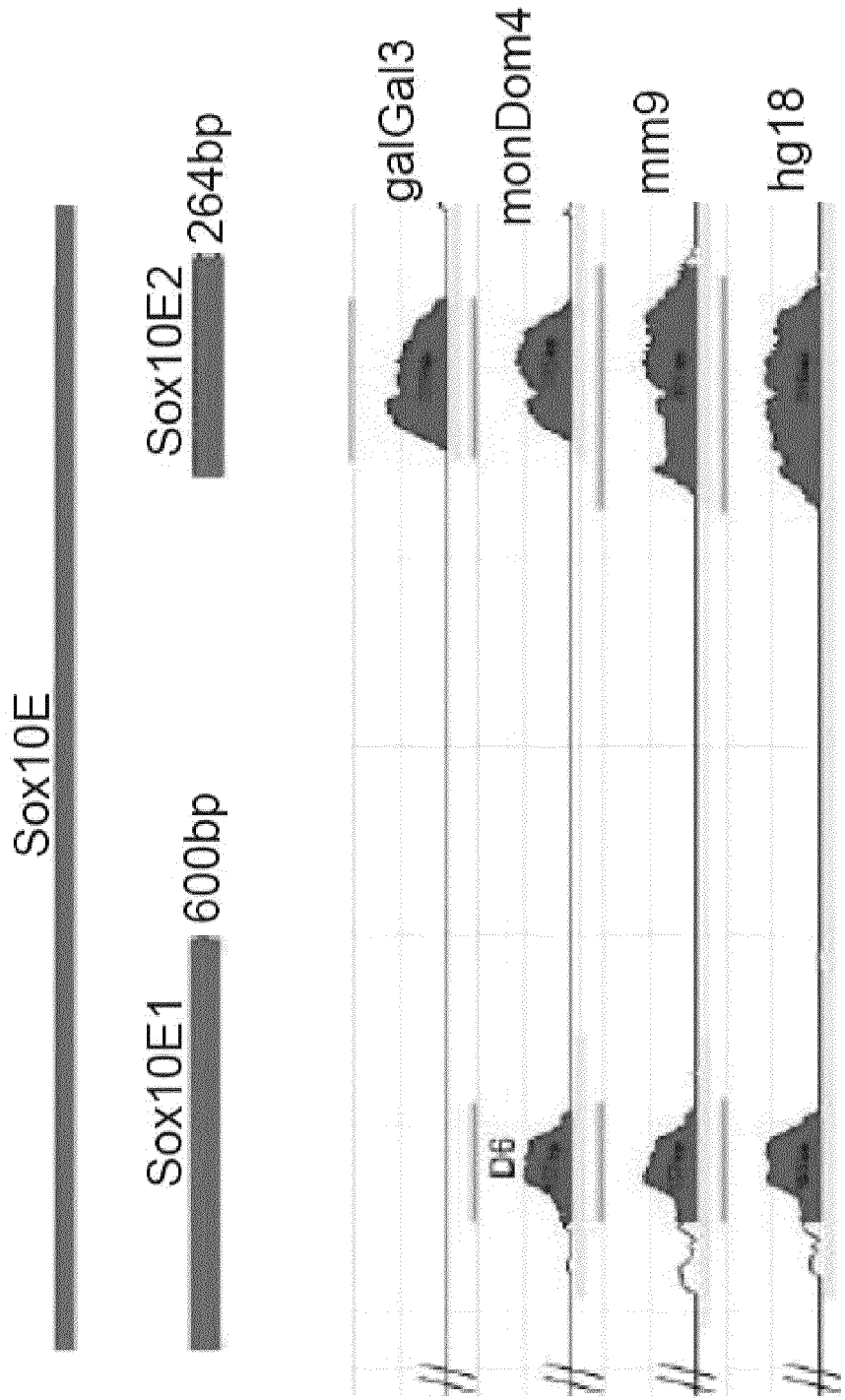
FIG. 5A shows homology of Sox10E1 and Sox10E2 across chicken, opossum, mouse, rat and human genomes.

Two highly conserved regions within Sox100E genomic fragment activate distinct spatiotemporal reporter expression. The ECR browser program was used to search for highly conserved sequences, potentially representing minimal essential core regulatory elements. By screening for 70% conservation across 100 bp windows within multiple aligned genomic regions between Sox10 and the first downstream neighboring gene, POLR2F, the program revealed two clusters of ~160 base pairs (bp) and ~267 bp within the 3.5 kb Sox10E fragment (SEQ ID NO: 1) (FIG. 5A). Assaying two smaller fragments, each containing one identified conserved region, revealed that they activated EGFP expression in spatially distinct populations and in temporally distinct manners. A 600 bp fragment termed, Sox10E 1 (SEQ ID NO: 2), lacked activity in emigrating or migrating cranial crest (FIGS. 4A-4D). It was first active in migrating vagal crest at HH15 (FIG. 5C) and in trunk crest, otic vesicle and condensed trigeminal ganglia (FIGS. 5D, 5E), but did not drive EGFP expression in delaminating vagal or trunk neural crest.

Figure 5B:
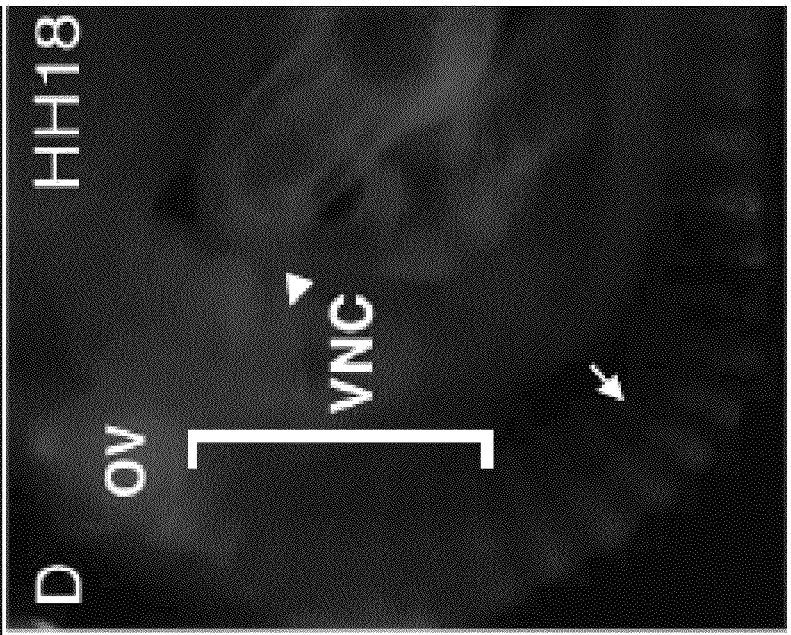
FIGS. 5B-5D show Sox10E1- and Sox10E2-activated EGFP expression in HH9, HH15 and HH18 embryos.
Figure 5C:
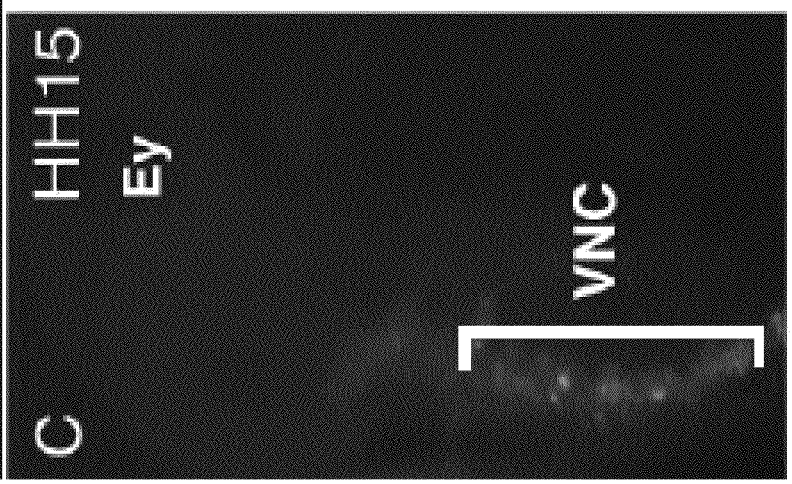
Figure 5D:
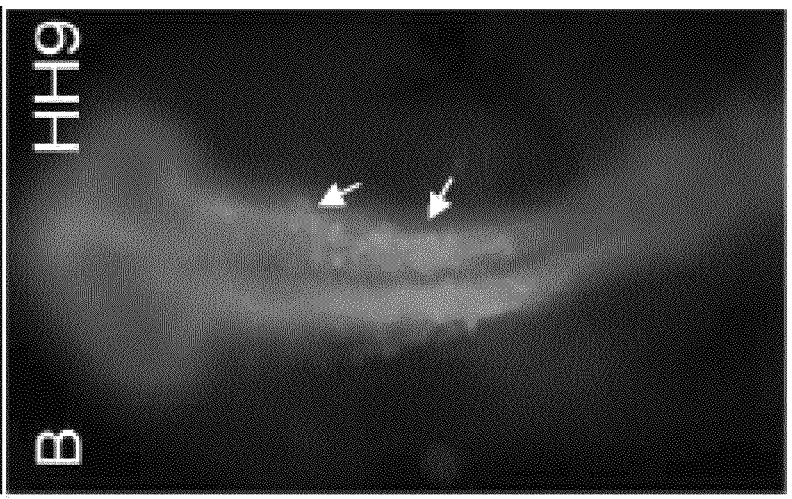
Figure 5E:
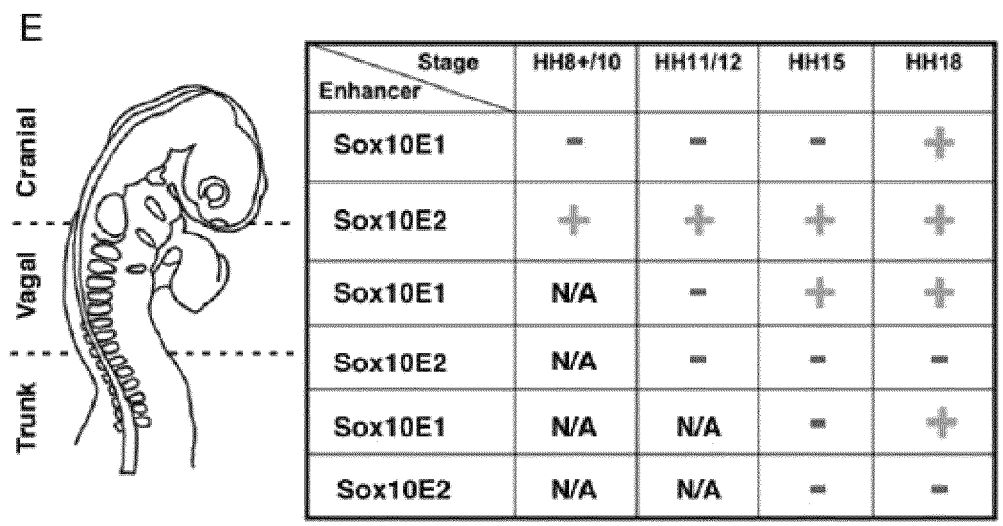
FIG. 5E shows as schematic of a chick embryo with cranial, vagal and trunk regions aligned with a table showing Sox10E1 and Sox10E2 activated EGFP expression.
Figure 6A:
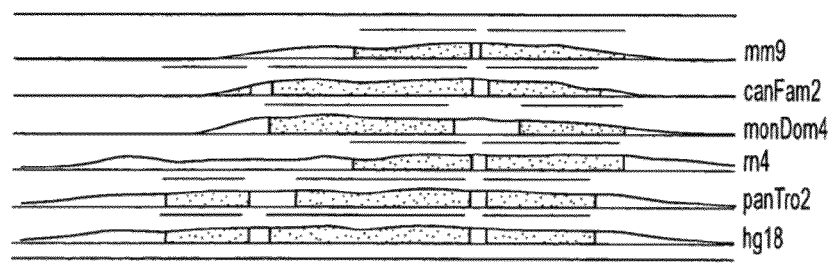
FIGS. 6A-6B show the region of Sox10E2 from the genomic comparison of FIG. 5A.
Figure 6B:
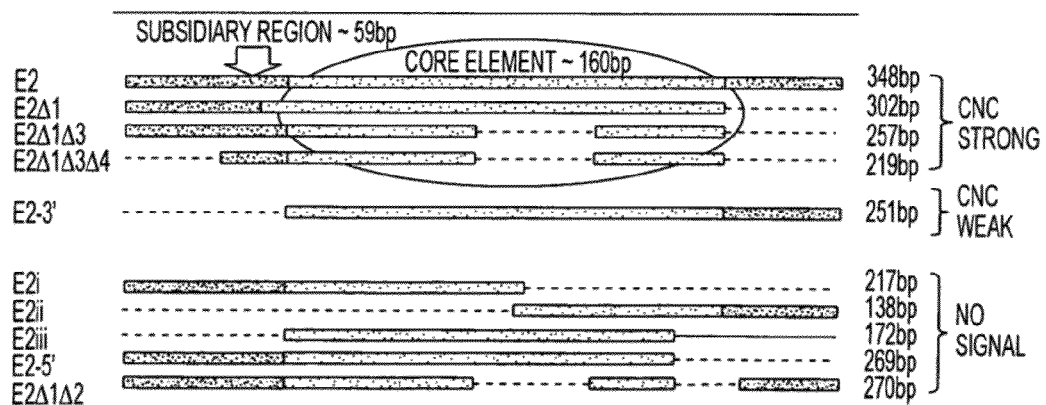

Systematic deletions within the Sox100E (SEQ ID NO: 1) region revealed a second active region—a 264 bp minimal enhancer fragment, termed Sox10E2 (SEQ ID NO: 2), comprised of an essential highly conserved 160 bp core and supporting elements within 59 bp upstream thereof (FIGS. 6A-6B). In contrast to the late activating Sox10E1, Sox10E2 displayed enhancer activity as early as HH8+ in the first cranial crest emigrating from the neural tube, mimicking Sox10E activity (FIG. 3B) that intensified through HH9 (FIG. 5B). At HH12-15, Sox10E2 reporter expression was maintained in periocular crest, rostral hindbrain streams and otic vesicle (OV) (FIGS. 4B, 4E), but absent from caudal hindbrain or trunk levels (FIGS. 4B, 4C, 4E, 4F). Just as Sox10E (SEQ ID NO: 1) displays regulatory activity within the branchial arches, Sox10E2 (SEQ ID NO: 3) drives EGFP expression in rostral hindbrain crest populating the first two arches (FIGS. 4B, 4E), and Sox10E1 (SEQ ID NO: 2) is active in vagally-derived crest (rhombomeres 6-8) (arrows, FIG. 4B) of posterior branchial arches 3-5 (arrowheads, FIG. 4D). In contrast, expression of endogenous Sox10 is down-regulated upon entering the arches (FIG. 3J). This ectopic expression is indicative of a loss of a repressor element from the Sox10E fragments. The results show that both cis-regulatory fragments Sox10E1 (SEQ ID NO: 2) and Sox10E2 (SEQ ID NO: 3) can regulate Sox10 expression in neural crest and otic regions, but in spatially and temporally distinct patterns. Each Sox10E1 (SEQ ID NO: 2) and Sox10E2 (SEQ ID NO: 3) regulates a portion of endogenous Sox10 expression, which initiates in a rostrocaudal temporal sequence (FIG. 5E).

Binding motifs for SoxE, Ets and Myb are necessary for Sox10E2 regulatory activity. To identify putative transcription factor binding sites within the 264 bp Sox10E2 regulatory fragment, the corresponding sequences from human, mouse, rat, opossum and *Xenopus* genomic regions were aligned to chicken and screened for conserved motifs. Concomitantly, sequences were analyzed for known transcription factor consensus sites using Transfac 7.0, rVista and Jaspar programs. This revealed three highly conserved binding motifs (100% homology across amniotes), two for the SoxE family of proteins (Sox8, Sox9, Sox10) and one for Ets factors. Conservation of other putative binding motifs ranged from 50-80% (FIG. 7A). Computationally identified binding motifs within Sox10E2 were tested for function via mutation/deletion analyses. Mutated versions of Sox10E2-EGFP constructs were generated for individual putative binding motifs, electroporated into chicken embryos, and analyzed after 10-12 hours (HH10-12).

Mutation of a putative Ets binding motif, within the enhancer core (M9; FIG. 7A), completely abolished Sox10E2 expression (FIG. 7C; 8/8). Similarly, reporter activity in cranial neural crest (FIG. 7B) was eliminated upon mutation of either SoxE binding site within the essential core region (M8, M11; FIG. 7A), indicating both were required for its activity (FIG. 8*b;* 13/13). Interestingly, there are two putative binding motifs for Myb factors in Sox10E2, one within the core and the other in the upstream adjacent supporting region (M2, M12; FIG. 7A), each contributing to regulatory activity. When both were replaced with random sequences, this double mutation completely abolished reporter expression (FIG. 8C; 7/7). Individual mutation of other computationally identified motifs only reduced enhancer activity. For example, perturbations of SoxD (M13; 10/10), Elk/Ets(M4; 7/7) and single Myb (M2,M12; 6/6) sites diminished EGFP signal intensity (FIGS. 7A,7D; FIG. 8D) suggesting they enhance regulatory function. In contrast, several mutations had no effect; e.g. simultaneous mutation of four putative Pax binding sites (M1, M3,M5,M7; FIGS. 7A,7E; 7/7), deletion of 45 bp within the core region (FIG. 7A, faded portion; 11/11), or mutation of either of two NFκB binding site (M6,M10; FIG. 8; 6/6). Taken together, these results show that SoxE, Ets and Myb binding motifs are each necessary for Sox10E2 regulatory function. In addition to neural crest expression, these mutations also affected expression of the Sox10E2 reporter in the otic placode.

We tested whether SoxE, Ets and Myb binding sites, within the 264 bp Sox10E2 fragment (SEQ ID NO: 3), are essential for regulatory activity of a larger construct from the Sox10 locus. To this end, we mutated these same sites (M2,M8,M9, M11,M12; FIG. 7A) within a much larger genomic fragment (~3.5 kb) to test whether other genomic regions surrounding these enhancers could compensate for the loss of activity. Whereas the full length, non-mutated construct gave robust GFP staining that recapitulated endogenous Sox10 expression, reporter activity in delaminating neural crest was completely eliminated in the same construct bearing mutations in SoxE, Ets and Myb binding sites within Sox10E2 (FIG. 7F; 6/6). As expected, later reporter expression was observed in migrating vagal and trunk neural crest since the mutated version still contained an intact Sox10E1 enhancer. These results strongly suggest that 264 bp Sox10E2 fragment (SEQ ID NO: 3) represents an essential regulatory module, and that binding sites for SoxE, Ets and Myb proteins are absolutely required for early Sox10 expression within the context of the Sox10 locus.

Figure 9I:
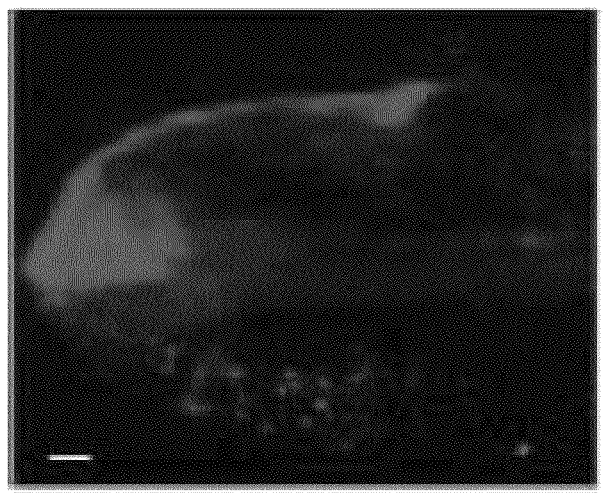
Figure 9H:
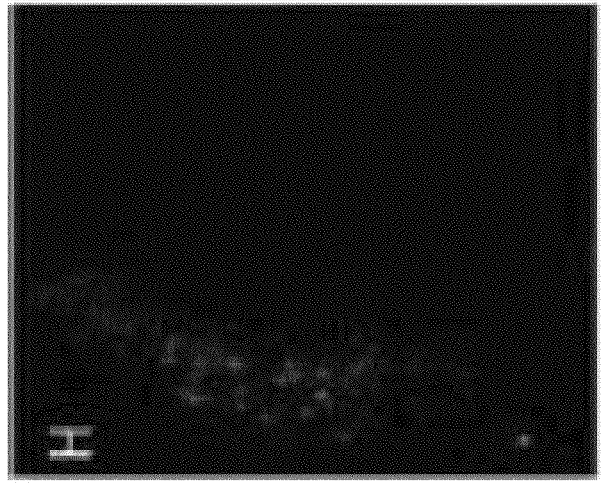
Figure 9G:
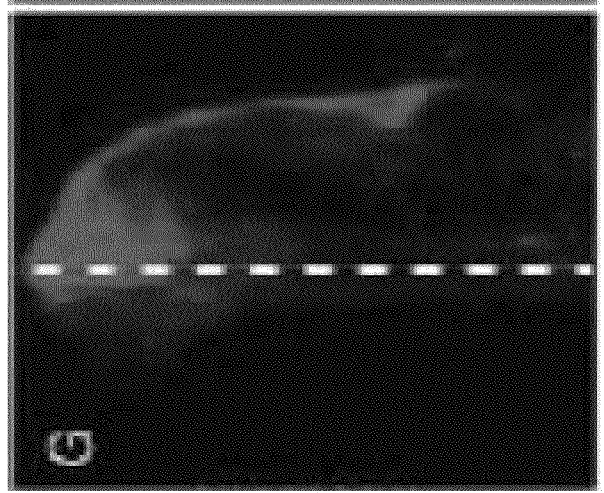

Knockdown of Ets1, cMyb or Sox9 diminishes Sox10E2 regulatory activity. To test if Ets1, cMyb and Sox9 transcription factors are required for exogenous Sox10E2 regulatory activity in delaminating neural crest, we co-electroporated either Ets1, cMyb, or Sox9 morpholino with the Sox10E2 reporter construct. The right side of each embryo received morpholino plus Sox10E2 reporter, whereas the left side received reporter plasmid alone. When the reporter construct was co-electroporated with control morpholino, reporter signal on the right side was unaffected and comparable to the contralateral side (FIGS. 9A-9C; 10/10). Conversely, in the presence of cMyb (FIGS. 9D-9F; 11/15), Ets1(FIGS. 9G-9I; 13/15), or Sox9 morpholino (FIG. 10; 15/15) expression was greatly decreased or abolished. These results show that Ets1, cMyb and Sox9, are independently required for the normal Sox10E2 regulatory activity, therefore making them good candidate factors responsible for the initial regulation of Sox10 through the identified Ets, Myb and SoxE functional binding motifs within Sox10E2.

Knockdown of Ets1, cMyb or Sox9 diminishes endogenous Sox10 expression. Although cMyb transcripts have been detected in early embryogenesis (Karafiat V, et al. (2005) *Cell Mol Life Sci* 62(21):2516-2525), their distribution was unknown and has not been described within the context of the neural crest gene regulatory network. Our results, using in situ hybridization, show that cMyb is expressed at stage HH6 in the neural plate border (FIG. 9J), and that transcripts accumulate in the neural folds by HH8, with strongest expression at the dorsal margins containing neural crest precursors (FIGS. 9K, 9K'). At HH10, transcripts are seen in neural crest cells delaminating and emigrating from the cranial neural tube (FIGS. 9L, 9L'). Thus, cMyb, like Sox9 (FIG. 9M) and Ets1 (FIG. 9N), is expressed in presumptive cranial neural crest prior to Sox10. The presence of cMyb at the neural plate border and premigratory neural crest illuminates a new role, at the onset of Sox10 expression, in neural crest cell specification. Its initial expression coincides with that of early neural crest specifiers such as AP-2, c-Myc or Snail2. Furthermore, overexpression of cMyb up-regulates Msx1 and Snail2, and thus, participates in BMP4 input into the epithelial-mesenchymal transition of trunk neural crest (Karafiat V, et al. (2005) *Cell Mol Life Sci* 62(21):2516-2525).

Figures 12C, 12D:
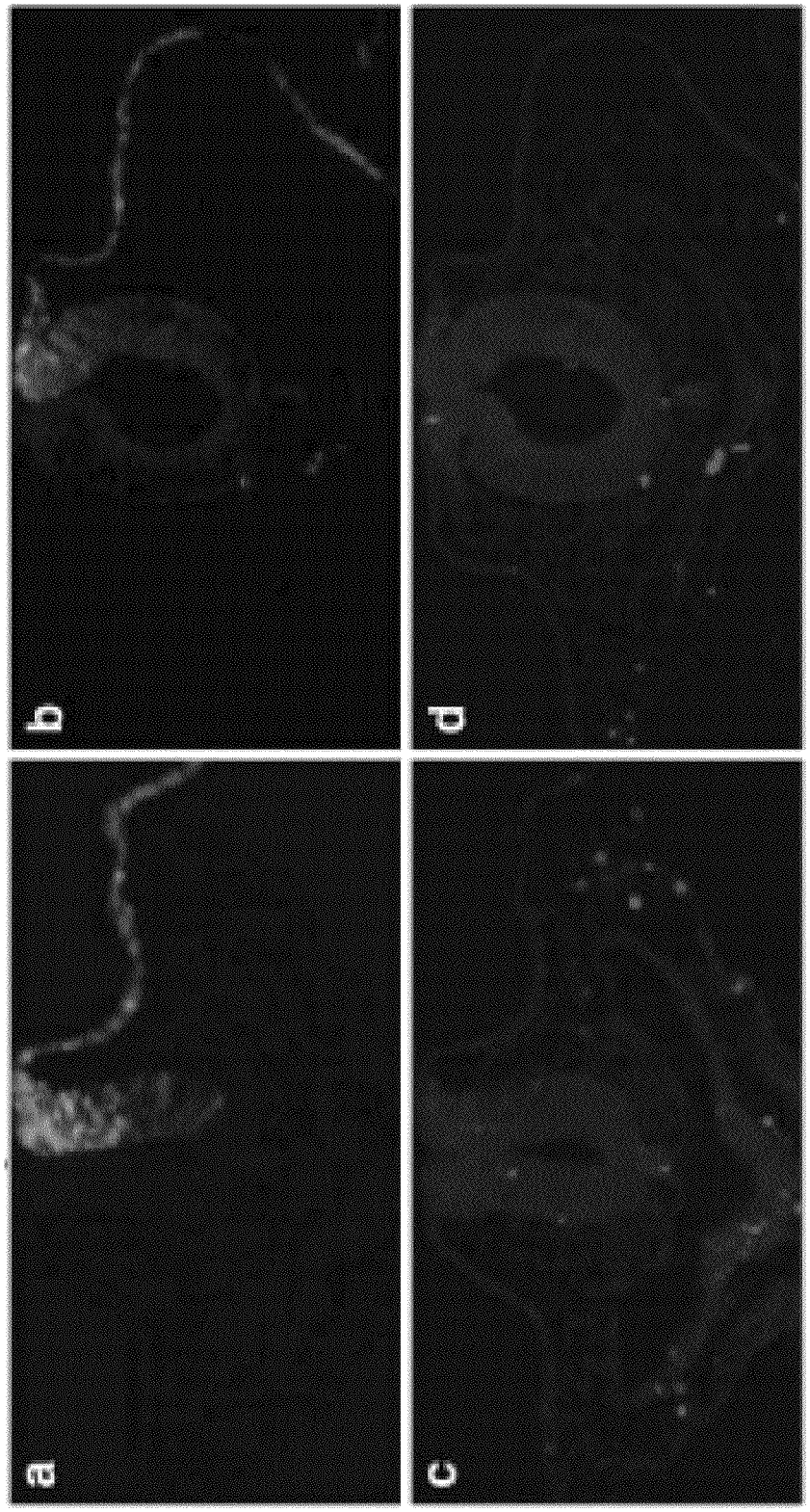
FIGS. 12C-12D show TUNEL staining.

In order to confirm that endogenous Ets1, Sox9 or cMyb proteins are required as upstream regulators of Sox10 in delaminating crest in vivo, the effects of cMyb, Ets1 or Sox9 morpholinos on endogenous Sox10 expression at HH8+-9 was examined The results reveal a dose-dependent effect on Sox10 expression on the electroporated versus contralateral side. A mild diminution was observed when individual morpholinos were electroporated at 1 mM (Sox9 3/3; cMyb 9/10; Ets1 7/10), but a marked decrease at 3 mM (Sox9 n=5, cMyb and Ets1 n=6, p<0.02; FIGS. 1A-11C, 11E-11G). The effect of cMyb knockdown was less strong than either Ets1 or Sox9 inactivation (phenotypes ranging from 50-75% loss in Sox10 transcript). In contrast, electroporation of a control morpholino had no effect (FIGS. 11L, 11M; 10/10) and co-electroporation of morpholinos with the corresponding mRNAs mutated within the morpholino target region successfully rescued the loss-of-function phenotype (Sox9, n=6, p<0.03; cMyb n=5, p≤0.04: Ets1, n=5, p<0.03: FIGS. 11I-11K). No statistically significant differences were noted in phosphohistone H3 or TUNEL staining between electroporated and control sides of embryos receiving either individual or all three morpholinos (~3 mM). Thus, changes in cell proliferation or cell death cannot account for loss of Sox10 transcript (FIGS. 12A-12J). The cumulative results indicate that Sox9, cMyb and Ets1 are each required for expression of endogenous Sox10. Importantly, the combined electroporation of all three morpholinos virtually eliminated transcript expression on the electroporated side (n=6, p≤0.01; FIGS. 12D, 12H). As shown herein, Sox9, cMyb and Ets1 together are necessary for initial activation of Sox10.

Sox9, Ets1 and cMyb ectopically activate and are required for Sox10E2 reporter expression. All three SoxE genes, Sox8, Sox9 and Sox10 are expressed by neural crest progenitors (Haldin C E & Labonne C (2009) *Int J Biochem Cell Biol.*) Because these genes can act redundantly (Finzsch et al. (2008) *Development* 135(4):637-646; Stolt et al. (2004) *Development* 131(10):2349-2358; Taylor and Labonne (2005) *Dev Cell* 9(5):593-603), theoretically any could activate the Sox10E2 reporter construct within the endogenous context. In all vertebrates examined, however, Sox9 expression precedes Sox10 (Antonellis A, et al. (2006) Hum Mol Genet. 15(2):259-271; Dutton J R, et al. (2008) BMC Dev Biol 8:105; Werner et al. (2007) *Nucleic Acids Res* 35(19): 6526-6538; Hong and Saint-Jeannet, (2005) *Semin Cell Dev Biol* 16(6):694-703.) e.g. chick Sox9 is expressed in dorsal neural folds as early as HH8, before either Sox10 or Sox8 (Cheung and Briscoe (2003) *Development* 130(23):5681-5693.). This narrow (4-6 hr) time delay and the Sox9 morpholino knock down results indicate that Sox9 directly regulates Sox10 onset and that this SoxE protein is responsible for initiating Sox10 expression. To test if Sox9 can regulate the identified Sox10E2 regulatory element, Sox9 protein was ectopically expressed using ubiquitous H2B-RFP expression vector. Whereas no ectopic reporter expression was seen when Sox10E2 reporter was co-electroporated with control plasmid (FIGS. 13A, 13F; 9/9), co-electroporation with Sox9 plasmid caused ectopic reporter activity in extra-embryonic region (FIGS. 13B,13G; 6/6). Similar results were obtained when cMyb was ectopically expressed (FIGS. 13D, 13I; 3/3). Because Sox9 is expressed only transiently in migrating neural crest cells, it is likely that Sox10 and/or Sox8 later act to maintain Sox10 expression.

Co-electroporation of Ets1 plasmid with Sox10E2 reporter resulted in ectopic reporter activation not only in extra-embryonic regions, but also in the trunk neural tube, which normally does not express Ets1 (Tahtakran and Selleck (2003) *Gene Expr Patterns* 3(4):455-458) (arrowheads; FIGS. 13C,13H; 12/12). In the embryo, Ets1 plays a role in cranial neural crest delamination and appears to mitigate the requirement for S phase synchronization to promote crest emigration in a cluster-like fashion. Moreover, ectopic expression of Ets1 in the trunk results in excess, cluster-like emigration of Sox10-expressing cells (Theveneau et al. (2007) *PLoS ONE* 2(11): e1142). Since expression of both Ets1 and the Sox10E2-driven reporter is cranial-specific, Sox10E2 acts like a switch distinguishing head and trunk crest populations. Since Sox9 and cMyb, but not Ets1, are normally expressed in the trunk neural tube (Tahtakran and Selleck, (2003) *Gene Expr Patterns* 3(4):455-458; Karafiat V. et al. (2005) *Cell Mol Life Sci* 62(21):2516-2525), Cheung and Briscoe, (2003) *Development* 130(23):5681-5693), ectopic Ets1 in this location likely cooperates with these other factors to induce reporter expression. To support this, combined overexpression of Sox9, Ets1 and cMyb has a broader effect and induces strong ectopic Sox10E2 expression not only extra-embryonically, but also along the neural tube, and in the ectoderm (FIGS. 14A,14D; 5/5).

Sox9, Ets1 or cMyb are each sufficient to trigger ectopic Sox10E2 enhancer activity. However, mutation of individual binding motifs or knock down of individual factors in the endogenous context shows that all three factors are necessary for normal Sox10E2 regulatory activity. Ectopic reporter activity driven by overexpression of individual transcription factors occurs mainly in the extra-embryonic region. This result indicates that these naïve, early stage cells already contain regulatory factors characteristic of multipotent tissue and are, thus, competent to switch on a neural crest-like transcriptional program in response to the proper single inputs.

To test if regulatory activity is mediated via the corresponding binding motifs of Sox9, Ets1 and Myb within Sox10E2 enhancer, we assayed their ability to ectopically activate mutated reporter constructs. Either Sox9-H2B RFP (6/6) or cEts1-H2B RFP (6/6) were co-electroporated with Sox10E2 construct with corresponding binding motif mutations. In all cases, electroporated embryos lacked ectopic reporter expression (FIGS. 13E, 13J). However, ectopic reporter expression was also affected when overexpressing either Ets1, cMyb or Sox9 with other Sox10E2 versions, containing mutations within non-cognate biding sites. For example, when Sox9 and cMyb were overexpressed and combined with a Sox10E2 reporter carrying a mutation within the Ets motif (M9), ectopic reporter expression in the extra-embryonic region was not observed (FIGS. 14B, 14E; 6/6). If Sox9 and Ets1 were over-expressed together with a Sox10E2 carrying a single mutated Myb site (M12), ectopic reporter expression was weak (FIGS. 14C. 14F; 3/3). This shows that for the Sox10E2 enhancer to have ectopic regulatory activity all binding sites need to be functional and indicates a cluster-like conformation of the motifs and synergistic action of the corresponding upstream regulators.

Sox9, Ets1 and cMyb directly bind to the Sox10E2 element. To determine if Sox9, Ets1 and cMyb can bind directly to the corresponding motifs within the Sox10E2 element, EMSA assays were performed using biotinylated double stranded oligonucleotides containing the corresponding Sox10E2 sub-fragments (underlined, FIG. 7A). A clear electrophoretic shift was observed in samples incubated with nuclear extracts from chicken embryonic fibroblasts overexpressing Sox9, Ets1 or cMyb, but not from the cells transfected with control plasmid (white arrowheads; FIG. 13K). This binding was out-competed by adding 200-fold excess of the corresponding non-labeled (cold) fragment to the binding reaction, showing specificity. The identity of the transcription factors directly binding to Sox10E2 subfragments was confirmed using a streptavidin-biotin DNA pulldown approach followed by Western blot with specific antibodies. Using biotinylated target and scrambled control fragments as bait, it was shown that specific subfragments pull down corresponding binding proteins (Sox9, Ets1 and cMyb) from the embryonic nuclear extracts. Conversely non-coated streptavidin-conjugated magnetic beads or beads coated with scrambled control fragments display no specific protein binding (FIG. 13L).

Figure 13M:
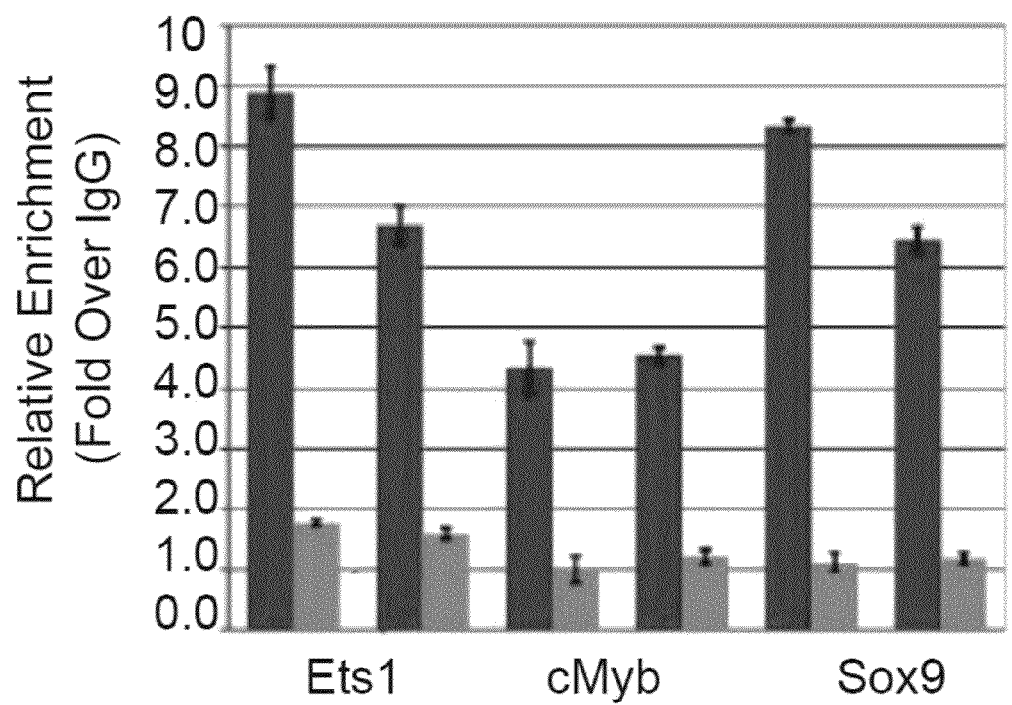
FIG. 13M shows results of in vivo qChIP assay.

Direct binding of these transcription factors to the Sox10E2 enhancer was determined in vivo using quantitative ChIP(qChIP). Crosslinked chromatin isolated from cranial regions of HH8-12 somite embryos was immunoprecipitated using Sox9, Ets1 and cMyb antibodies and ChIP-enriched DNA was used in site-specific QPCR, with primers designed to amplify fragments within the Sox10E2 region. The results show significant (4-8×) enrichment over non-specific antibody indicating that Sox10 locus and, in particular, Sox10E2 regulatory element, was occupied by endogenous Sox9, Ets1 and cMyb proteins in cranial region of HH8-HH10 chicken embryos (FIG. 13M).

As shown in FIGS. 3B-16d, Sox10E1 and Sox10E2 regulate different stages of Sox10 expression. In one embodiment, Sox10E1 (SEQ ID NO: 2) is used as a vector expression "driver" to identify cells or manipulate in vivo expression (targeted gene knockdown using miRNA, morpholino, etc) at stage HH15. In another embodiment, Sox10E2 (SEQ ID NO: 3) is used as an vector expression "driver" to identify cells or manipulate in vivo expression (at stages HH8-HH15. Cells or in vivo expression can be identified or monitored using a number of methods known in the art—e.g. the "driven" or activated expression can be of any protein that can be monitored. As shown herein, the EGFP and RFP proteins are expressed and the fluorescence is imaged. The enhancer sequences can "drive" the expression of any protein that can be monitored via fluorescence alone if the expressed protein is a fluorescent protein, specific antibody to the protein, or an antibody to a tag fused with the protein. Fluorescent expression allows for the utilization of flow cytometry to specifically isolate and sort those cells which are able to activate the particular enhancer region, from those which cannot.

Expression Patterns of FoxD3 Enhancers: NC1, NC2 and SC1

Figure 17:
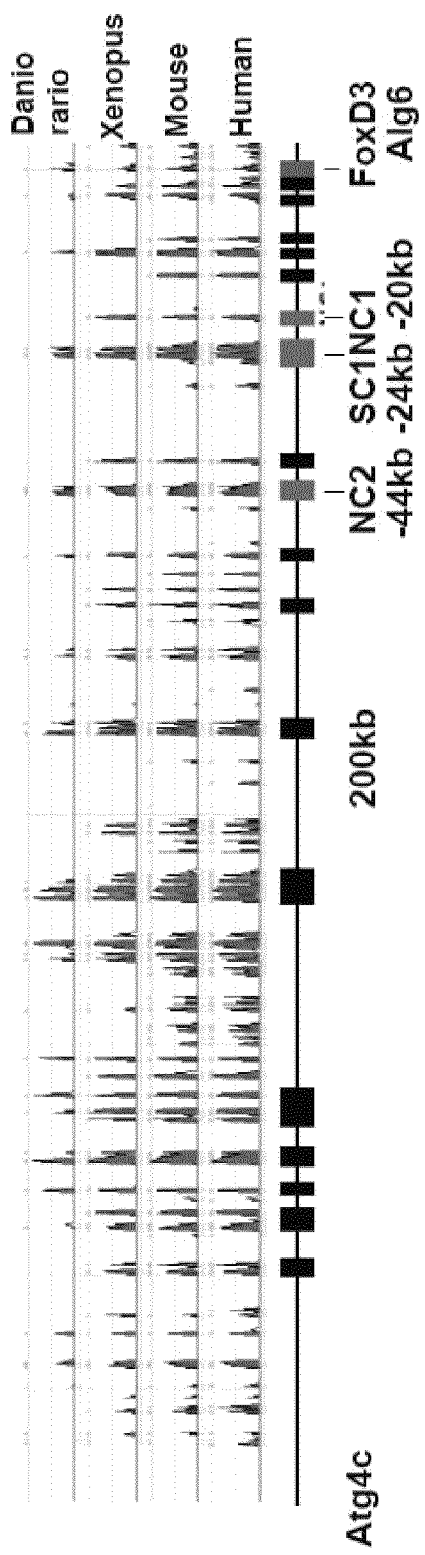
FIG. 17 shows a schematic diagram of comparative genomic analysis surrounding the FoxD3 gene in chicken, zebrafish, *Xenopus*, mouse, and human genomes.

The genomic region of FoxD3 was examined for conservation across chick, mouse, human and also opossum, *Xenopus* and zebrafish. The region spanned 160 kb between the genes immediately up and downstream of FoxD3, Atg4C and Alg6 (FIG. 17). Conserved regions varying in size from 1 kb to 4 kb were tested for enhancer activity between stages 8 and 14. Three enhancers. NC1, NC2 and SC1, (SEQ ID NOS: 4-6) were found to drive specific expression. All three enhancers are upstream of the FoxD3 gene. NC1 (SEQ ID NO: 4) is located 20 kb upstream; NC2 (SEQ ID NO: 5) is located 44 kb upstream and SC1 (SEQ ID NO: 6) is located 24 kb upstream.

In situ hybridization of FoxD3 at stage 8 is shown in FIG. 18A. NC1-directed (SEQ ID NO: 4) expression of EGFP in the premigratory cranial neural crest beginning at stage 8 is shown in FIG. 18B. In situ hybridization of FoxD3 in stage 11 embyros as shown in FIG. 18C. NC1-directed expression in stage 11 embryos continued during neural crest migration (FIG. 18D, 18G) and lasted until approximately stage 14, at which stage only very weak EGFP expression could be detected. Only the neural crest from the midbrain to rhombomere (R) 2 showed expression from NC1 (FIG. 18D). Expression of NC-1-EGFP was not seen caudal to R3.

In contrast to NC-1, the enhancer NC2 (SEQ ID NO: 5) directed strong expression of EGFP in the premigratory and migratory neural crest in R6 and caudal to R6 (FIG. 18E). The expression pattern of EGFP in the vagal and trunk neural crest matched the mRNA expression of FoxD3, and both extend to the premigratory crest at the level of the 4th most caudal somite. Expression of NC-2-activated EGFP in R4 crest was weaker, in contrast to the early expression in the vagal and trunk neural crest (FIG. 18E). There was also weak expression of EGFP in the migrating cranial neural crest (FIG. 18H), which was not detected prior to stage 9+. The first expression of EGFP driven by NC2 was observed in the vagal and trunk levels of stage 9 embryos in pre-migratory neural crest. Additionally, very weak EGFP expression was also observed in the developing optic retina from stage 11 and a very small number of cells displayed very weak expression in the otic vesicle at stage 12.

To examine the temporal regulation of the NC2 enhancer (SEQ ID NO: 5), stage 8 to 14 embryos were electroporated using in ovo electroporation, and the embryos were fixed after 24-48 h. FoxD3 is expressed in most pre-migratory and migratory vagal and trunk neural crest, but is not expressed by pre-migratory and migratory melanoblasts, which undergo emigration approximately 24 h after the emigration of ganglionic neural crest. NC2-activated EGFP expression was observed in melanoblasts prior to and during migration (FIG. 18L), in addition to expression in the dorsal root ganglia. To confirm that this expression was due to activity of the enhancer and not stability of EGFP, in situ hybridization for EGFP was performed and mRNA for EGFP was detected in melanoblasts and dorsal root ganglia. Expression of NC-2-activated EGFP was also observed in neural crest cells migrating along the enteric nervous system.

The third FoxD3 enhancer, SC1 (SEQ ID NO: 6), directed expression of EGFP in a subset of cells in the vagal and trunk neural tube from R5 caudally beginning at stage 8+. These SC-1-activated EGFP-positive cells were seen in the dorsal neural tube in the location of pre-migratory neural crest, and also in at mid levels of the neural tube (FIG. 18F, 18J). Some SC-1-activated EGFP-positive cells were seen emigrating from the neural tube, however expression was not seen in the dorsal root ganglia. FIG. 18M shows a cross-section of E4 embryo with EGFP driven by SC1 enhancer. Electroporation at stage 12 and fixation after 24 and 48 h revealed no expression with SC1-activated EGFP in the dorsal root ganglia or other neural crest derivatives, but SC-1-activated EGFP was seen in a population of interneurons in the neural tube at E4, which corresponds to a region of FoxD3 expression (FIG. 18M).

Dissection of NC1

Figure 19:
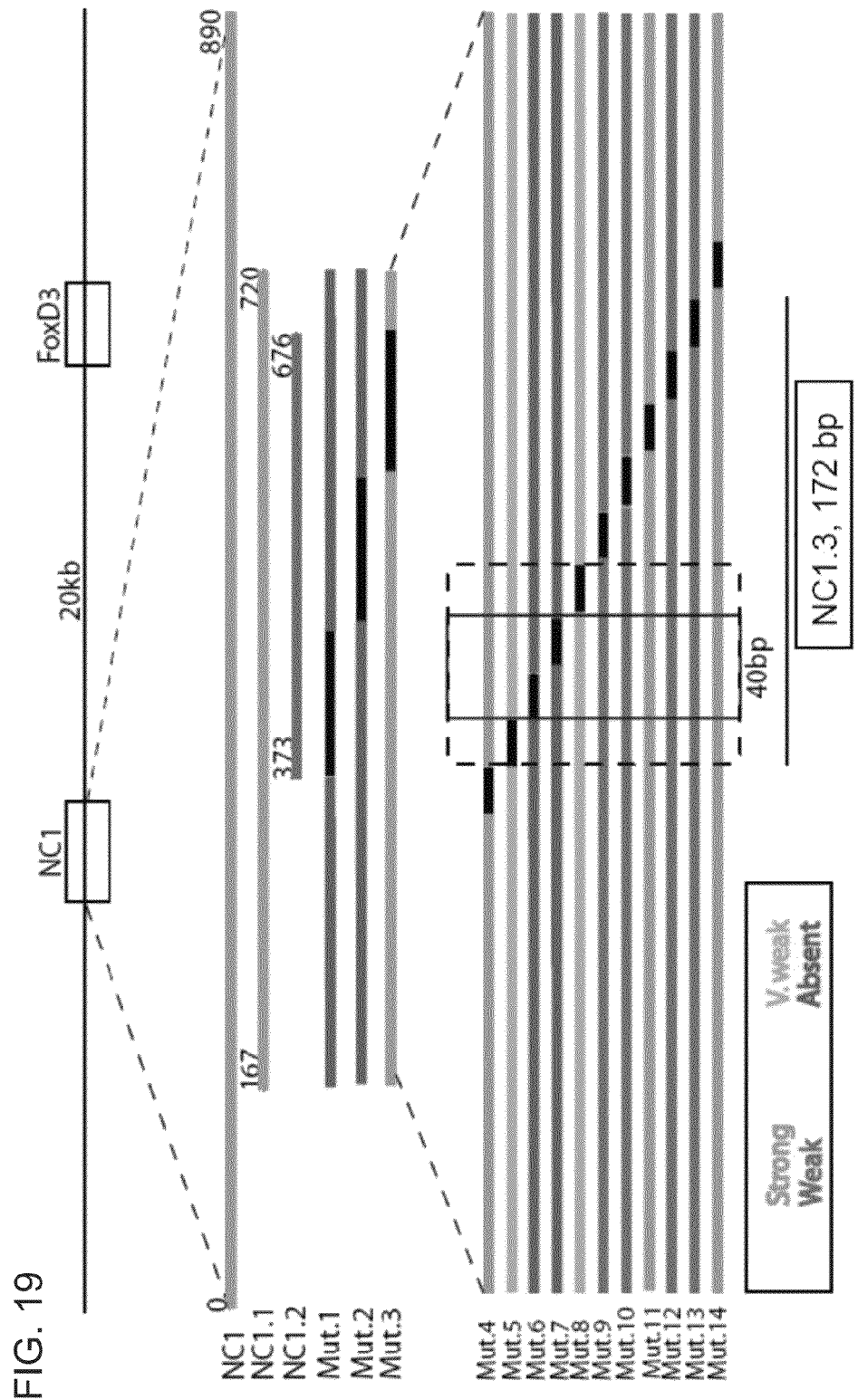
FIG. 19 shows a schematic of the sequence dissection of the NC1 enhancer region.

To reduce the size of NC1 (SEQ ID NO: 4) and NC2 (SEQ ID NO: 5) to the minimal core regions, primers (Table 1) were designed to remove portions from the ends of the enhancers. The conservation of the enhancers was used as a guide to identify the most important regulatory regions. Using this approach, NC1 (SEQ ID NO: 4) was reduced to a 550 bp fragment referred to as NC1.1 (SEQ ID NO: 7) (FIG. 19) and does not show a loss of activity (FIGS. 20A, 20B). A further deletion to a 300 bp fragment referred to as NC1.2 (SEQ ID NO: 8) (FIG. 19) resulted in weak EGFP expression specifically in the cranial neural crest (FIGS. 20C, 20D), suggesting that the regions at the ends of the 300 bp fragment enhance activity of the enhancer, however the critical regions are present within the 300 bp fragment. The core 300 bp NC1.2 fragment (SEQ ID NO: 8) was further analyzed by substituting 100 bp regions of sequence within the larger 550 bp fragment. This analysis revealed that 200 bp was required for expression of the enhancer. 20 bp blocks were substituted across this region, and a region of 80 bp was found that was critical for detectable expression of EGFP shown in Mut.7, Mut.8 (FIGS. 20E-20H). A further 80 bp region was required as a unit for EGFP expression, however the individual 20 bp regions within this secondary region when substituted only resulted in weakened EGFP expression. (Mut. 12, FIGS. 20I, 20J). None of the substitutions resulted in expansion of the enhancer-driven expression. The 172 bp fragment (NC1.3) (SEQ ID NO: 9) (FIG. 19) containing the most critical and supportive regions was amplified and electroporated into embryos, and the 80 bp putative core region (NC1.4) (SEQ ID NO: 10) was tested in tandem by placing two copies into the ptkEGFP construct (see Example X). The 172 bp fragment (SEQ ID NO: 9) alone drove very weak expression of EGFP in the neural crest. Two copies of the 80 bp core region (SEQ ID NO: 10) was sufficient to drive EGFP expression in the same pattern as the full-length NC1 enhancer, albeit slightly weaker, suggesting that the 80 bp region contains the core elements essential for activity of this enhancer.

Binding site mutations were made within NC1. Potential transcription factor binding sites within the core region were identified using Rvista, MatInspector and Jasper (FIG. 21A). Mutations were made to these sites by substituting 6-8 bp of the core binding site as shown in Table 2. Mutations to the Ikaros binding site or to the Ets/Zeb binding site did not affect expression of EGFP (FIGS. 21B, 21C), however mutation of the homeodomain site or Ets/Gata site resulted in loss of EGFP expression (FIGS. 21D-21G). Msx1 and Lmx1b are two of the homeodomain proteins expressed in the neural folds prior to expression of FoxD3, and candidates for regulation of FoxD3. Ets1 is expressed specifically in the cranial neural crest just after the onset of FoxD3 expression. We tested whether these genes could be regulating FoxD3 expression by co-electroporating one or more FITC-conjugated morpholinos to knockdown these genes together with an NC1 reporter directing expression of Cherry. There was no effect on the expression of the NC1 enhancer or on endogenous FoxD3 using a morpholino against Ets1 (at 1 or 2 mM).

Dissection of NC2

Figure 22:
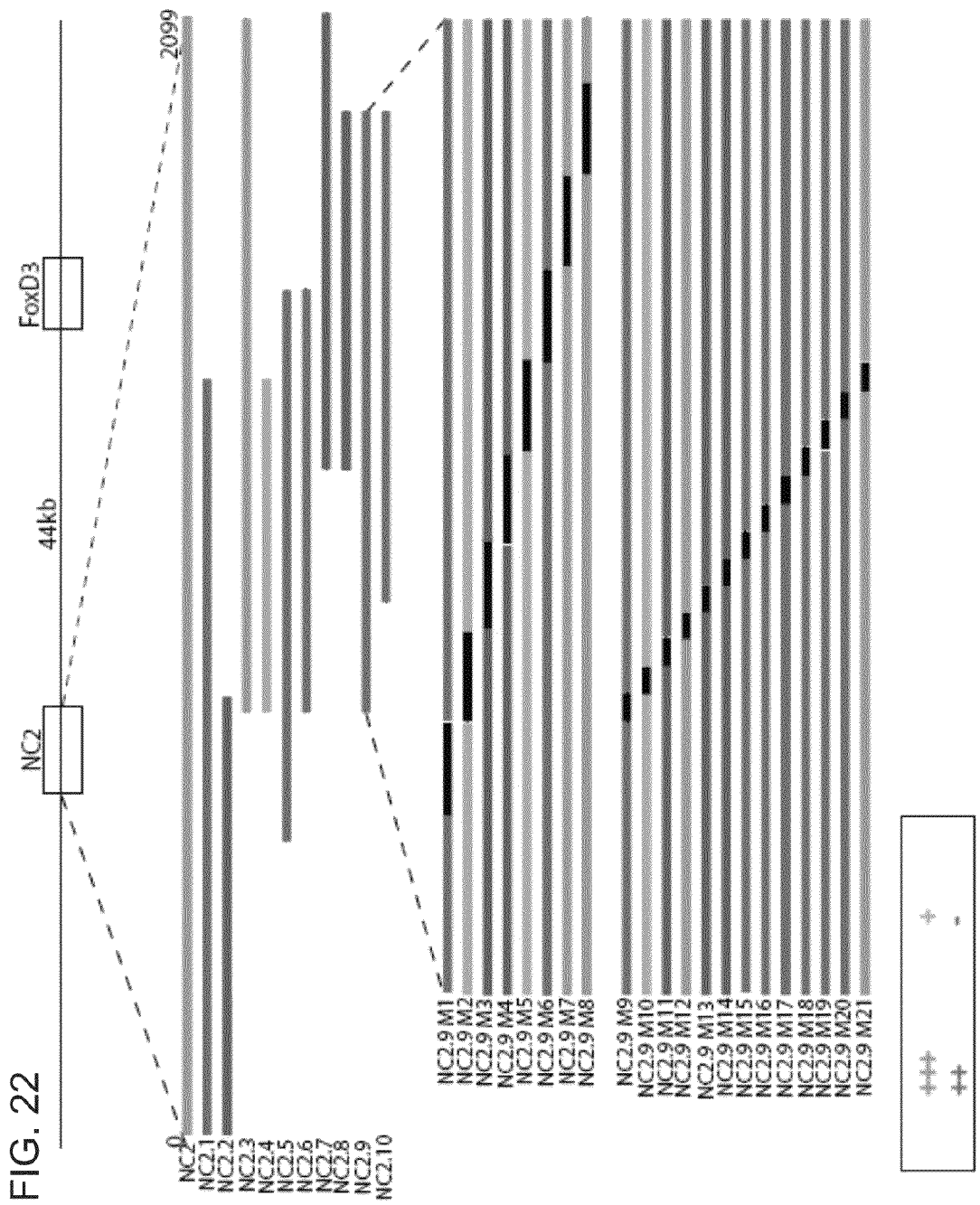
FIG. 22 shows a schematic of the sequence dissection of the NC2 enhancer region.

The NC2 (SEQ ID NO: 5) region was analyzed using the same process of deletions and substitutions as that employed to dissect NC2 (FIG. 22). Interestingly, the most highly conserved region of NC2 was not required for activity of the enhancer, and when tested alone drove no activity. This allowed reduction of the full-length enhancer to a 1339 bp fragment called NC2.3 (SEQ ID NO: 11) (FIG. 22), in which all further analysis was conducted. NC2.4 (SEQ ID NO: 12) is a 600 bp fragment that directs expression in the vagal and trunk neural crest, but not in the cranial migrating crest. 100 bp and 30 bp substitutions within NC2.9 (FIG. 22), isolated from NC2.3 narrowed the required regions of the enhancer activity in the vagal and trunk neural crest to approximately 120 bp, with auxiliary regions on either side of the core being required for strong expression.

FIG. 23 shows a chart summarizing the EGFP expression when "driven" by various NC1 and NC2 subfragments and mutations as indicated.

As shown in FIGS. 17-22, NC1, NC2 and SC1 regulate stages of FoxD3 expression. In one embodiment, NC1, NC1.1, NC1.2, NC1.3 or NC1.4 (SEQ ID NOS: 4, 7-10) is used as a vector expression "driver" to identify cells or manipulate in vivo expression (e.g. gene knockdowns using miRNA, morpholinos, etc) at stages HH8-HH14. In another embodiment, NC2 (SEQ ID NO: 5) is used as a vector expression "driver" to identify cells or manipulate in vivo expression at stages HH9-HH24. In another embodiment, SC1 (SEQ ID NO: 6) is used as a vector expression "driver" to identify cells or manipulate in vivo expression at stages HH8-HH24. Cells or in vivo expression can be identified or monitored using a number of methods known in the art—e.g. the "driven" or activated expression can be of any protein that can be monitored. As shown herein, the EGFP and RFP proteins are expressed and the fluorescence is imaged. The enhancer sequences can "drive" the expression of any protein that can be monitored via specific antibody to the protein, or an antibody to a tag fused with the protein. Fluorescent expression allows for the utilization of flow cytometry to specifically isolate and sort those cells which are able to activate the particular enhancer region, from those which cannot.

Binding Sites in the Enhancer Regions of SEQ ID NOS 1-12

The presence of transcription factors and their ability to bind a DNA site is the mechanism for activating an enhancer region that then subsequently activates expression of an endogenous gene or expression protein in a vector construct. Specific manipulation of the binding sites, which are commonly 6 basepairs in length, indicates that a one base pair mutation within the six, does not disrupt transcription factor binding. However, two or more mutations within 6 basepairs, (in a transcription factor binding site), has shown disrupted reporter expression, due to the inability for the transcription factor to bind. Accordingly, in one embodiment, an enhancer region is provided having a DNA sequence of any one of SEQ ID NOS: 1-12 or a DNA sequence of any one of SEQ ID NOS: 1-12 having one or more nucleotide mutations, but no more than one mutation within any 6 consecutive nucleotides. More than one nucleotide mutation in a region outside of a transcription factor binding site does not disrupt reporter expression.

As mentioned previously, early naive cells contain regulatory factors characteristic of multipotent tissue and are, thus, competent to switch on a neural crest-like transcriptional program in response to the proper signal inputs. Accordingly, in one embodiment, an enhancer region of the present invention (any one of SEQ ID NOS: 1-12) is utilized in early uncommitted cells to induce neural crest traits. The early uncommitted cells are any cells sharing similar neural crest develop, e.g. human, mouse, rat, avian.

Short-hairpin RNA

The critical issue with short-hairpin vectors is that their constitutive expression driving high copy numbers within a cell which, following splicing, results in large numbers of MiR vector arms saturating the cell transcriptional machinery. To control this, in one embodiment, a short-hairpin miRNA system is disclosed wherein short hairpins are generated at lower, but still effective levels and whose expression is limited to a specific time and location within the developing embryo. This offers the further advantage of addressing more specific questions on the role of a particular gene at a particular time or location during development.

Figure 24B:
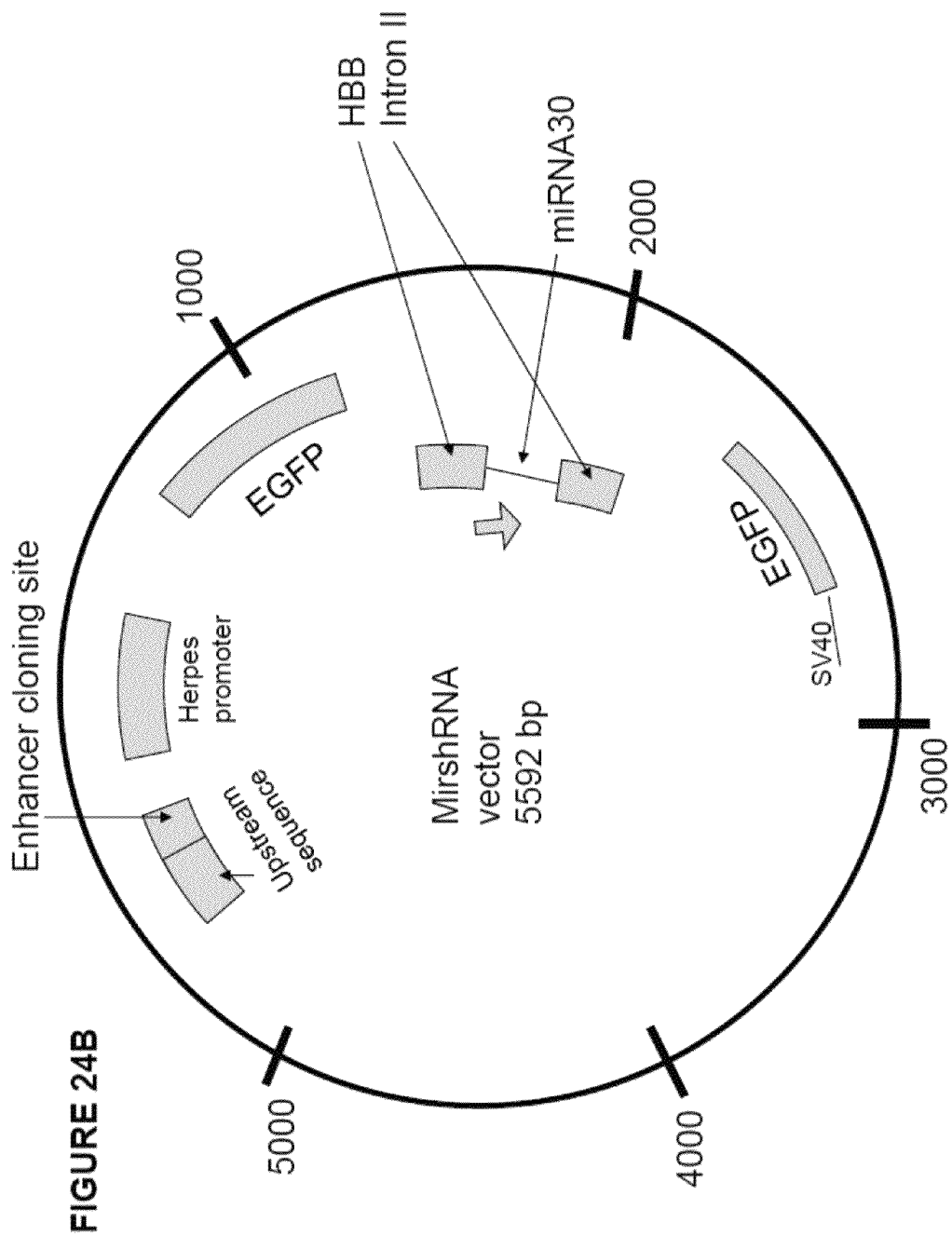
FIG. 24B shows short-hairpin miRNA vector with human beta globin introns surrounding the miRNA cloning site and an empty cloning site for an enhancer sequence.

In FIGS. 24A, 24B two alternative vectors are shown. The vector of FIG. 24A provides a strong knockdown of (down-regulation of) gene expression with moderate EGFP expression, and the miRNA vector of FIG. 24B which is used in parallel with the EGFP as a tracer, gives a strong EFGP signal but with weaker knockdown. The example vector shown here combines the NC1 (SEQ ID NO: 4) enhancer driving expression of a short hairpin RNA designed against Sox10 ('FoxD3-shSox10') or against RFP ('FoxD3-shRFP') for control. This is expressed in the pre-migratory cranial neural crest from approximately 4 somite stage to the 10 somite stage. The EGFP expression (FIGS. 27A, 27B) and mRNA expression patterns observed with in situ hybridization for each vector (FIGS. 26A, 26B). The same knockdown was analysed by QPCR (FIG. 26C). The loss of Sox10 expression on the targeted side is apparent in shSox10 vectors but not in shRFP control vectors. FIG. 26D shows in situ hybridization of Sox10 mRNA.

Proof of specificity is the major test for any method of gene knockdown. To demonstrate that no non-targeted genes are affected by the expression of the vector, RNA was extracted from control and electroporated sides of embryos expressing either FoxD3(NC1)-shSox10 or FoxD3 sh-RFP. Following cDNA synthesis, QPCR was performed for a panel of 3 related neural crest specifier genes—FoxD3, Sox9 and MSX. Sox9 and MSX levels are unaffected by introduction of either vector, demonstrating that the loss of Sox10 was not due to uncontrolled side effects within the early embryo. The loss of FoxD3 is caused by feedback and cross-regulation with Sox10, indicating that Sox10 is necessary for the maintained expression of FoxD3 within the embryo.

An analysis comparing the use of existing pRFPRNAi vectors (Das et al 2006) to morpholinos was performed by (Mende et al 2008) who observe that sh-MiR vectors cause many non-specific defects and recommend against using these in early embryos. These non-specific effects include both ectopic and loss of expression of non-targeted genes. It was found that, irrespective of the gene targeted, these vectors disrupted otic cup morphology and caused loss of otic markers such as Pax2. As a further control for specificity, we performed in situ hybridization on embryos expressing the FoxD3premigratory-shSox10 vector. We find that otic cup morphology and Pax2 expression is unaffected in the electroporated half compared to the non-electroporated control.

Although short hairpin based RNA interference vectors exist for avian model systems (Das et al. 2006) their use in early development has been limited by non-specific effects resulting from constitutive expression and high expression levels. These compromise the accuracy of our understanding of gene function gained by studying the knockdown. For these reasons, a vector system where targeted knockdown can be controlled to endogenous levels and locations using enhancer activity is advantageous. This offers a significant improvement on existing vectors.

Isolating Neural Crest Cells Using Neural Crest Enhancer DNA Fragments

In one embodiment, a method for isolating a specific Hamburger and Hamilton stage or stages of neural crest cells using enhancer DNA of the present invention as the driver for EGFP expression in a vector. After electroporation of the enhancer activated EGFP vector into the chick embryos, embryonic neural crest cells having the stage-specific enhancer binding proteins will activate the EGFP, and these cells can be isolated by flow cytometry as further described in the Examples.

Infection of Sox10 and FoxD3 Enhancers into Human Embryonic Stem (ES) Cells

Sox10E (SEQ ID NO: 1) and NC1 (SEQ ID NO: 4) were both separately subcloned into an RFP lentiviral vector. Human embryonic stem (ES) cells were infected with each vector separately, differentiated into neural crest fate and imaged by microscopy for RFP expression. Both NC1 (FIG. 28A) and Sox10E (FIG. 28B) were activated to direct RFP expression in those cells. The enhancers of the present invention function in human cells. Given the stage-specificity of the enhancers as disclosed herein, an enhancer construct of the present invention subcloned into human cells would allow for identification and isolation of cells corresponding to the stage(s) represented by the enhancer region. In one embodiment, enhancers of the present invention are used to identify early stage cells. In another embodiment, enhancers of the present invention are used to identify early stage human cells. In another embodiment, enhancers of the present invention are used to induce neural crest traits with directed differentiation in early stage uncommitted cells.

Conservation and Function of Homologous Sequences Across Species

As discussed and shown herein, the Sox10 and FoxD3 enhancers and their subfragment sequences (SEQ ID NOS: 1-12) are conserved across several species. It has been shown previously that enhancer sequences from one species can replace endogenous enhancers of another species, as reported in Abbasi et al., 2007, *PLoS ONE*, 2(4): e366. Homologous sequences are known to function in vivo across species as shown herein (FIGS. 28A, 28B) and as reported in Jiang et al. 2009, *Stem Cells Dev.* 18(7): 1059-1070). Thus, the chick embryonic enhancer sequences as described herein are not limited to in vivo function in the chick embryo, and can be utilized in other organisms, including, but not limited to, human, mouse, rat, opossum, zebrafish and *xenopus*.

Accordingly, in one embodiment, an isolated DNA sequence is provided, wherein the sequence has at least 60% homology to one selected from the group consisting of SEQ ID NOS: 1-12. In another embodiment, an isolated DNA sequence is provided, wherein the sequence has at least 70% homology to one selected from the group consisting of SEQ ID NOS: 1-12. In another embodiment, an isolated DNA sequence is provided, wherein the sequence has at least 80% homology to one selected from the group consisting of SEQ ID NOS: 1-12. In another embodiment, an isolated DNA sequence is provided, wherein the sequence has at least 90% homology to one selected from the group consisting of SEQ ID NOS: 1-12. In another embodiment, an isolated DNA sequence is provided, wherein the sequence has at least 95% homology to one selected from the group consisting of SEQ ID NOS: 1-12

EXAMPLES/METHODS

Figure 1:
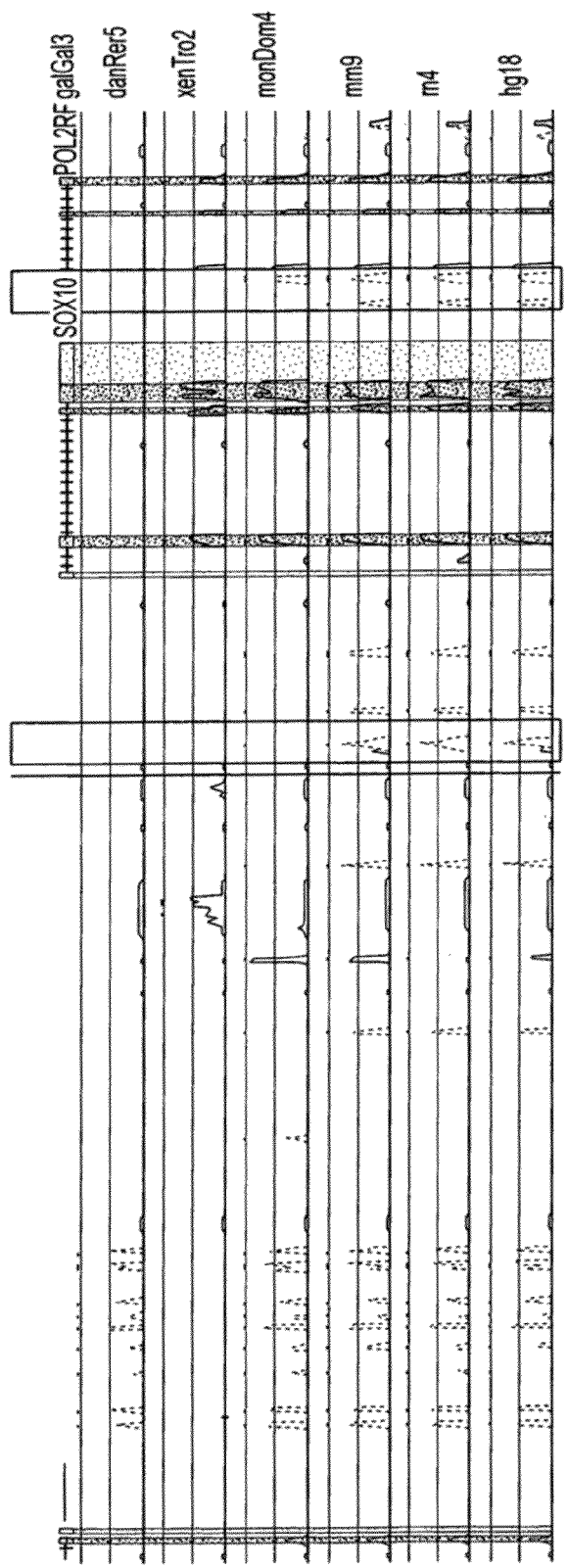
FIG. 1 shows a schematic diagram of comparative genomic analysis surrounding the SOX10 gene in chicken, zebrafish, Xenopus, opossum, mouse, rat and human genomes.

Comparative genomic analyses and cloning of Sox10 and FoxD3 regulatory regions. Highly conserved genomic regions were identified using ECR browser. Binding motifs were predicted using Jaspar database and P-Match program from Transfac database. FIGS. 1 and 17 show a schematic diagram showing comparative genomic analysis using ECR browser.

In FIG. 1, chicken, zebrafish, *Xenopus*, opossum, mouse, rat and human genomic sequences were compared between Sox10 and neighboring genes, Slc16A8 and PolR2F. Red peaks=highly conserved elements; blue=coding exons; green=transposable elements and simple repeats. Boxed Sox10 putative regulatory regions L8(L=late) and E(E=early) show activity in neural crest. UTRs shaded in yellow.

FIG. 17 shows the genomic region of chicken FoxD3 compared to other vertebrates using the UCSC and Rvista programs. The genomic region analyzed was 160 kb, from the 3' end of the Atg4C gene immediately upstream of FoxD3, to the start of the Alg6 gene immediately downstream Regions that were conserved across most or all vertebrates were identified and primers were designed to amplify the conserved regions from BACs CH261-166E22 and CH261-100C15. The primers used to amplify these regions and further dissect these regions, are shown in Table Y. The amplified regions were directionally cloned into the ptkEGFP vector (Uchikawa et al., 2003) donated by H. Kondoh, Osaka University, Japan) using KpnI and XhoI sites.

In general, putative regulatory regions were amplified with Expand High Fidelity Plus (Roche, Indianapolis, Ind.), from chicken BAC DNA (BACPAC, Oakland, Calif.) and cloned into the ptk-EGFP vector (Uchikawa et al. (2003) *Dev Cell* 4(4):509-519). Sox10 and FoxD3 genomic regions were amplified with the Expand High Fidelity Plus PCR System using BAC DNA clones as the template (Chicken BAC library Chori 26). Each fragment, ranging from ~3 kb-5 kb in size, was cloned into the SmaI-linearized ptk-EGFP vector. The ptk-EGFP reporter vector has the Herpes simplex virus thymidine kinase basic promoter upstream of enhanced GFP and was a kind gift of Dr. Hisato Kondoh. The clones with the appropriate orientation were identified by colony PCR and sequenced. The plasmid DNA of the correct clones was prepared and purified using the Endo-free maxi kit (Qiagen) and eluted in EDTA-free buffer.

ptk-Cherry and pCI H2B-RFP plasmids were generated for use in this study. ptk-Cherry reporter vector was made by swapping EGFP with Cherry fluorescent protein in the ptk-EGFP reporter vector (Uchikawa et al. (2003) *Dev Cell* 4(4): 509-519). pCI H2B-RFP, a tracer construct that yields ubiquitous expression under the control of chicken beta actin promoter is a bicistronic vector allowing for exogenous expression of proteins of interest and of a fusion protein of human histone 2B and monomeric RFP protein, translated from the IRES. The pCI H2B-RFP construct was made by replacing the 3×NLS-EGFP sequence within the pCI-GFP vector (Megason S G & McMahon A P (2002) *Development* 129(9):2087-2098) with the H2B-mRFP1 sequence.

In situ hybridization. Whole-mount in situ hybridization was performed using a procedure previously described (Wilkinson D G (1992) *In situ Hybridization: A Practical Approach*, ed Wilkinson DG (IRL Press, Oxford), pp 75-83). Whole mounts were imaged using microscope and Axiovision camera and software. Fluorescent in situ procedure using GFP probe was adapted from (Acloque and Nieto (2008) *Methods Cell Biol* 87:169-185). Whole-mount in situ hybridizations were performed using a procedure previously described (Antonellis A. et al. (2008) *PLoS Genet* 4(9):e 1000174). Fluorescent in situ procedure using GFP probe was adapted from (Dutton et al. (2008) *BMC Dev Biol* 8:105. With the exception of the Sox9 and Sox10 probes, which were prepared using full length cDNA constructs (a gift from Yi-Chuan Cheng) (Cheng et al. (2000) *Brain Res Dev Brain Res* 121(2): 233-241), as a template, all other digoxigenin-labeled antisense RNA probes, were prepared from chicken EST clones obtained from (ARK Genomics and MRC geneservice). Sox10 template was digested with HindIII, while all EST clones were linearized using NotI restriction enzyme. All antisense RNA probes were synthesized using T3 RN A polymerase, according to standard protocols. FIG. 3B shows that at HH8+, GFP transcripts are detected by fluorescent in situ hybridization in cranial neural crest (CNC) similar to endogenous Sox10 expression (FIG. 3G). Distribution of EGFP transcripts (FIGS. 3C, 3D, 3E; HH9+; HH12, H15, respectively) is similar to endogenous Sox10 in FIGS. 3H-3J, respectively. FIG. 3D shows EGFP expression at HH12 in rhombomere5 stream surrounding the otic vesicle(OV) resembles endogenous Sox10 (FIG. 3I), but is missing in vagal neural crest (VNC). (FIG. 3F). Cross section of embryo in FIG. 3D shows specific Sox10E regulatory activity in CNC around optic vesicle(OpV). (FIGS. 3G-3J) show endogenous Sox10 expression at HH8+–HH15.; (OP is otic placode).

Ex ovo and in ovo electroporations. Chicken embryos were electroporated at stages HH4-HH8 to target the cranial neural crest cell population and at stages HH10-12 to target vagal and/or trunk neural crest cells following previously described electroporation procedures (Sauka-Spengler and Barembaum (2008), *Methods Cell Biol* 87:237-256). In ex-ovo experiments, the DNA plasmid constructs (enhancer driven reporter with ubiquitously-expressing tracer) were introduced in the entire epiblast of the early chicken embryo, while in in-ovo electroporations only one half of the neural tube received the DNA. Injected DNA plasmid concentrations were as follows: 2 μg/μl of ptk-EGFP or ptk-Cherry reporter construct, containing each of Sox10 or FoxD3 putative cis-regulatory regions or the Sox10E2, NC1, NC2 and SC1 mutated versions, combined with 1 μg/μl of either tracer (pCI H2B-RFP) or expression constructs (Sox9-pCI H2B-RFP or Ets1-pCI H2B-RFP).

Microscopy and immunohistochemistry. The electroporated embryos were collected at different stages, fixed in 4% paraformaldehyde O/N and then washed three times in PBS at room temperature. A Zeiss axioskop2 Plus fluorescence microscope equipped with the AxioVision software was employed to image the embryos. Images were processed using Adobe Photoshop CS2. After imaging, embryos were cryo-protected in two steps: 15% sucrose/PBS and 7.5% gelatin/15% sucrose/PBS, equilibrated and mounted in 20% gelatin/PBS and frozen in liquid nitrogen. 12 μm cryosections were collected on Super Frost Plus slides (Fischer Scientific, Pittsburgh, Pa.) and de-gelatinized for 2×10 minutes at 42° C. in PBS. To intensify EGFP signal, the sections were washed 4× in PBS for 5 minutes, blocked for 1 hour in 10% Donkey serum/PBTW (PBS/0.1% Tween-20) and stained with 1:1000 anti-GFP primary antibody (Abeam Inc., Cambridge, Mass.) followed by 1:2000 Donkey anti-goat Alexa-Fluor 488-conjugated secondary antibody (Molecular probes). Sections were subsequently washed, cover slipped and imaged using the same imaging procedure described for the in situ wholemounts.

Dissection of Sox10 downstream putative regulatory region and mutation of candidate binding sites. The 3.5 kb genomic region downstream Sox10 coding (Sox10E) was divided into smaller regions, dissected and mutated fragments amplified using Expand High Fidelity Plus PCR System (Roche Applied Science, Indianapolis, Ind.). For the initial dissection of the Sox10E fragment, the following primers were used:

```
Sox10E1_5',
                                     (SEQ ID NO: 19)
5'-ATTAGGTACCTCTGATACAGATGCAAGGCTG-3'

Sox10E1_3',
                                     (SEQ ID NO: 20)
5'-TAATCTCGAGAATTTGCAGCACTGTGGCCTT-3';

Sox10E2_5',
                                     (SEQ ID NO: 21)
5'-AATTGGTACCGGCAAGAGTGGCAATTTAACC-3'

Sox10E2_3',
                                     (SEQ ID NO: 22)
5'-ATTACTCGAGATTGCTTCCCCCTAGACAGTT-3';

Sox10E3_5',
                                     (SEQ ID NO: 23)
5'-TTTTGGTACCTAACCAGGGAGGAGTTGTGG-3'

Sox10E3_3',
                                     (SEQ ID NO: 24)
5'-AATTCTCGAGAAGGCCCACAGCAGAGTG-3'.
```

To perturb candidate binding sites within the Sox10E2 fragment, we used single or fusion PCR as previously described (Nikitina N, Sauka-Spengler T, & Bronner-Fraser M (2008) *Proc Natl Acad Sci USA* 105(51):20083-20088; Sauka-Spengler T & Bronner-Fraser M (2006) *Curr Opin Genet Dev* 16(4):360-366).

The primers having mutations are listed here. Mutated regions are underlined, the mutated nucleotides are shown in bold and fusion primer sequences are italicized:

```
First 2 Pax sites clusters (M1, M3)_5',
                                     (SEQ ID NO: 25)
5'-AATTGGTACCGGCAAAGCCCATG-ATTTAACCTACAACTGCTGAGCTTGTAGGA

AGCCCATGGGCGACTGTGCTTCCGGCT-3';

Myb (M2)_5',
                                     (SEQ ID NO: 26)
5'-ATTAGGTACCTGGCAAGAGTGGCAAGGGATGGACTGGTAGATGGAAGTGTAGGACTGTGACTGGCGA-3';

Second 2 Pax cluster sites (M5, M7)_3',
                                     (SEQ ID NO: 27)
5'-TCCCTGCTCCTGCTGCTTATCATGGGCTGGGATCCCCTTTCATGGGCTCTGCCCCAGCCGGAAGCACAGT-3';

Ets/Elk (M4)_5',
                                     (SEQ ID NO: 28)
5'-ATTAGGTACCTGGCAAGAGTGGCAATTTAACCTACAACTGCTGAGCTTGTAGGACTGTGACTGGCGACTGT

ATGGTTAATTGGGGCAGTGCCACTGAAA-3';

NFKB1 (M6)_3',
                                     (SEQ ID NO: 29)
5'-TGCTGCTTATCAGTGATGAGCCCATGGTCTCAGTGGCACTGCCCCAG3';

Lef/Tcf/SoxE (M8)_3',
                                     (SEQ ID NO: 30)
5'-TCTCATCAAATCACCTCCATCTACCCTGCTCCTGCTGCTTATCAGT-3';

Ets (M9) 3',
                                     (SEQ ID NO: 31)
5'-AATTCTCGAGATTGCTTCCCCCTAGACAGTTGGGCCTTTGTGCCCTGAGCAGGTTGCTGTGGAAACCCCCAAT

GGGCTCTCTGGCCAGAGCTGGCT-3';
```

-continued

NFKB1/Lef/Tcf/Ets1_3',
(SEQ ID NO: 32)
5'-AATTCTCGAGTTGCTTCCCCCTAGACAGTTGGGCCTTTGTGCCCTGAGCAGGTTGCTGTGGAGCCCATGGTC

TTCCTCTCTGGCCAGAGC-3';

SoxE/Lef/Tcf (M10)_3',
(SEQ ID NO: 33)
5'-ATTACTCGAGATTGCTTCCCCCTAGACAGTTGGGCGTATGCGCCCTGAGCAGGTTGCTGTGGAAA-3';

Myb (M11)_3',
(SEQ ID NO: 34)
5'-ATTACTCGAGATTGCTTCCCCCTACTCCATAAGGCCTTTGTGCCCTGAGCA-3';

SoxD (M12)_3',
(SEQ ID NO: 35)
5'-ATTACTCGAGGCCAATTCCCCCTAGACAGTTGGGC-3';

Δ1_3',
(SEQ ID NO: 37)
5'-*AATTTCCTCTCTGGCCAGA* AAATCACCTATTGTTTCCCT-3';

R1_3',
(SEQ ID NO: 37)
5'-AATTTCCTCTCTGGCCAGCCTCGGGGTACATCCGCTCGGAGGAGGCCTCCCAGCCCATCGTCT

AAATCACCTATTGTTTCCCT-3'.

After PCR amplification, each fragment was purified using PCR product purification kit (Qiagen) and cloned into KpnI/XhoI digested ptk-EGFP or ptk-Cherry reporter vectors.

Dissection of Sox10E reveals two regulatory regions that function in a specific spatiotemporal manner: Sox10E2 is activated as cranial neural crest cells delaminate whereas Sox10E1 is activated in later migrating vagal and trunk neural crest. As shown in FIG. 4A, Sox10E1 displays no activity in the delaminating cranial neural crest. FIG. 4B shows Sox10E2 activity at HH15 persists in the periocular crest and otic vesicle, but also within the first two branchial arches, which lack endogenous Sox10; Sox10E2 is not expressed in vagal neural crest at this stage or later, at HH18 shown in FIG. 4C, and in either the vagal or trunk regions (FIGS. 4D-4F). Panels corresponding to (4A-4C), respectively, show expression of the co-electroporated tracer pCI H2B-RFP to locate cells that received both tracer and reporter EGFP plasmid DNA.

Sox10E contains distinct spatiotemporal regulatory elements: Sox10E2 in delaminating CNC and Sox10E1 in later migrating vagal (VNC) and trunk neural crest. FIG. 5A Schematic diagram representing dissection of Sox10E fragment, located ~1 kb downstream of Sox10 locus (UTR in yellow). Two smaller active regulatory fragments embedded within Sox10E, (Sox10E1&E2) each contain a conserved region(red bar) with 70% sequence homology between amniotes. (FIG. 5B) Sox10E2 drives expression in delaminating CNC(arrows) at HH8+; Sox10E11 is first active in migrating VNC at HH15 (FIG. 5C). (FIG. 5D) Sox10E1 activity persists in migrating VNC, trunk neural crest (arrow), and branchial arches 3-5(arrowhead). (FIG. 5E) Table 11 summarizes distinct temporal (HH9-18) and spatial (cranial/vagal/trunk) regulatory activity of Sox10E1&E2. Red-=no expression; green+=EGFP reporter expression.

Dissection of the Sox10E2 fragment reveals an essential core and auxiliary region important for optimal enhancer activity. FIG. 6A shows a magnified image showing the region Sox10E2 from the genomic comparative analysis illustrated in FIG. 4A. Each uncolored peak represents the conserved region equivalent to region Sox10E2 in chicken for each corresponding species. Inside the conserved regions, the red patches represent highly conserve portions (85%-90% each 30 bp). The order of species from top to bottom: mouse, dog, opossum, rat, chimpanzee and human. FIG. 6B shows a schematic diagram representing the different successive deletions (dotted lines) that were performed, guided by bioinformatics, to identify the main core element responsible for the regulatory activity of the Sox10E2 fragment. The horizontal black lines represent different fragments. Red portion of the lines denote a 160 bp region (referred to as essential core element), highly conserved between dog, chimpanzee and human, capable of producing weak tissue-specific regulatory activity in delaminating cranial neural crest cells. The gray arrow points to a non-conserved 59 bp-long auxiliary region, necessary for achieving strong regulatory activity of the enhancer. CNC, cranial neural crest.

Transcriptional inputs into the Sox10E2 regulatory region. FIG. 7A shows a schematic diagram showing sequence alignment of 264 bp Sox10E2 regulatory region; essential core region shaded in yellow. Colored frames indicate computationally identified putative transcription factors binding motifs. Mutations M1-M13 were replaced by random sequences. Faded sequence shows a 45 bp region deleted or replaced by mCherry coding sequence. Highlighted in blue are conserved nucleotides within putative binding motifs. Single dashed lines indicate no bases in aligned sequence. Thick dashed lines indicate nonalignable sequences. Thick solid underlines delineate Sox10E2 subfragments used in EMSA and pulldown assays. Sox10E2-driven EGFP expression in CNC (FIG. 7B) is abolished upon mutation of an Ets1 binding motif (FIG. 7C), but only decreased after mutation of putative SoxD motif (FIG. 7D), and not affected by simultaneous mutation of four putative Pax sites(FIG. 7E). Simultaneous inactivation of SoxE, Ets and Myb binding sites (M2, M8,M9,M11,M12) within a much larger genomic region abolishes reporter expression in delaminating CNC (FIG. 7F).

Dissection of FoxD3 NC1. NC2 and SC1 Regions

Enhancer substitutions and mutations: regions of NC1 and NC2 were replaced with EGFP coding sequence using fusion PCR. For 100 bp substitutions, the region of EGFP used was (SEQ ID NO: 38)(tggagtacaactacaacagccacaacgtctatatcatggccgacaagcagaagaacggcatcaaggtgaacttcaagatccgccacaacatcgaggacgg): for 20 bp substitutions (SEQ ID NO: 39)(tggagtacaactacaacagc), and for 30 bp substitutions (SEQ ID NO: 40) (acaagcagaagaacggcatcaaggtgaact). Amplified fusion constructs were cloned into ptk-EGFP vector (Uchikawa et al., 2003) and sequenced to ensure no additional mutations were present. Binding sites were identified using Jasper. RVista and MatInspector databases and programs. Sites were mutated by substituting 6-8 adjacent critical base pairs with GFP coding sequence, using fusion PCR and cloning into ptkEGFP. Mutated enhancer constructs were electroporated into stage 4 embryos as described herein and analyzed for expression of EGFP and RFP at stages 8-12.

TABLE 1

Text in capitals indicates enhancer sequence, and text in small letters indicates replacement GFP sequence. To make the mutated constructs, mutated primers were paired with flanking primers (NC1.1 or NC2.9), amplified and joined in a fusion PCR reaction using the flanking primers.

| Primer Name | | Primer Sequence |
|---|---|---|
| NC1 fwd | (SEQ ID NO: 41) | AGGCAATGCAGCGAATGACC |
| NC1 rev | (SEQ ID NO: 42) | GACCTGGCTCCCTTTGAGAC |
| NC1.1 fwd | (SEQ ID NO: 43) | CAGTAAGCTTTCCACCAACA |
| NC1.1 rev | (SEQ ID NO: 44) | GTTTAACATACACTATCCAATG |
| NC1.2 fwd | (SEQ ID NO: 45) | CCTGAAGCTCATTAGATATT |
| NC1.2 rev | (SEQ ID NO: 46) | CCGACATTTGGGAAATTAAA |
| NC1.3 fwd | (SEQ ID NO: 47) | CATTAGATATTCCCTGG |
| NC1.3 rev | (SEQ ID NO: 48) | AAAGAGGCCAGTAATTGTC |
| NC1 80 bp core fwd | (SEQ ID NO: 49) | CATTAGATATTCCCT |
| NC1 80 bp core rev | (SEQ ID NO: 50) | CCCACAGAGATTGCT |
| NC1.1 Mut 1 fwd | (SEQ ID NO: 51) | caagcagaagaacggcatcaaggtgaacttcaagatccgccacaacatcgaggacggGAGACTCTCCT |
| NC1.1 Mut 1 rev | (SEQ ID NO: 52) | gatgccgttcttctgcttgtcggccatgatatagacgttgtggctgttgtagttgtactccaAAACCCACTGAA |
| NC1.1 Mut 2 fwd | (SEQ ID NO: 53) | caagcagaagaacggcatcaaggtgaacttcaagatccgccacaacatcgaggacggACTTAAGCTAAATGG |
| NC1.1 Mut 2 rev | (SEQ ID NO: 54) | gatgccgttcttctgcttgtcggccatgatatagacgttgtggctgttgtagttgtactccaCTCCTATTGGCA |
| NC1.1 Mut 3 fwd | (SEQ ID NO: 55) | caagcagaagaacgg catcaaggtgaacttcaagatccgccacaacatcgaggacggCGGATTTTGGTG |
| NC1.1 Mut 3 rev | (SEQ ID NO: 56) | gatgccgttcttctgcttgtcggccatgatatagacgttgtggctgttgtagttgtactccaCGATTAATGTAACTC |
| NC1.1 Mut 4 fwd | (SEQ ID NO: 57) | agtacaactacaacagcCATTAGATATTCC |
| NC1.1 Mut 4 rev | (SEQ ID NO: 58) | tgttgtagttgtactccaAAGAATTCTCTTTT |
| NC1.1 Mut 5 fwd | (SEQ ID NO: 59) | agtacaactacaacagcATTCTCCTAAGTA |
| NC1.1 Mut 5 rev | (SEQ ID NO: 60) | tgttgtagttgtactccaAGCTTCAGGAAA |
| NC1.1 Mut 6 fwd | (SEQ ID NO: 61) | agtacaactacaacagcTAACAGGATTTTC |
| NC1.1 Mut 6 rev | (SEQ ID NO: 62) | tgttgtagttgtactccaATAGGCCAGGGA |
| NC1.1 Mut 7 fwd | (SEQ ID NO: 63) | agtacaactacaacagcGAGCAATCTCTG |
| NC1.1 Mut 7 rev | (SEQ ID NO: 64) | tgttgtagttgtactccaTAAAATCTAATTACTTAG |
| NC1.1 Mut 8 fwd | (SEQ ID NO: 65) | agtacaactacaacagcAATAGGAGACTC |
| NC1.1 Mut 8 rev | (SEQ ID NO: 66) | tgttgtagttgtactccaTGATCTGTTGAAA |
| NC1.1 Mut 9 fwd | (SEQ ID NO: 67) | agtacaactacaacagcTCTGGCCTTACC |
| NC1.1 Mut 9 rev | (SEQ ID NO: 68) | tgttgtagttgtactccaCCCACAGAGATT |
| NC1.1 Mut10 fwd | (SEQ ID NO: 69) | agtacaactacaacagcAGCATGGATAAC |
| NC1.1 Mut 10 rev | (SEQ ID NO: 70) | tgttgtagttgtactccaGGGAGAGTCTCCTA |

TABLE 1 -continued

Text in capitals indicates enhancer sequence, and text in small letters indicates replacement GFP sequence. To make the mutated constructs, mutated primers were paired with flanking primers (NC1.1 or NC2.9), amplified and joined in a fusion PCR reaction using the flanking primers.

| Primer Name | | Primer Sequence |
|---|---|---|
| NC1.1 Mut 11 fwd | (SEQ ID NO: 71) | agtacaactacaacagcTGGGAGTTAATAG |
| NC1.1 Mut 11 rev | (SEQ ID NO: 72) | tgttgtagttgtactccaGCCCTGCTGGTAA |
| NC1.1 Mut 12 fwd | (SEQ ID NO: 73) | agtacaactacaacagcACTGGCCTCTTT |
| NC1.1 Mut 12 rev | (SEQ ID NO: 74) | tgttgtagttgtactccaGCCTGGATGTTA |
| NC1.1 Mut 13 fwd | (SEQ ID NO: 75) | agtacaactacaacagcTTACATTAATGCACT |
| NC1.1 Mut 13 rev | (SEQ ID NO: 76) | tgttgtagttgtactccaAATTGTCCTATTAAC |
| NC1.1 Mut 14 fwd | (SEQ ID NO: 77) | agtacaactacaacagcACTTAAGCTAAATG |
| NC1.1 Mut 14 rev | (SEQ ID NO: 78) | tgttgtagttgtactccaAAAGAGGCCAGTA |
| NC2 fwd | (SEQ ID NO: 79) | TGAGTGTGCCTCCATGTGTC |
| NC2 rev | (SEQ ID NO: 80) | GATGGTGCAGCACACGGTTG |
| NC2.1/NC2.4 rev | (SEQ ID NO: 81) | TGTGGTAGGCTTATTGTTTTGCT |
| NC2.2 rev | (SEQ ID NO: 82) | TCGGTTTTGTTTCACAGTTTG |
| NC2.3/NC2.4 NC2.6/NC2.9 fwd | (SEQ ID NO: 83) | GGTGCATAGAACAAACTGTG |
| NC2.5 fwd | (SEQ ID NO: 84) | GCACTGGGTTCATGAAGTTTC |
| NC2.5 rev | (SEQ ID NO: 85) | CTACCTCAGAAGGCATTGTA |
| NC2.7/NC2.8 fwd | (SEQ ID NO: 86) | CGATTCTCTGTCTGCCAATTT |
| NC2.8/NC2.9/ NC2.10 rev | (SEQ ID NO: 87) | GTTCACCCAGTAAACCAGTA |
| NC2.10 fwd | (SEQ ID NO: 88) | TGTCATCTTCCGCTCACTT |
| NC2.9 Mut 1 fwd | (SEQ ID NO: 89) | caagcagaagaacggcatcaaggtgaacttcaagatccgccacaac atcgaggacggGGAAACGATGG |
| NC2.9 Mut 1 rev | (SEQ ID NO: 90) | gatgccgttcttctgcttgtcggccatgatatagacgttgtggctg ttgtagttgtactccaGACATAACTTTGTC |
| NC2.9 Mut 2 fwd | (SEQ ID NO: 91) | caagcagaagaacggcatcaaggtgaacttcaagatccgccacaac atcgaggacggAAATTACTCCGATT |
| NC2.9 Mut 2 rev | (SEQ ID NO: 92) | gatgccgttcttctgcttgtcggccatgatatagacgttgtggctg ttgtagttgtactccaCCAAATACTTTCACT |
| NC2.9 Mut 3 fwd | (SEQ ID NO: 93) | caagcagaagaacggcatcaaggtgaacttcaagatccgccacaac atcgaggacggTAGCAAGGGGCTT |
| NC2.9 Mut 3 rev | (SEQ ID NO: 94) | gatgccgttcttctgcttgtcggccatgatatagacgttgtggctg ttgtagttgtactccaGTATCATTTCAATTAG |
| NC2.9 Mut 4 fwd | (SEQ ID NO: 95) | caagcagaagaacggcatcaaggtgaacttcaagatccgccacaac atcgaggacggCCGCTACCTTCA |
| NC2.9 Mut 4 rev | (SEQ ID NO: 96) | gatgccgttcttctgcttgtcggccatgatatagacgttgtggctg ttgtagttgtactccaCAGCAGCCACTT |
| NC2.9 Mut 5 fwd | (SEQ ID NO: 97) | caagcagaagaacggcatcaaggtgaacttcaagatccgccacaac atcgaggacggGTATTCATCCCCAA |
| NC2.9 Mut 5 rev | (SEQ ID NO: 98) | gatgccgttcttctgcttgtcggccatgatatagacgttgtggctg ttgtagttgtactccaTGGTAGGCTTAT |
| NC2.9 Mut 6 fwd | (SEQ ID NO: 99) | caagcagaagaacggcatcaaggtgaacttcaagatccgccacaac atcgaggacggCAGTAGGAAAAAC |
| NC2.9 Mut 6 rev | (SEQ ID NO: 100) | gatgccgttcttctgcttgtcggccatgatatagacgttgtggctg ttgtagttgtactccaAACACTTATCTCTAC |

TABLE 1 -continued

Text in capitals indicates enhancer sequence, and text in small letters indicates replacement GFP sequence. To make the mutated constructs, mutated primers were paired with flanking primers (NC1.1 or NC2.9), amplified and joined in a fusion PCR reaction using the flanking primers.

| Primer Name | | Primer Sequence |
|---|---|---|
| NC2.9 Mut 7 fwd | (SEQ ID NO: 101) | caagcagaagaacggcatcaaggtgaacttcaagatccgccacaacTatcgaggacggTAGTTCAACTGTG |
| NC2.9 Mut 7 rev | (SEQ ID NO: 102) | gatgccgttcttctgcttgtcggccatgatatagacgttgtggctgttgtagttgtactccaAACCGAGCGCAA |
| NC2.9 Mut 8 fwd | (SEQ ID NO: 103) | caagcagaagaacggcatcaaggtgaacttcaagatccgccacaacatcgaggacggTCAGTGCAATTC |
| NC2.9 Mut 8 rev | (SEQ ID NO: 104) | gatgccgttcttctgcttgtcggccatgatatgacgttgtggctgttgtagttgtactccaGAACTATTTTGGAT |
| NC2.9 Mut 9 fwd | (SEQ ID NO: 105) | gaagaacggcatcaaggtgaactATGGGCAATAAT |
| NC2.9 Mut 9 rev | (SEQ ID NO: 106) | ttgatgccgttcttctgcttgtCCAAATACTTTCA |
| NC2.9 Mut 10 fwd | (SEQ ID NO: 107) | gaagaacggcatcaaggtgaactACCTCCCTGTTA |
| NC2.9 Mut 10 rev | (SEQ ID NO: 108) | ttgatgccgttcttctgcttgtGGCAACCAAACT |
| NC2.9 Mut 11 fwd | (SEQ ID NO: 109) | gaagaacggcatcaaggtgaactGAAATGATACAAAT |
| NC2.9 Mut 11 rev | (SEQ ID NO: 110) | ttgatgccgttcttctgcttgtCATGACTTTTTTG |
| NC2.9 Mut 12 fwd | (SEQ ID NO: 111) | gaagaacggcatcaaggtgaactCTGCCAATTTAG |
| NC2.9 Mut 12 rev | (SEQ ID NO: 112) | ttgatgccgttcttctgcttgtAATTAGTTACTAGC |
| NC2.9 Mut 13 fwd | (SEQ ID NO: 113) | gaagaacggcatcaaggtgaactGGTCAAATGAGC |
| NC2.9 Mut 13 rev | (SEQ ID NO: 114) | ttgatgccgttcttctgcttgtACAGAGAATCGG |
| NC2.9 Mut 14 fwd | (SEQ ID NO: 115) | gaagaacggcatcaaggtgaactGTTTGAAGTGGC |
| NC2.9 Mut 14 rev | (SEQ ID NO: 116) | ttgatgccgttcttctgcttgtCTTGACCACAAC |
| NC2.9 Mut 15 fwd | (SEQ ID NO: 117) | gaagaacggcatcaaggtgaactCTTGGTGTGGAC |
| NC2.9 Mut 15 rev | (SEQ ID NO: 118) | ttgatgccgttcttctgcttgtATAGTTTCATGAAT |
| NC2.9 Mut 16 fwd | (SEQ ID NO: 119) | gaagaacggcatcaaggtgaactCATTACCCCATA |
| NC2.9 Mut 16 rev | (SEQ ID NO: 120) | ttgatgccgttcttctgcttgtCCCCTTGCTATG |
| NC2.9 Mut 17 fwd | (SEQ ID NO: 121) | gaagaacggcatcaaggtgaactCACAGATAGCAA |
| NC2.9 Mut 17 rev | (SEQ ID NO: 122) | ttgatgccgttcttctgcttgtTCCAGAGGAGTC |
| NC2.9 Mut 18 fwd | (SEQ ID NO: 123) | gaagaacggcatcaaggtgaactGCTACCTTCAGC |
| NC2.9 Mut 18 rev | (SEQ ID NO: 124) | ttgatgccgttcttctgcttgtCAGCACTCTCCT |
| NC2.9 Mut 19 fwd | (SEQ ID NO: 125) | gaagaacggcatcaaggtgaactTCTGTGTCAGTC |
| NC2.9 Mut 19 rev | (SEQ ID NO: 126) | ttgatgccgttcttctgcttgtGGTGGTAGGCTT |
| NC2.9 Mut 20 fwd | (SEQ ID NO: 127) | gaagaacggcatcaaggtgaactCTGACCAGGATA |
| NC2.9 Mut 20 rev | (SEQ ID NO: 128) | ttgatgccgttcttctgcttgtGAAGCTTTTGATG |
| NC2.9 Mut 21 fwd | (SEQ ID NO: 129) | gaagaacggatcaaggtgaactTAAGTGTTGTATTC |
| NC2.9 Mut 21 rev | (SEQ ID NO: 130) | ttgatgccgttcttctgcttgtAGGCAGCCACTG |
| SC1 fwd | (SEQ ID NO: 131) | GACAAAGATAACCATCCTCC |
| SC1 rev | (SEQ ID NO: 132) | CACTTCTTCAATTGCTGAGG |
| SC1.1 rev | (SEQ ID NO: 133) | ATAGCAAAGACACATTGTGC |

TABLE 1 -continued

Text in capitals indicates enhancer sequence, and text in small letters indicates replacement GFP sequence. To make the mutated constructs, mutated primers were paired with flanking primers (NC1.1 or NC2.9), amplified and joined in a fusion PCR reaction using the flanking primers.

| Primer Name | Primer Sequence |
| --- | --- |
| SC1.1a rev | (SEQ ID NO: 134) GTGCAGAAATCAACAGCTA |
| SC1.1b fwd | (SEQ ID NO: 135) GGCCATTATGATCTTTAACT |

TABLE 2

| Primer name | Primer sequence |
| --- | --- |
| NC1.1 Ikaros mut. Fwd (SEQ ID NO: 136) | gaCTACAAGAGCcctattctccta |
| NC1.1 Ikaros mut. rev (SEQ ID NO: 137) | aggGCTCTTGTAGtctaatgagctt |
| NC1.1 Ets/Zeb mut. fwd (SEQ ID NO: 138) | ctattTAGAACagtaattagatttta |
| NC1.1 Ets/Zeb mut. rev (SEQ ID NO: 139) | tactGTTCTAaataggccaggga |
| NC1.1 HD mut. fwd (SEQ ID NO: 140) | cctaCTACCACCgattttaacagg |
| NC1.1 HD mut. rev (SEQ ID NO: 141) | atcGGTGGTAGtaggagaatagg |
| NC1.1 Ets/Gata mut. fwd (SEQ ID NO: 142) | ttaaACAACAGCtcaacagatcag |
| NC1.1 Ets/Gata mut. rev (SEQ ID NO: 143) | tgaGCTGTTGTttaaaatctaattac |

The regions that were mutated are indicated by capital letters. Primers were paired with NC1.1 fwd or rev primers in a first round of amplification, then joined in fusion PCR using the flanking NC1.1 fwd and rev primers.

EMSA and Pull-down Assays

EMSA was performed using LightShift Chemiluminescent EMSA Kit (Thermo Scientific, Rockford, Ill.) following manufacturer's instructions. Five Sox10E2 subfragments (M2, M4, M8, M9, M11/M12) and three control fragments were obtained by annealing synthetic oligonucleotides with or without 5' biotin modification (IDT Biotechnology). Double stranded fragments used in EMSA assay either had biotin tags on both ends or were not labeled (cold probes).

The sequences of Sox10E2 subfragments used in these approaches were:

M2,
(SEQ ID NO: 144)
GCAATTTAACCTACAACTGCTGAGCTTGTA

M4,
(SEQ ID NO: 145)
GGCGACTGTGCTTCCGGCTGGGGCAGTG;

M8,
(SEQ ID NO: 146)
GGAGCAGGGAAACAATAGGTGATTT;

M9,
(SEQ ID NO: 147)
TGGCCAGAGAGGAAATTGGGGGTTT;

M11/12,
(SEQ ID NO: 148)
TCAGGGCACAAAGGCCCAACTGTCTAGGGGG.

The sequences of scrambled controls were selected based on the absence of binding sites with homology of greater than 70%, according to exhaustive survey of Jaspar and Transfac databases. They were as follows: Myb Co, (SEQ ID NO: 149) TCTTCAAGTCCGCCAT-GCCCGAAGG; Sox9 Co, (SEQ ID NO: 150) TACGGCAAGCTGTTCATCTGCACCA; Ets1 Co, (SEQ ID NO: 151) ATGTCTACGTCGAGCGCGACG-GCGA.

EMSA. Nuclear extracts from chicken embryonic transfected with corresponding expression plasmids(Sox9-Ets1-, cMyb- or control-pCI H2BRFP) were obtained using standard hypotonic buffer (10 mM HEPES pH7.9, 1.5 mM MgCl$_2$, 10 mM KCl, 0.5 mM DTT, 1X Complete EDTA-Free Protease Inhibitors, 0.2 mM PMSF) to isolate the nuclei and extraction buffer (20 mM HEPES pH7.9, 0.42 M NaCl, 1.5 mM MgCl$_2$, 0.2 mM EDTA, 25% (v/v) glycerol, 1 mM DTT, 1X Complete EDTA-Free Protease Inhibitors) to obtain nuclear extracts. Binding reactions and gel shift detection was performed using LightShift Chemiluminescent EMSA Kit (Thermo Fisher Scientific, Rockford, Ill.) following manufacturer's instructions.

Pull-Down Assays. Pulldown binding assays were performed using streptavidin Dynal beads (Invitrogen) and the same biotin-labeled Sox10E2 subfragments as in EMSA, carrying a single biotin tag. Dynal streptavidin beads (Invitrogen) were coated according to manufacturer's instructions, using equimolar quantities of the fragment labeled on either 5' or 3' end. 400-500 µg of embryonic nuclear proteins (extracted from cephalic regions of chicken embryos at stage HH9-HH2) in final volume of ~800 µl of binding buffer (12% glycerol, 12 mM HEPES pH 7.9, 4 mM Tris pH 7.9, 150 mM KCl, 1 mM EDTA, 1 mM DTE, and 0.1 µg/µl poly(dI-dC). These were pre-exhausted using ~1.5 mg of streptavidin Dynal beads and distributed among 4 Dynal bead preps: 2 coated with specific DNA fragment, one with scrambled control and one without DNA. Binding reactions were allowed to proceed for 30' at RT, and were subsequently washed 4 times with the binding buffer (only 1st wash contained poly(dI-dC)). After the 4$^{th}$ wash, the beads were transferred to a new tube, bound proteins eluted in 30 µl of 50 mM Tris pH 7.5, 100 mM NaCl, 5 mM EDTA, 1× Protease Inhibitors, 0.1% SDS and analyzed by Western blot using Sox9, Ets1 and cMyb antibodies.

Ets1, cMyb and Sox9 antibodies recognize cross-linked endogenous corresponding proteins. (FIG. 15A, 15B) Western blots, using Sox9 and cMyb antibodies on cross-linked or cross-linked/sonicated material performed under moderate denaturing conditions. Specific bands were noted at ~120 kDa for Sox9 and at ~80 kDa and 120 kDa for cMyb. Similar Sox9 and cMyb protein bands were detected after pull-down assays. 120 kDa cMyb protein was also bound to cMyb scrambled control (Myb CO) with 70% homology threshold (FIG. 15D). Partial denaturing conditions show that other less prominent bands likely represent complex associations rather than Sox9 or cMyb bands, as they are less prominent in the sonicated condition. (FIG. 15C) ChIP using Ets1 antibody, followed by western blot using the same target antibody. Detection was performed using IP-Western kit (GenScript, Piscataway, N.J.) and shows several bands in cross-linked and sonicated input, under moderate denaturating conditions, with a single Ets1—precipitated band (~arrow) detected in the ChIP and input lanes, but not in samples precipitated with IgG antibody. IP—Immunoprecipitated fraction, SN—1$^{st}$ supernatant, IgG IP—Immunoprecipitation with normal rabbit IgGs (negative control), M2—subfragment of Sox10E2 enhancer containing N-terminal Myb site, M11/12—subfragment of Sox10E2 enhancer containing C-terminal Myb site, Myb CO—scrambled control fragment containing no Myb sites with >70% homology, -DNA—control pulldown using streptavidin magnetic beads only, without DNA fragment.

Chromatin immunoprecipitation with Sox9, Ets1 and cMyb antibodies. For ChIP, chromatin was prepared from cranial regions of 8-12 somite chicken embryos and immunoprecipitated using Ets1 (sc-350; Santa Cruz), Sox9 (ab71762, Abcam and rabbit polyclonal, Dr. M. Wegner) and cMyb antibodies (Karafiat et al. (2005) *Cell Mol Life Sci* 62(21): 2516-2525) with normal rabbit IgGs (sc-2027, Santa Cruz; ab27478, Abcam) as negative controls. The protocol was adapted from (Buchholz et al (2006) Methods in Signal Transduction, eds Whitman M & sater Ak (CRC Press), 257-271; Dahl and Collas (2008) *Nat Protoc* 3(6): 1032-1045).

For each preparation of nuclei, cranial regions from 20 stage 8-12 somite embryos were dissected in Ringer's solution and transferred to 1 ml isotonic buffer (0.5% Triton X-100, 10 mM Tris-HCl, pH 7.5, 3 mM CaCl2, 0.25 M sucrose, protease inhibitor tablet (Complete Protease Inhibitor EDTA-free, Roche), 1 mM DTT, and 0.2 mM PMSF) on ice (adapted from Buchholz et al. 2006). Tissue was homogenized using Dounce homogenizer and cells cross-linked by adding formaldehyde to a final concentration of 1% and nutated for 10' at room temperature. Glycine (final concentration of 125 mM) was added to stop the cross-linking reaction and solution was incubated by nutation for 5' at RT. The cross-linked cells were washed 3 times and cell pellets were either snap frozen in liquid nitrogen and kept at −80° C. until the ChIP procedure. Preparations were kept up to a month without altering the quality of results. The pellets were re-suspended in isotonic buffer and nuclei isolated using Dounce homogenizer washed and lysed in SDS lysis buffer (1% SDS, 10 mM EDTA, 50 mM Tris-HCl, pH 8.0) for 10'-1 h. The lysate was then diluted three-fold with ChIP dilution buffer (0.01% SDS, 1.2 mM EDTA, 16.7 mM Tris-HCl, pH 8.0, 167 mM NaCl, 1 mM DTT, 0.4 mM PMSF, and protease inhibitors) and ½ of chromatin (420 ul) was sonicated using Misonix 4000 sonicator at following settings: Amp 3, 10 consecutive cycles of 30" sonication each with 1' pause in between. Triton X was added to the sonicated material to a final concentration of ~1%, chromatin was cleared by centrifugation, diluted 3-4 times with ChIP Dilution Buffer w/1.1% Triton X-100 and was distributed between 2-3 antibody/bead complexes (400 ul each) and incubated ON at 4° C. 50 ul of the chromatin preparation was conserved at −80° C. as the input fraction. Antibody/magnetic bead were prepared as per Young protocol. Post-immunoprecipitation washes were performed using RIPA wash buffer (50 mM Hepes-KOH, pH 7.6, 500 mM LiCl, 1 mM EDTA, 1% NP-40, 0.7% Na-Deoxycholate). The complexes were then washed with Tris-EDTA/NaCl (10 mM Tris-HCl, 1 mM EDTA pH 8.0, 50 mM NaCl) for 5' and transferred to a new chilled tube, prior to last separation (Dahl and Collas, 2008). The chromatin was eluted in elution buffer (1% SDS, 10 mM EDTA, 50 mM Tris-HCl, pH 8.0) and cross-link reversed overnight by incubation at 65° C. The samples were consecutively treated with RNase A (0.2 mg/ml) and then Proteinase K (0.2 mg/ml), extracted with Phenol/Chloroform/Isoamyl Alcohol, precipitated and resuspended in 50 ul of 10 mM Tris pH 8.0. Real-time PCR reactions were performed in a 96-well plate ABI7000 QPCR machine. Reactions were set up using SybrGreen (Biorad), 450 µM of each (forward and reverse primer) and 1 ul of each ChIP reaction or 1:100-200 dilution of Input fraction. The $\Delta\Delta C_t$ method was used for quantification and calculations performed according to ChIP-qPCR Data Analysis instructions (SupperArray, Bioscience Corporation). In order to select suitable negative control primers, large regions (potentially corresponding to genomic deserts) of chromosome 1 were surveyed. Because Ets1 binding sites are present in large proportion of the chicken genome. non-specific binding was a concern; therefore, 8-10 different sets of primers were tested.

The primers presented in FIG. 13M corresponding to Sox10E2 fragment were:

```
Sox10E2_1
                                  (SEQ ID NO: 152)
5'-TGCTCCTGCTGCTTATCA-3';

Sox10E2_1 rev
                                  (SEQ ID NO: 153)
5'-ATCAGCTCCACTGCACAT-3';

Sox10E2_2
                                  (SEQ ID NO: 154)
5'-TGATAAGCAGCAGGAGCA-3';

Sox10E2_2 rev
                                  (SEQ ID NO: 155)
5'-TGAGCAGGT-TGCTGTGGAAA-3'.
```

Control primer sets that amplify negative control region situated on the same chromosome as Sox10 locus were as follows:

```
negcont_1
                                  (SEQ ID NO: 156)
5'-TCGGATTTTAATGGGCTCAG-3;

negcont_1 rev
                                  (SEQ ID NO: 157)
5'-CCGCAGATAGTTCTGCATCA-3';

negcont_2
                                  (SEQ ID NO: 158)
5'-GGTTGGATTTCCAGTCTCCA-3';

negcont_2 rev
                                  (SEQ ID NO: 159)
5'-TGTTTTGCTG-GACAATCTGC-3'.
```

Figure 16A:
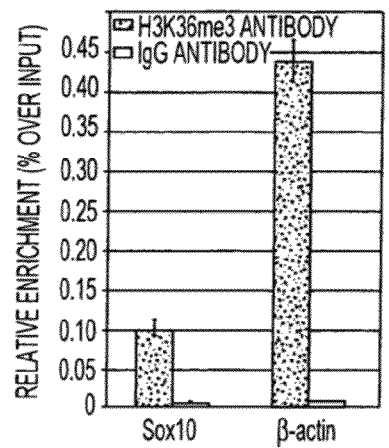
FIGS. 16A-16D show calculated direct binding of Ets1, cMyb and Sox9 to Sox10E2.
Figure 16B:
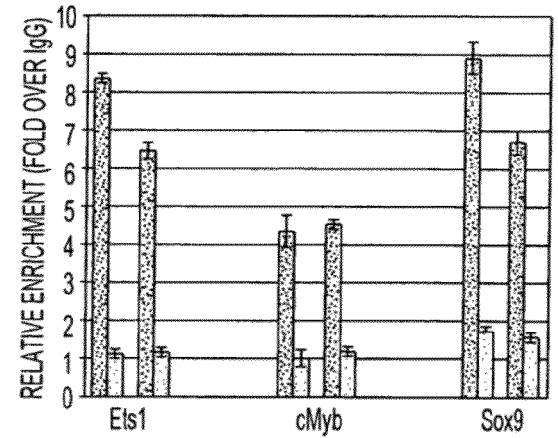
Figure 16C:
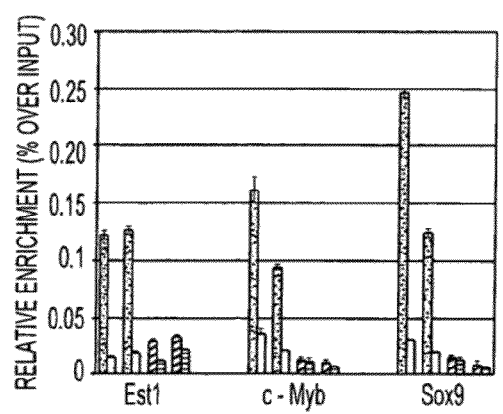
Figure 16D:
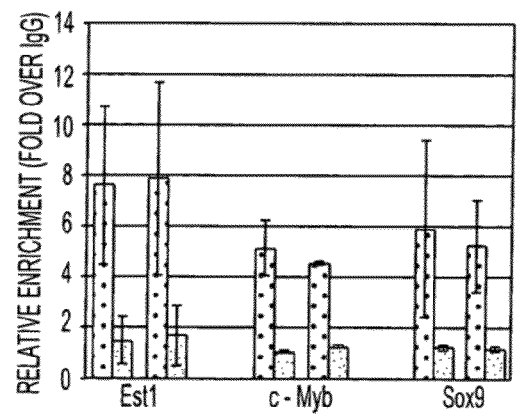

Ets1, cMyb and Sox9 bind directly to Sox10E2 enhancer element in vivo. Direct binding of Ets1, cMyb and Sox9 transcription factors to the Sox10E2 regulatory element driving the onset of Sox10 expression in the delaminating neural crest was assessed using chromatin immunoprecipitation (qChIP). (FIG. 16A) shows qChIP positive control using antibody against H3K36me3, chromatin mark generally associated with active gene transcription. Chromatin immunoprecipitation (ChIP) shows high occupancy of H3K36me3 mark in proximity of the transcriptional start site (TSS) of Sox10 and control active β-actin locus. Relative enrichment over input using specific and negative control antibodies (normal rabbit IgGs) are presented. FIG. 16*b* shows qChIP results obtained using specific target antibodies (Sox9, Ets1 and cMyb) to precipitate chromatin regions specifically bound by those factors. The results presented as relative enrichment over input using specific or negative control antibody (normal IgGs) were obtained by quantitative PCR where the same amount of DNA from each pulldown was used in a separate reaction and two primer sets specific with Sox10E2 region (red bars) and two primer sets within negative non-bound region (grey bars). FIG. 16*c* shows enrichment is expressed relative to input DNA using the same amount of DNA in the QPCR reaction for each Chromatin IP. Enrichment of the specific factors (Ets1, cMyb or Sox9) at Sox10E2 enhancer region is presented as red bars, enrichment of specific factor at negative control regions is presented in blue. Background levels (mean enrichment from control antibodies) at enhancer and negative control regions are shown as pale red or pale blue bars, respectively. FIG. 16*d* shows means and standard deviations of relative enrichment (fold over negative control antibody) are presented from 3-4 independent experiments for each specific antibody used. Green bars represent enrichment at Sox10E2, grey bars at negative control regions.

Over Expression Constructs

Open reading frames of chick Sox9, cMyb and Ets1 genes were amplified from a full length cDNA clones or chicken cDNA (Sox9 cDNA clone was a gift from Yi-Chuan Cheng, Ets1 clone was isolated from the stage 8-12 somites chicken macroarrayed cDNA library constructed by Laura Gammill (Kelsh R N (2006) *Bioessays* 28(8):788-798) and cloned into XhoI/EcoRV or XhoI/ClaI digested pCI H2B-RFP expression vector. The Sox9 and Ets1 rescue constructs were generated from expression constructs by PCR, using primers carrying mutations within the morpholino target sites that do not alter the amino acid sequence of the recombinant proteins. The following primers were used:

```
Sox9_5'
                                                  (SEQ ID NO: 160)
5'-AATTCTCGAGGCCACCTGCTCAAGGGCTACGACTGG-3'
and Sox9_3'
                                                  (SEQ ID NO: 161)
5'-ATTAGATATCTTTAAGGCCGGGTGAGCTGC-3';

Ets1_5'
                                                  (SEQ ID NO: 162)
5'-AATACTCGAGGGCCTCAACCATGAAGGCGGCGGTGGA-3'
and Ets1_3'
                                                  (SEQ ID NO: 163)
5'-ATTAGATATCTCACTCATCAGCATCTGGCTTG-3';

cMyb_5'
                                                  (SEQ ID NO: 164)
5'-ATTACTCGAGgccaccATGGCCCGGAGAC;

cMyb_3',
                                                  (SEQ ID NO: 165)
5'-ATTAATCGATTCACATCACCAGAGTCC;

Sox9mut_5'
                                                  (SEQ ID NO: 166)
5'-ATTACTCGAGgccaccATGAActTgtTgGAtCCCTTCATGAAAATGAC;

Ets1mut_5',
                                                  (SEQ ID NO: 167)
5'-ATTACTCGAGTCAACCATGAAaGCtGCcGTcGAttTaAAaCCCACCCTGACCATCA.
```

Transcriptional inputs into the Sox10E2 regulatory region. FIG. 8*a* shows EGFP pattern of expression in neural crest cells driven by the intact Sox10E2 regulatory region. FIGS. 8B, 8C show EGFP expression is abolished in cranial neural crest when binding motifs for putative upstream regulators, SoxE and a pair of Myb are mutated (SoxE, M8 in FIG. 8B and Myb, M2/M12 in FIG. 8C). FIG. 8D shows a mutation of a single Myb binding site mildly decreases EGFP reporter expression while FIG. 8*e* shows that a NFkB1 mutation does not affect reporter signal.

Comparative Genomic Analyses

To identify highly conserved genomic regions, the ECR Browser software was employed. Chicken, zebrafish, *Xenopus*, opossum, mouse, chimpanzee, dog, rat and human genomic sequences were downloaded using UCSC genome browser. Following instructions available on the ECR website, these sequences were computationally compared from between all the species, with conservation parameters set to 70-80%. The "zoom in" feature, built in the program, was used to closely analyze the sequence conservation by increasing the threshold up to 90% and using different window sizes ranging from 20 bp to 50 bp. To search for putative binding motifs, we used the jaspar_core database from Jaspar and the P-Match program available through Transfac database. Briefly, the 264 bp-long sequence of Sox10E2 genomic fragment was uploaded into these programs using desired parameters and the programs returned potential binding motifs based on the position weight matrix (PWM) score. Simultaneously, using rVista 2.0, Sox10E2 sequence was aligned and compared to the corresponding mouse sequence to screen the latter sequence for conserved putative binding motifs identified in chicken by either Jaspar, Transfac or both search engines. We used the position weight matrix (PWM) score, a value given to a site based on the distribution frequency of each base at each position (Sauka-Spengler T & Bronner-Fraser M (2008) *Nat Rev Mol Cell Biol* 9(7): 557-568) to determine the probability of binding score. This was then used to guide mutational analysis, since, as with any informatics approach, there are several caveats: 1) this only predicts motifs for factors with known consensus sites; 2) not all functional sites have high PWM scores since they can differ greatly from consensus (Antonellis et al. (2006) *Hum Mol Genet* 15(2): 259-271) and 3) not all sites with high PWM are functional.

Cell Death and Proliferation Assays

Histology. Embryos electroporated unilaterally with single or triple morpholino (@3 mM concentration) were fixed in 4% paraformaldehyde and dehydrated to 100% methanol. After re-hydration, embryos were cryoprotected in 15% sucrose, equilibrated in 15% sucrose/7.5% gelatin, embedded in 20% gelatin and sectioned at 10 um using Micron cryostat.

TUNEL reaction. The slides were first washed twice in PBS at 42° C. for 10' to remove gelatin, followed by 3-4 10' washes in PBST (PBS+0.5% Triton X-100) at RT. After 10' incubation in Permeabilization solution (0.1% sodium Citrate, 0.5% Triton in PBS) and two PBST rinses, the slides were incubated in Tunel reaction mix (In Situ Cell Death Detection Kit, TMR red, Roche). Labeling solution was first diluted 10 times with Tunel buffer (30 mM Tris pH 7.2, 140 mM Sodium cacodylate, 1 mM $CoCl_2$) and then combined with enzyme mix as per manufacturer's instructions (1 part enzyme+9 parts label). A positive control slide, pre-treated with DNAse I (2 ul of 10 U/ul stock in 100 ul of DNase buffer: 10 mM $CaCl_2$, 40 mM Tris Cl pH7.4, 10 mM $MgCl_2$, mM NaCl, for 1 h at RT) was prepared in advance, rinsed with 2 mM EDTA in PBST to quench DNase activity, washed twice in PBST and stained with Tunel reaction mix as well. Negative control slide was incubated in Tunel labeling mix, without TdT enzyme. The labeling was performed in the dark, for 4 h in a humidified chamber at 37° C. The slides were then washed 3×PBST for at least 15 min each time, the positive control slide was rinsed in a separate container.

Immunostaining. The slides were incubated in blocking buffer (10% donkey serum in PBST) for 1 hour followed by primary antibodies diluted in blocking buffer overnight at 4° C., (1:1000 rabbit antiPh3 (Phospho-Histone 3) and 1:800 Alexa 488 goat anti FITC). Slides were then rinsed 3-4 times in PBST, 30 min each wash. Secondary antibody was diluted in PBST or blocking buffer and applied for 1 hour at RT. As the TUNEL staining is red (TMR red), we used 1:1000 Alexa 350 goat anti-Rabbit (blue) to detect antiPh3 and FITC (morpholino) was labeled in green. All consecutive sections from the cranial region were counted and number of Ph3-(and Tunel-) positive cells within the neural fold was compared between morpholino-ed and control sides for individual, triple and control morpholinos. We present the mean value of electroporated/control side ratio for triple and control morpholinos. The statistical values were calculated using unpaired student t-test.

Ets1 and cMyb transcription factors are necessary for activation of Sox10E2 regulatory element. FIG. 9A shows control morpholino (MO) (right; red) has no effect on Sox10E2-driven Cherry (FIG. 9B; green) compared to non-electroporated (left) side. FIG. 9D shows cMyb MO significantly reduces, whereas Ets1 MO (FIG. 9G) abolishes Sox10E2-driven Cherry expression, (FIGS. 9E, 9H, respectively. FIGS. 9C, 9F, 9I are merged images of FIGS. 9A/B, 9D/E and 9G/H, respectively). White dotted lines=midline. Green/red channels inverted for consistency.

In situ hybridization is shown in FIGS. 9J-9N. FIGS. 9J-9L show that endogenous cMyb, Sox9 and Ets1 expression precedes that of Sox10, consistent with being upstream regulators. At HH6, cMyb is expressed within the neural plate border (FIG. 9J) and confined to dorsal neural folds containing CNC by HH8 (FIGS. 9K; 9K'; arrowheads). At HH10, cMyb is observed in migrating neural crest (FIG. 9L and section at dotted line, FIG. 9L' arrows). At HH8, prior to Sox10 onset, Sox9 (FIG. 9M) and Ets1 (FIG. 9N) are expressed by presumptive cranial neural crest in the dorsal neural tube.

Morpholino-mediated Knock-down Experiments

Morpholino-mediated knock-down experiments were performed by injecting the translation-blocking, FITC-labelled morpholino antisense oligonucleotides in one half of the epiblast (right to the primitive streak) or, in some cases, by double electroporations to differentially transfect each half of the embryo ex-ovo. For Sox10E2, double electroporations were performed by introducing each morpholino combined with the Sox10E2-Cherry plasmid on the right side and the Sox10E2-Cherry reporter only on the left side of the embryo. Morpholinos for knockdowns in conjunction with SOX10E2-EGFP were obtained from Gene Tools (Philomath, Oreg.) and their sequences are as follows:

```
Ets1
                                 (SEQ ID NO: 168)
5'-GCTTCAGGTCCACCGCCGCCTTCAT-3;

cMyb
                                 (SEQ ID NO: 169)
5'-ATGGCCGCGAGCTCCGCGTGCAGAT-3';

Sox9
                                 (SEQ ID NO: 170)
5'-GGGTCTAGGAGATTCATGCGAGAAA-3';

Control
                                 (SEQ ID NO: 171)
5'-ATGGCCTCGGAGCTGGAGAGCCTCA-3'.
```

The final molar concentration of each morpholino oligonucleotide used was 725 nM.

Morpholino-mediated Sox9 knock-down significantly reduces Sox10E2 regulatory activity. FIG. 10A shows FITC-labeled control morpholino (in red) does not affect Sox10E2 driven Cherry expression in FIG. 10B (green). FIG. 10C shows a merged image of FIGS. 10A and 10B, revealing with control morpholino (red) with Sox10E2 driving expression of Cherry (green). FIG. 10D shows Sox9 FITC-labeled morpholino (red) strongly reduces Sox10E2 driven Cherry expression as shown in FIG. 10E (green, white arrow). FIG. 10F shows a merged image of 10D and 10E. Embryos were electroporated on the right side only. The images were pseudo-colored using Photoshop, with green and red channels inverted for consistency, indicative of reporter expression.

Sox9, cMyb and Ets1 are required for endogenous Sox10 expression in delaminating neural crest cells. FIGS. 11A-1M show HH8+ embryos with unilateral electroporation of Sox9 (FIGS. 11A, 11E), cMyb (FIGS. 11B, 11F) and Ets1 (FIGS. 11C, 11G) morpholinos (MO) show significant decrease in endogenous Sox10 expression in delaminating CNC compared to non-electroporated side, whereas control MO(FIGS. 11L, 11M) has no effect. Co-electroporation of Sox9, cMyb, Ets1 MOs completely abolishes endogenous Sox10 expression (10D,10H). Showing specificity, the effect is rescued by co-electroporation with corresponding expression construct: Sox9 MO+Sox9 DNA(10I), cMyb MO+cMyb DNA(10J) or Ets1 MO+Ets1 DNA(10K). Statistical relevance by chi-squared test of MOs on Sox10 expression was p<0.02; of rescues was p<0.03(Sox9; Ets1) and p≤0.04(cMyb).

Electroporation of Ets1, cMyb, Sox9 and control morpholinos does not affect cell proliferation and does not induce apoptotic cell death. FIGS. 12A, 12b 12B show embryos electroporated with FITC-labeled triple (Ets1, cMyb and Sox9) or control morpholinos. FIGS. 12C, 12D show embryos sectioned, followed by TUNEL staining. FIGS. 12E, 12F show anti-Phospho-Histone H3 (Ph3) antibody staining of sections. FIGS. 12G, 12H show overlays of FITC, TUNEL and Ph3 staining presented in (FIGS. 12A, 12C. 12E) and (FIGS. 12B, 12D, 12F), respectively. All consecutive sections from the cranial region were counted and the number of Ph3- (and Tunel-) positive cells within the neural fold was compared between morpholino-ed and control sides. Mean value and standard deviation of electroporated/control side ratio from four independent embryos are presented (FIG. 12I shows TUNEL, red bars; FIG. 12J shows Ph3, blue bars). The statistical calculations performed using unpaired student t-test show no statistically significant differences in cell death or proliferation counts between electroporated and control sides of embryos receiving either three specific morpholinos or control (at 3 mM).

Binding motifs for SoxE, Ets and Myb within Sox10E2 enhancer need to be functional in order for ectopic reporter expression to occur when misexpressing Sox9, cMyb and/or Ets1, individually or in combination. FIG. 14D shows ectopic SOX10E2-activated EGFP expression in the extraembryonic region, ectoderm cells (arrowheads) and along the neural tube when Sox9-pCI H2B-RFP, Ets1-pCI H2B-RFP and cMyb-pCI H2B-RFP (red) are simultaneously over-expressed as shown in FIG. 14A. FIG. 14B shows that combined Sox9 and cMyb misexpression fails to activate ectopic EGFP expression through a mutated Sox10E2 regulatory region (M9) that lacks an Ets binding motif (FIG. 14E). Whereas, overexpressing Sox9 and Ets (FIG. 14C) simultaneously can activate weak reporter expression (arrows) through a mutated Sox100E2 lacking one Myb (M12) binding motif (FIG. 14F).

Sox9, cMyb and Ets1 overexpression ectopically induces Sox10E2 regulatory activity. EGFP is observed in migrating crest and otic vesicle (OV) when Sox10E2-EGFP is co-electroporated with control plasmid, pCI H2B-RFP (FIGS. 13A, 13F). Overexpression of either Sox9 (FIGS. 13B, 13G), Ets1 (FIGS. 13C, 13H) or cMyb (FIGS. 13D, 13I) ectopically activates Sox10E2-driven EGFP expression in extraembryonic ectoderm (white arrows). In FIG. 13H, arrowheads show EGFP expression in posterior neural tube. Misexpression of Ets1(FIG. 10E) fails to activate ectopic EGFP expression (FIG. 13J, arrows) in a mutated Sox10E2 construct lacking an Ets binding motif(M9).

EMSA shows a clear band shift (FIG. 13K, white arrowhead) when nuclear extracts containing overexpressed Sox9, Ets1 or cMyb proteins are combined with Sox10E2 subfragments, M11, M9 and M2, respectively ($1^{st}$ lane). This binding is outcompeted when excess non-labeled probe is added ($2^{nd}$ lane) and absent from nuclear extracts from control plasmid-transfected cells ($3^{rd}$ lane). Biotinylated Sox10E2 subfragments (M8,M11-Sox9, M4,M9-Ets1 and M2,M12-cMyb), as well as scrambled control fragments and non-coated Dynal streptavidin beads, used as bait in a DNA pulldown assay show specific transcription factor binding as analyzed on a Western blot in FIG. 13L. FIG. 13M shows direct binding of Ets1, cMyb and Sox9 to the Sox10E2 enhancer element in vivo as assessed by qChIP. Binding to Sox10E2 (red bars) or control region (grey bars) was assessed with two primer sets for each region and expressed as relative enrichment of target over control antibody; graph reflects mean±SD from a representative experiment. qChIP was performed 3-4 times for each factor. Enrichment relative to input DNA from all independent experiments is shown in FIGS. 16A-D.

Short-hairpin RNA Vectors

Figure 25:
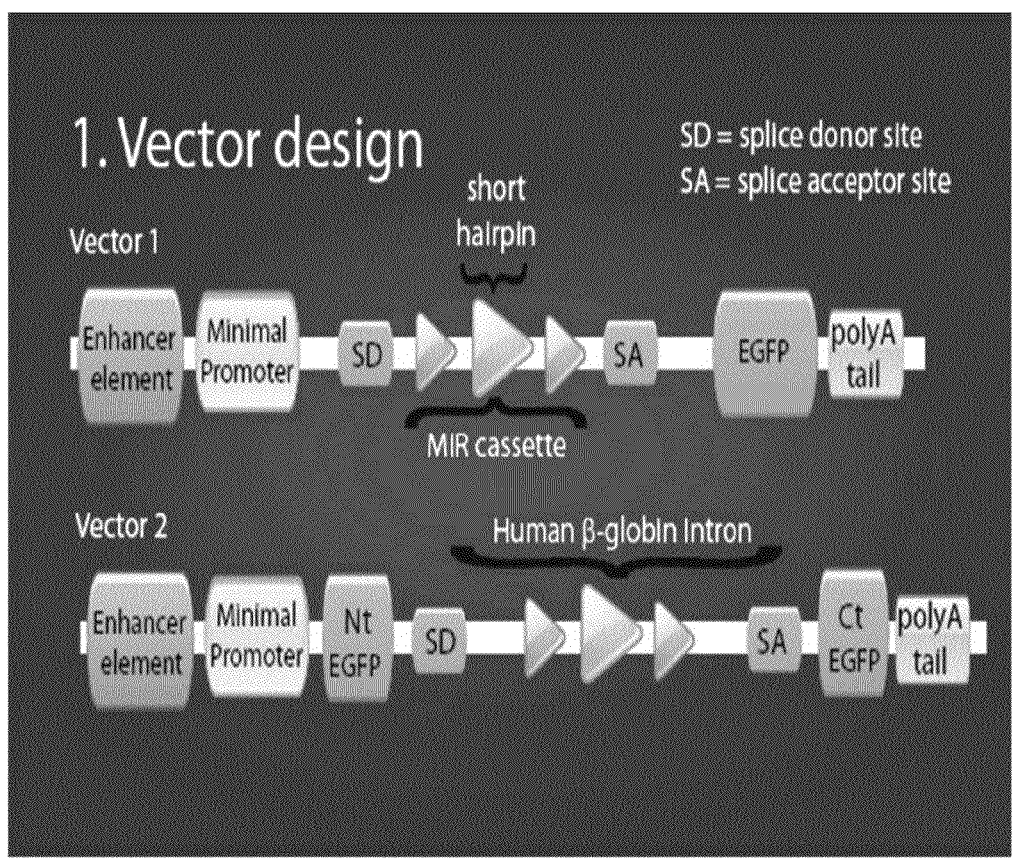
FIG. 25 shows a schematic for the design and concept of short hairpin RNA vectors. Vector 2 differs from Vector 1 in that Vector 2 has surrounded the microRNA with human beta globin intron sequence.

Vector design and modification. The vectors in FIGS. 24A, 24B were generated through sequential generations of adaptation and modification. Enhancers are cloned into a KpnI/BglII multiple cloning site and short hairpins cloned into a unique EcoR1/XhoI sites. In FIG. 24A, the NC enhancer sequence (SEQ ID NO: 4) is shown. The full sequence schematic for the vector in FIG. 24B is shown in Appendix (SEQ ID NO: 172). The general vector designs are shown in FIG. 25 wherein Vector 1 concept is the vector of FIG. 24A and Vector 2 concept is the vector of FIG. 24B. Integration sites for genomic insertion can be provided in either vector providing the same knockdown results.

Short hairpin design and amplification. Oligonucleotides (oligos) were selected using software designed by the Hannon laboratory at Cold Spring Harbor Laboratory, and the 90-mer ordered from IDT (Integrated DNA Technologies Inc., San Diego 92121, USA). These were amplified and EcoR1/XhoI sites added using the primers: SH2fwd (SEQ ID NO: 173) (5'-GATGGCTG-CTCGAGAAGGTATATTGCT-GTTGACAGTGAGCG-3') and SH2reverse (SEQ ID NO: 174) (5'-GTCTAGAGGAATTCCGAGGCAGTAGGCA-3'). This was performed using the following PCR reaction: Thermopol Buffer (1× final conc.) Mg2SO4 2 mM. DMSO 5%, dNTPs 200 uM, Template oligo 100 ng, Forward Primer 0.5 uM, Reverse Primer 0.5 uM, VENT Polymerase 1 U/reaction. The conditions used are: 1) 94° C. 5 mins, 2) 94° C. 30 seconds, 3) 54° C. 30 seconds, 4) 75° C. 30 seconds, cycles 2-4 repeated 12 cycles; 5) 75° C. 2 mins.

Electroporation and analysis for short-hairpin miRNA vectors. Unless otherwise stated, embryos were electroporated at HH3+–HH4 (Hamburger & Hamilton 1951) and placed in EC culture (Chapman et al. 2001, Dev. Dyn. 220(3): 284-289). The left side only of the neural plate was electroporated in all cases (unilateral electroporation). Embryos were electroporated with 5×7V of a pulsed square current (50 ms ON 100 ms OFF) and incubated at 37 degC, 5% CO2 until they reached the required somite number. For QPCR, embryos were bisected down the midline into electroporated and non-electroporated sides and cDNA synthesis/QPCR was performed separately on each half. Data from electroporated/non-electroporated for targeted and control (RFP) embryos were compared (FIG. 26). Electroporation at 4 mg/ml (FIG. 26) gives efficient knockdown of target gene during the period the enhancer is active. When unilateral electroporation was unfeasible, embryos were bilaterally electroporated whole embryos used for QPCR with targeted versus RFP results presented. For experiments using the MSX-shFoxD3 and Spalt-4-shPax3 vectors, embryos were electroporated at HH3 at a point prior to ingression of the mesoderm. This allows sufficient time for transcription of short hairpins to begin prior to expression of the targeted gene. In situ hybridization as shown in FIGS. 26A, 26B were performed as described herein.

Neural Crest Cell Isolation/Dissociation

Electroporate the reporter construct of interest (enhancer driving fluorescent protein) or use the transgenic mouse expressing the fluorescent reporter under the control of neural crest enhancer. Dissect the region of interest. Collect tissue in Ringer's and keep on ice. Thaw a vial of each: dispase (prepared in DMEM+Hepes at a cc of 1.5 mg/ml) and trypsin (Trypsin-EDTA: 1×0.05% Trypsin, 0.53 mM EDTA in HBSS). Use the 37° Celsius (C) water bath for 5 min. Treat the dissected tissue with 2 ml of dispase for 10 min at 37° C. Use the 15 ml falcon tube, and triturate (using 2 ml plastic sterile pipets) and incubate for additional 5 min at 37° C. Before trituration, pipet up and down media +10% FBS to coat the pipet and prevent cells from sticking to it. Triturate, add 40 ul of Trypsin and incubate for 1 min. Stop the reaction by adding 10 mls DMEM, 10% FBS. Centrifuge at 1000 ref for 10 min. Remove the supernatant, re-suspend the cells in 1 ml of Hanks solution (w/o phenol red+2.5 mg/ml BSA fraction V). Place the 40 micrometer filter on a 50 ml falcon tube. Pass the 1 ml+ cells through the filter. Take out 10 ul of Hanks+ cells and add 10 ul of trypan blue. Count the cells using hemocytometer: (# of cells×dilution factor)×2×10^4=# of cells/ml. Take a small sample and look under fluorescence microscope. Centrifuge at 1000 ref for 10 min. Take out ~600 ul of Hanks solution and leave cells re-suspended in the remaining 300-350 ul of hanks solution. Transfer the cells in Hanks solution to a 5 mls falcon tube. Prepare a few 1.5 eppendorf tubes (4 per sample to be sorted) with approximately 1 ml of media (DMEM+10% FBS) to collect sorted cells. Run the cell suspension through the FACS (Fluorescence-Activated Cell Sorting) machine and collect isolated neural crest cells that express fluorescent marker under the control of neural crest enhancers. For incubations at 37° C. use a water bath. To reduce the stickiness of the cells, due to accidental nuclear lysis, the prep can be treated with DNAse for a short time. This treatment should be avoided if whole cell extracts are to be used in DNA sensitive applications.

In summary, DNA enhancer sequences are provided for use in constructs to identify early stage embryonic cells. The enhancer sequences can be used in parallel with short-hairpin RNA in a vector construct for endogenously regulated gene knockdowns. The disclosed enhancer sequences can be used to isolate a selected population of early stage embryonic cells.

All references cited in the application are incorporated in their entirety as if explicitly recited herein, particularly all references directed to methodologies of synthesis.

What is claimed is:

1. An isolated nucleic acid sequence consisting of SEQ ID NO: 4.

2. A nucleic acid vector for down-regulating gene expression comprising:
   a short-hairpin RNA sequence under transcriptional control of at least one enhancer sequence having the sequence as set forth in SEQ ID NO: 4.

3. An expression vector comprising the sequence of SEQ ID NO: 4 and a nucleic acid sequence encoding a reporter protein.

4. The expression vector of claim 3, wherein the reporter protein is a fluorescent protein.

5. The expression vector of claim 3, wherein the expression vector is a viral vector.

6. A method of isolating mammalian cells expressing FoxD3, the method comprising:

introducing to a population of isolated mammalian cells an expression vector comprising the sequence of SEQ ID NO: 4 and a nucleic acid sequence encoding a reporter protein; and identifying introduced cells that produce the reporter protein.

7. The method of claim 6, wherein the reporter protein is a fluorescent protein.

8. The method of claim 6, further comprising isolating the cells expressing the reporter protein.

9. The method of claim 6, wherein the isolating is performed by flow cytometry.

\* \* \* \* \*